United States Patent
Hynes

(10) Patent No.: US 8,410,128 B2
(45) Date of Patent: Apr. 2, 2013

(54) TRIAZOLOPYRIDINE COMPOUNDS USEFUL AS KINASE INHIBITORS

(75) Inventor: John Hynes, Washington Crossing, PA (US)

(73) Assignee: Bristol-Myers Squibb Company, Princeton, NJ (US)

( * ) Notice: Subject to any disclaimer, the term of this patent is extended or adjusted under 35 U.S.C. 154(b) by 130 days.

(21) Appl. No.: 12/738,860

(22) PCT Filed: Jun. 18, 2009

(86) PCT No.: PCT/US2009/047728
§ 371 (c)(1),
(2), (4) Date: Apr. 20, 2010

(87) PCT Pub. No.: WO2009/155389
PCT Pub. Date: Dec. 23, 2009

(65) Prior Publication Data
US 2011/0077243 A1  Mar. 31, 2011

Related U.S. Application Data

(60) Provisional application No. 61/074,201, filed on Jun. 20, 2008.

(51) Int. Cl.
| | | |
|---|---|---|
| A01N 43/40 | (2006.01) | |
| A01N 43/42 | (2006.01) | |
| A01N 43/78 | (2006.01) | |
| A01N 43/64 | (2006.01) | |
| A61K 31/435 | (2006.01) | |
| A61K 31/44 | (2006.01) | |
| A61K 31/41 | (2006.01) | |

(52) U.S. Cl. ......... 514/277; 514/299; 514/365; 514/383
(58) Field of Classification Search .................. 514/299, 514/277, 365, 383
See application file for complete search history.

(56) References Cited

U.S. PATENT DOCUMENTS

| | | | |
|---|---|---|---|
| 5,658,903 A | 8/1997 | Adams et al. | |
| 5,932,576 A | 8/1999 | Anantanarayan et al. | |
| 5,945,418 A | 8/1999 | Bemis et al. | |
| 5,977,103 A | 11/1999 | Adams et al. | |
| 6,087,496 A | 7/2000 | Anantanarayan et al. | |
| 6,130,235 A | 10/2000 | Mavunkel et al. | |
| 6,147,080 A | 11/2000 | Bemis et al. | |
| 6,251,914 B1 | 6/2001 | Adams et al. | |
| 6,277,989 B1 | 8/2001 | Chakravarty et al. | |

FOREIGN PATENT DOCUMENTS

| | | |
|---|---|---|
| EP | 0 547 568 A1 | 6/1993 |
| EP | 1 247 810 A1 | 10/2002 |
| WO | WO 00/12074 | 3/2000 |
| WO | WO 00/12497 | 3/2000 |
| WO | WO 00/56738 | 9/2000 |
| WO | WO 01/27089 | 4/2001 |
| WO | WO 01/34605 | 5/2001 |
| WO | WO 2005/097052 A1 | 10/2005 |
| WO | WO 2006/018727 A2 | 2/2006 |
| WO | WO 2006/091897 A2 | 8/2006 |
| WO | WO 2007/103760 A2 | 9/2007 |
| WO | WO 2008/147557 A2 | 12/2008 |

OTHER PUBLICATIONS

Henry, Jr., et al., "p38 mitogen-activated protein kinase as a target for drug discovery", Drugs of the Future 1999, vol. 24, pp. 1345-1354.
Salituro et al., "Inhibitors of p38 MAP Kinase: Therapeutic Intervention in Cytokine-Mediated Diseases," Current Medicinal Chemistry, 1999, vol. 6, pp. 807-823.
Rankin et al., "The Therapeutic Effects of an engineered Human Anti-Tumor Necrosis Factor Alpha Antibody (CDP571) in Rheumatoid Arthritis," British Journal of Rheumatology, 1995, vol. 34, pp. 334-342.
Moreland et al., "Etanercept therapy in rheumatoid arthritis. A randomized, controlled trial," Ann. Intern. Med., 1999, vol. 130, pp. 478-486.

*Primary Examiner* — Yong Chong
(74) *Attorney, Agent, or Firm* — Laurelee A. Duncan; Gary D. Greenblatt

(57) ABSTRACT

A compound of Formula (I) and enantiomers, diastereomers and pharmaceutically-acceptable salts thereof. Also disclosed are pharmaceutical compositions containing compounds of Formula (I), and methods of treating conditions associated with the activity of p38 kinase.

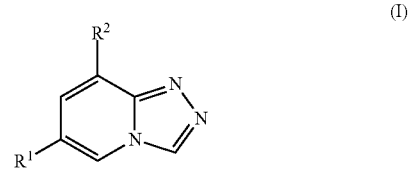

12 Claims, No Drawings

TRIAZOLOPYRIDINE COMPOUNDS USEFUL AS KINASE INHIBITORS

This application claims priority from U.S. Provisional Application No. 61/074,201, filed Jun. 20, 2008, incorporated in its entirety herein by reference.

FIELD OF THE INVENTION

This invention relates to triazolopyridine compounds useful for treating p38 kinase-associated conditions. The invention further pertains to pharmaceutical compositions containing at least one compound according to the invention useful for treating kinase-associated conditions, such as p38 kinase-associated conditions, and methods of inhibiting the activity of kinase in a patient.

BACKGROUND OF THE INVENTION

A large number of cytokines participate in the inflammatory response, including IL-1, IL-6, IL-8 and TNF-α. Overproduction of cytokines such as IL-1 and TNF-α are implicated in a wide variety of diseases, including inflammatory bowel disease, rheumatoid arthritis, psoriasis, multiple sclerosis, endotoxin shock, osteoporosis, Alzheimer's disease, and congestive heart failure, among others [Henry et al., Drugs Fut., 24:1345-1354 (1999); Salituro et al., Curr. Med. Chem., 6:807-823 (1999)]. Evidence in human patients indicates that protein antagonists of cytokines are effective in treating chronic inflammatory diseases, such as, for example, monoclonal antibody to TNF-α (Enbrel) [Rankin et al., Br. J. Rheumatol., 34:334-342 (1995)], and soluble TNF-α receptor-Fc fusion protein (Etanercept) [Moreland et al., Ann. Intern. Med., 130:478-486 (1999)].

The biosynthesis of TNF-α occurs in many cell types in response to an external stimulus, such as, for example, a mitogen, an infectious organism, or trauma. Important mediators of TNF-α production are the mitogen-activated protein (MAP) kinases. These kinases are activated in response to various stress stimuli, including, but not limited to, proinflammatory cytokines, endotoxin, ultraviolet light, and osmotic shock.

One important MAP kinase is p38 kinase, also known as cytokine suppressive anti-inflammatory drug binding protein (CSBP) or IK. Activation of p38 requires dual phosphorylation by upstream MAP kinase kinases (MKK3 and MKK6) on threonine and tyrosine within a Thr-Gly-Tyr motif characteristic of p38 isozymes. There are four known isoforms of p38, i.e., p38α, p38β, p38γ, and p38δ. The α and β isoforms are expressed in inflammatory cells and are key mediators of TNF-α production. Inhibiting the p38α and β enzymes in cells results in reduced levels of TNF-α expression. Also, administering p38α and β inhibitors in animal models of inflammatory disease has proven that such inhibitors are effective in treating those diseases. Accordingly, the p38 enzymes serve an important role in inflammatory processes mediated by IL-1 and TNF-α.

Compounds that reportedly inhibit p38 kinase and cytokines, such as IL-1 and TNF-α for use in treating inflammatory diseases, are disclosed in U.S. Pat. Nos. 6,277,989 and 6,130,235 to Scios, Inc; U.S. Pat. Nos. 6,147,080 and 5,945,418 to Vertex Pharmaceuticals Inc; U.S. Pat. Nos. 6,251,914, 5,977,103 and 5,658,903 to Smith-Kline Beecham Corp.; U.S. Pat. Nos. 5,932,576 and 6,087,496 to G.D. Searle & Co.; PCT publication numbers WO 00/56738 and WO 01/27089 to Astra Zeneca; WO 01/34605 to Johnson & Johnson; WO 00/12497 (quinazoline derivatives as p38 kinase inhibitors); WO 00/56738 (pyridine and pyrimidine derivatives for the same purpose); WO 00/12497 (discusses the relationship between p38 kinase inhibitors); and WO 00/12074 (piperazine and piperidine compounds useful as p38 inhibitors).

The present invention provides certain triazolopyridine compounds useful as kinase inhibitors, particularly p38 kinases.

SUMMARY OF THE INVENTION

The instant invention generally pertains to compounds of Formula I,

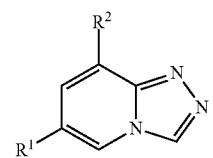

and enantiomers, diastereomers and pharmaceutically-acceptable salts thereof (particularly pharmaceutically-acceptable salts), wherein:

$R^1$ is an optionally substituted aryl or optionally substituted heteroaryl; and $R^2$ is hydrogen, optionally substituted lower alkyl, optionally substituted alkoxy, optionally substituted cycloalkoxy, optionally substituted aryloxy, optionally substituted arylamino, optionally substituted monocyclic aryl, optionally substituted heterocyclo, optionally substituted cycloalkyl or optionally substituted cycloalkenyl, with the provisos that:

(i) when $R^1$ is substituted thiazolyl, then the thiazolyl is not substituted with ethoxy; and (ii) when $R^2$ is substituted phenyl, then the phenyl is not substituted with trifluoromethyl or methylsulfonyl.

Listed below are definitions of various terms used to describe this invention. These definitions apply to the terms as they are used throughout this specification, unless otherwise limited in specific instances, either individually or as part of a larger group.

The term "acetyl" refers to the group —C(═O)CH$_3$.

The terms "alkyl" and "alk" refers to a straight or branched chain alkane (hydrocarbon) radical containing from 1 to 12 carbon atoms, preferably 1 to 6 carbon atoms. Exemplary groups include, but are not limited to, methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. The term "lower alkyl" is used herein to refer to those alkyl groups having from about 1 to about 6 carbon atoms and, more particularly, 1-4.

"Substituted alkyl" refers to an alkyl group substituted with one or more substituents, preferably 1 to 4 substituents, at any available point of attachment on the alkyl straight or branched chain. Exemplary substituents include one or more of the following groups: halo (e.g., a single halo substituent or multiple halo substituents forming, in the latter case, groups such as a perhaloalkyl group, such as an alkyl group bearing multiple chloro or multiple fluoro groups), nitro, cyano, hydroxy, alkoxy, haloalkoxy (e.g., trifluoromethoxy), —O-aryl, —O-heterocyclo, —O-alkylene-aryl, —O-haloalkyl, alkylthio, carboxy (i.e., —COOH), alkoxycarbonyl, alkylcarbonyloxy, carbamoyl, substituted carbamoyl, carbamate, substituted carbamate, urea, substituted urea, amidinyl, substituted amidinyl, aryl, heterocycle, cycloalkyl, —NR$^c$R$^d$, —OC (=O)NR$^c$R$^d$, —C(=O)NR$^c$R$^d$, —NR$^e$C(=O)NR$^c$R$^d$, —NR$^e$C(O)$^2$—NR$^c$R$^d$, —N(R$^e$)S(O)$_2$NR$^c$R$^d$, —N(R$^e$)P(O)$_2$NR$^c$R$^d$, (wherein each of R$^c$ and R$^d$ is independently selected from the group consisting of hydrogen, alkyl, aryl, and heterocyclo and R$^e$ is hydrogen, alkyl, or phenyl), —SR$^f$, —S(=O)R$^g$, —S(O)$_2$R$^g$, —NR$^e$S(O)$_2$—R$^g$, —P(O)$_2$—R$^g$, —NR$^e$P(O)$_2$—R$^g$, —NR$^e$C(=O)R$^f$, —NR$^e$C(O)$_2$R$^f$, —OC(=O)R$^f$, —OC(=O)OR$^f$, —C(=O)OR$^f$ and —C(=O)R$^f$ (wherein R$^e$ is defined as immediately above, R$^f$ is hydrogen, alkyl, aryl or heterocyclo, and R$^g$ is alkyl, aryl, or heterocyclo). In the aforementioned substituents, in each instance, the alkyl, aryl, heterocyclo or cycloalkyl groups (R$^c$, R$^d$, R$^e$, R$^f$, and R$^g$) in turn can be optionally substituted with one to four, preferably one to three further groups, selected from the group consisting of R$^k$, —O—R$^k$, cyano, nitro, haloalkyl, haloalkoxy, halo, —NR$^k$R$^m$, —OC(=O)NR$^k$R$^m$, —C(=O)NR$^k$R$^m$, —NR$^k$C(=O)R$^m$, —SR$^k$, —S(=O)R$^n$, —S(O)$_2$R$^n$, —OC(=O)R$^k$, —C(=O)OR$^k$, —C(=O)R$^k$, phenyl, benzyl, phenyloxy, or benzyloxy, and a lower alkyl substituted with one to two of —O—R$^k$, cyano, nitro, haloalkyl, haloalkoxy, halo, —NR$^k$R$^m$, —OC(=O)NR$^k$R$^m$, —C(=O)NR$^k$R$^m$, —NR$^k$C(=O)R$^m$, —SR$^k$, —S(=O)R$^n$, —S(O)$_2$R$^n$, —OC(=O)R$^k$, —C(=O)OR$^k$, —C(=O)R$^k$, phenyl, benzyl, phenyloxy, or benzyloxy, wherein R$^k$ and R$^m$ are selected from the group consisting of hydrogen, lower alkyl, hydroxy(lower alkyl), halo(lower alkyl), cyano(lower alkyl), and amino(lower alkyl), and R$^n$ is lower alkyl.

As used herein, "alkylene" refers to a bivalent alkyl radical having the general formula —(CH$_2$)$_n$—, where n is 1 to 10 (particularly 1-6 and, more particularly, 1-4). Non-limiting examples include methylene, dimethylene, trimethylene, tetramethylene, pentamethylene, and hexamethylene. The term "lower alkylene" herein refers to those alkylene groups having from about 1 to about 6 carbon atoms and, more particularly, 1-4. "Substituted alkylene" refers to an alkylene group substituted with one or more substituents, preferably 1 to 4 substituents, at any available point of attachment. Exemplary substituents include, but are not limited to alkyl, substituted alkyl, and those groups recited above as exemplary alkyl substituents.

When the term alkyl is used as a subscript following another particularly-named group, as in "arylalkyl," "substituted arylalkyl," "cycloalkylalkyl," etc., or as in hydroxy (lower alkyl), this refers to an alkyl group having one or two (preferably one) substituents selected from the other, particularly-named group. Thus, for example, arylalkyl includes benzyl and phenylethyl. A "substituted arylalkyl" will be substituted on the alkyl portion of the radical with one or more groups selected from those recited above for alkyl, and/or will be substituted on the aryl portion of the radical with one or more groups selected from those recited below for substituted aryl.

The term "alkenyl" refers to a straight or branched chain hydrocarbon radical containing from 2 to 12 carbon atoms and at least one carbon-carbon double bond. Exemplary groups include ethenyl or allyl. "Substituted alkenyl" refers to an alkenyl group substituted with one or more substituents, preferably 1 to 4 substituents, at any available point of attachment. Exemplary substituents on the alkenyl include, but are not limited to, alkyl, substituted alkyl, and those groups recited above as exemplary alkyl substituents. Particular examples of substituents for alkenyls are those selected from the group consisting of 2-6 carbons.

The term "alkenylene" refers to a straight or branched chain bivalent hydrocarbon radical containing from 2 to 12 carbon atoms and at least one carbon-carbon double bond. Exemplary groups include ethenylene or allylene. "Substituted alkenylene" refers to an alkenylene group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkenylenes are those selected from the group consisting of 2-6 carbons.

The term "alkynyl" refers to a straight or branched chain hydrocarbon radical containing from 2 to 12 carbon atoms and at least one carbon to carbon triple bond. Exemplary groups include ethynyl. "Substituted alkynyl" refers to an alkynyl group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkynyls are those selected from the group consisting of 2-6 carbons.

The term "alkynylene" refers to a straight or branched chain bivalent hydrocarbon radical containing from 2 to 12 carbon atoms and at least one carbon to carbon triple bond. Exemplary groups include ethynylene. "Substituted alkynylene" refers to an alkynylene group substituted with one or more substituents, preferably 1 to 4 substituents, at any available point of attachment. Exemplary substituents include, but are not limited to, alkyl, substituted alkyl, and those groups recited above as exemplary alkyl substituents. Particular examples of substituents for alkynylenes are those selected from the group consisting of 2-6 carbons.

The term "cycloalkyl" refers to a fully saturated cyclic hydrocarbon group containing from 1 to 3 rings and 3 to 8 carbons per ring. Exemplary groups include cyclopropyl, cyclobutyl, cyclopentyl, and cyclohexyl with a particular value being cyclopropyl. The term "cycloalkyl" also includes groups having a carbon-carbon bridge of one to two bridgehead carbon atoms, and bicyclic and tricyclic groups in which at least one of the rings is a saturated, carbon-containing ring, in which case the second or third ring may be carbocyclic or heterocyclic, provided that the point of attachment is to the cycloalkyl group. The further rings may be attached to the saturated, carbon-containing ring in a spiro or fused fashion. "Substituted cycloalkyl" refers to a cycloalkyl group substituted with one or more substituents, preferably 1 to 4 substituents, at any available point of attachment. Exemplary substituents include, but are not limited to, alkyl, substituted alkyl, oxo(=O), and those groups recited above as exemplary alkyl substituents.

The term "cycloalkylene" refers to a bivalent cycloalkyl group as defined above. Exemplary groups include cyclopropylene, cyclobutylene, cyclopentylene and cyclohexylene. "Substituted cycloalkylene" refers to a cycloalkylene group substituted with one or more substituents, preferably 1 to 4 substituents, at any available point of attachment selected from those recited for substituted cycloalkyl.

The term "cycloalkenyl" refers to a partially unsaturated cyclic hydrocarbon group containing 1 to 3 rings and 4 to 8 carbons per ring. Exemplary groups include cyclobutenyl, cyclopentenyl, and cyclohexenyl. The term "cycloalkenyl" also includes bicyclic and tricyclic groups in which at least one of the rings is a partially unsaturated, carbon-containing ring and the second or third ring may be carbocyclic or heterocyclic, provided that the point of attachment is to the cycloalkenyl group. "Substituted cycloalkenyl" refers to a cycloalkenyl group substituted with one or more substituents, preferably 1 to 4 substituents, at any available point of attachment selected from those recited above for cycloalkyl groups.

The term "cycloalkenylene" refers to a bivalent cycloalkenyl group, as defined above. Exemplary groups include cyclobutenylene, cyclopentenylene, and cyclohexenylene. "Substituted cycloalkenylene" refers to a cycloalkenylene group substituted with one or more substituents, preferably 1 to 4 substituents, at any available point of attachment, selected from those recited for substituted cycloalkyl.

The terms "alkoxy" or "alkylthio" refer to an alkyl group as described above bonded through an oxygen linkage (—O—) or a sulfur linkage (—S—), respectively. The terms "substituted alkoxy" or "substituted alkylthio" refer to a substituted alkyl group as described above bonded through an oxygen or sulfur linkage, respectively.

The term "cycloalkoxy" refers to a cycloalkyl group as described above bonded through an oxygen linkage (—O—). The term "substituted cycloalkoxy" refers to a substituted cycloalkyl group as described above bonded though an oxygen linkage.

The term "thiol" refers to —SH.

The term "alkoxycarbonyl" refers to an alkoxy group bonded through a carbonyl group (i.e., —C(=O)—O-alkyl). The term "substituted alkoxycarbonyl" refers to a substituted alkoxy group as described above bonded though a carbonyl group.

The term "alkoxycarbonyl methyl" refers to an alkoxycarbonyl group as described above bonded through a methyl group (i.e., —CH$_2$—C(=O)—O-alkyl). The term "substituted alkoxycarbonyl methyl" refers to a substituted alkoxycarbonyl group as described above bonded through a methyl group.

The term "alkylcarbonyl" refers to an alkyl group bonded through a carbonyl group (i.e., —C(=O)alkyl).

The term "alkylcarbonyloxy" refers to an alkylcarbonyl group bonded through an oxygen linkage (i.e., —O—C(=O)-alkyl).

The term "amido" refers to the group —NHC(=O)H, and "amidinyl" refers to the group —C(=NH)(NH$_2$). A "substituted amido" refers to the group —NR$^p$C(=O)R$^q$, and a "substituted amidinyl" refers to the group —C(=NR$^p$)(NR$^q$R$^r$), wherein R$^p$, R$^q$, and R$^r$ are selected from hydrogen, alkyl, substituted alkyl, cycloalkyl, substituted cycloalkyl, aryl, substituted aryl, heterocyclo, and substituted heterocyclo, provided that at least one of R$^p$, R$^q$, and R$^r$ is other than hydrogen. A more particular value for R$^p$, R$^q$ and R$^r$ is selected from the group consisting of hydrogen or alkyl.

The term "aryl" encompasses monocyclic and polycyclic aryl groups which contain only carbons on the first ring. The term "monocyclic aryl" refers to phenyl (where the ring only contains carbons), and the term "polycyclic aryl" refers to napthyl and anthracenyl, to phenyl rings having at least a second ring fused thereto, and to napthyl rings having a third ring fused thereto. In the case of a polycyclic aryl consisting of a phenyl ring having a second or third ring fused thereto, or a napthyl ring having a third ring fused thereto, the additional rings may be aromatic or non-aromatic carbocyclic or heterocyclic rings, provided that in such cases the point of attachment will be to the carbocyclic aromatic ring. For example, a subset of this aryl group is a polycyclic aryl group wherein the second ring is a "heteroaryl" which contains carbon atoms and at least one heteroatom selected from the group consisting of O, N, and S (provided that O and S cannot be adjacent to each other in the same ring). Alternatively, a ring carbon atom of the second and/or third further rings may be replaced with a carbonyl [—C(=O)group](e.g., when such rings are non-aromatic). "Substituted aryl" refers to an aryl group substituted by one or more substituents, preferably 1 to 4 substituents (more preferably 1 or 2), at any point of attachment of any ring, selected from alkyl, substituted alkyl, and the substituents recited above for substituted alkyl groups.

Accordingly, examples of aryl groups that are of interest in forming compounds of the invention include:

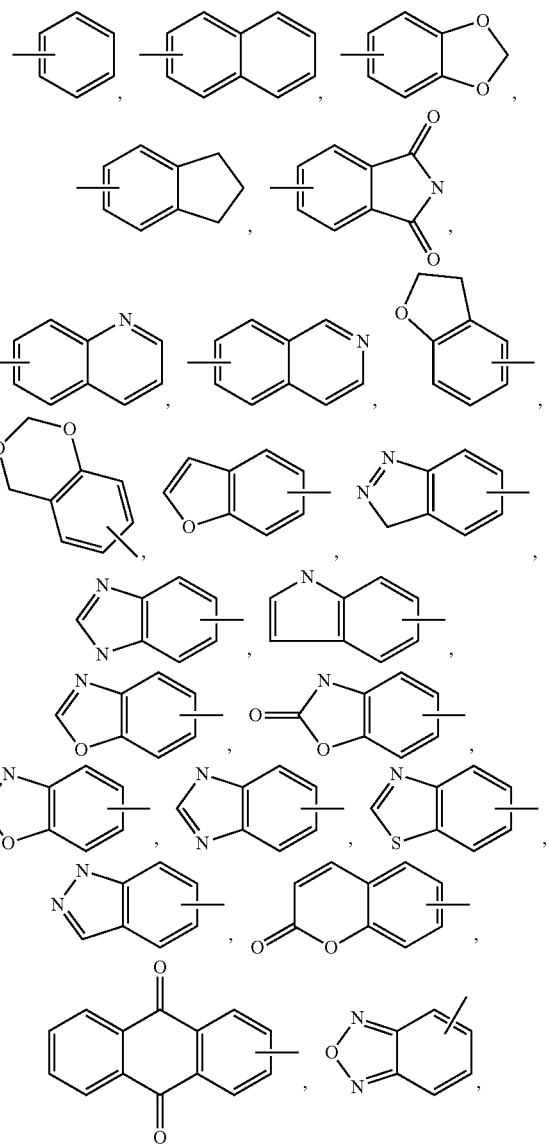

and, additionally, similar structures.

The term "arylene" refers to bivalent aryl groups as defined above.

The term "arylamino" refers to an aryl group as described above bonded through an amino group. The term "substituted arylamino" refers to a substituted aryl group as described above bonded through an amino group.

The term "aryloxy" refers to an aryl group as described above bonded through an oxygen linkage (—O—). The term "substituted aryloxy" refers to a substituted aryl group as described above bonded though an oxygen linkage.

"Carbamoyl" refers to the group —C(=O)—NR$^h$R$^i$, wherein R$^h$ and R$^i$ are independently selected from hydrogen, alkyl, cycloalkyl, aryl, and heterocyclo.

The term "carbamoylmethyl" refers to a carbamoyl group as described above bonded through a methyl group (i.e., —CH$_2$—C(=O)—NR$^h$R$^i$, wherein R$^h$ and R$^i$ are defined above).

"Carbamate" refers to the group —O—C(=O)—NR$^h$R$^i$, and "urea" refers to the groups NH—C(=O)—NR$^h$R$^i$ and N(alkyl)-C(=O)—NR$^h$R$^i$, wherein R$^h$ and R$^i$ are selected from the same groups recited for carbamoyl.

"Substituted carbamoyl", "substituted carbamate", and "substituted urea" refer to the groups —C(=O)—NR$^h$R$^i$, —O—C(=O)—NR$^h$R$^i$, and —N(R$^j$)—C(=O)—NR$^h$R$^i$, respectively, wherein R$^h$, R$^i$, and R$^j$ are selected from hydrogen, alkyl, substituted alkyl, cycloalkyl, substituted cycloalkyl, aryl, substituted aryl, heterocyclo, and substituted heterocyclo, provided that at least one of R$^h$, R$^i$, and R$^j$ is substituted alkyl, substituted cycloalkyl, substituted aryl, or substituted heterocyclo. "N-substituted carbamoylmethyl" refers to the group —CH$_2$—C(=O)—NR$^h$R$^i$, wherein R$^h$ and R$^i$ are selected from hydrogen, alkyl, substituted alkyl, cycloalkyl, substituted cycloalkyl, aryl, substituted aryl, heterocyclo, and substituted heterocyclo, provided that at least one of R$^h$ and R$^i$ is substituted alkyl, substituted cycloalkyl, substituted aryl, or substituted heterocyclo.

The term "carboxyl" refers to the group —C(=O)OH.

The terms "heterocycle", "heterocyclic" and "heterocyclo" refer to fully saturated, partially unsaturated, or fully unsaturated, including aromatic (i.e., "heteroaryl") cyclic groups (for example, 3 to 7 membered monocyclic, 7 to 11 membered bicyclic, or 10 to 16 membered tricyclic ring systems) which have at least one heteroatom in at least one carbon atom-containing ring. Thus, the term "heteroaryl" is a subset of heterocyclo groups. Each ring of the heterocyclic group containing a heteroatom may have 1, 2, 3, or 4 heteroatoms selected from nitrogen atoms, oxygen atoms and/or sulfur atoms, where the nitrogen and sulfur heteroatoms may optionally be oxidized and the nitrogen heteroatoms may optionally be quaternized, provided sulfur and oxygen are not adjacent to each other in the ring. (The term "heteroarylium" refers to a heteroaryl group bearing a quaternary nitrogen atom and thus a positive charge.) Additionally, one or more (preferably one) carbon ring atoms of the heterocyclo ring may, as valence allows, be replaced with carbonyl group, i.e., —C(=O)—. The heterocyclic group may be attached to the remainder of the molecule at any heteroatom or carbon atom of the ring or ring system.

Exemplary monocyclic heterocyclic groups include those selected from the group consisting of oxiranyl, azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolidinyl, 2-oxoazepinyl, azepinyl, hexahydrodiazepinyl, 4-piperidonyl, pyridyl, pyrazinyl, pyrimidinyl, pyridazinyl, triazinyl, triazolyl, tetrazolyl, tetrahydropyranyl, morpholinyl, thiamorpholinyl, thiamorpholinyl sulfoxide, thiamorpholinyl sulfone, 1,3-dioxolanyl and tetrahydro-1,1-dioxothienyl, and the like.

Exemplary bicyclic heterocyclic groups include those selected from the group consisting of indolyl, isoindolyl, benzothiazolyl, benzodioxolyl, benzoxazolyl, benzoxadiazolyl, benzothienyl, quinuclidinyl, quinolinyl, tetrahydroisoquinolinyl, isoquinolinyl, benzimidazolyl, benzopyranyl, indolizinyl, benzofuryl, benzofurazanyl, chromonyl, coumarinyl, benzopyranyl, cinnolinyl, quinoxalinyl, indazolyl, pyrrolopyridyl, furopyridinyl (such as furo[2,3-c]pyridinyl, furo[3,2-b]pyridinyl] or furo[2,3-b]pyridinyl), dihydrobenzodioxinyl, dihydrodioxidobenzothiophenyl, dihydroisoindolyl, dihydroindolyl, dihydroquinolinyl, dihydroquinazolinyl (such as 3,4-dihydro-4-oxo-quinazolinyl), triazinylazepinyl, tetrahydroquinolinyl and the like. Exemplary tricyclic heterocyclic groups include carbazolyl, benzidolyl, phenanthrolinyl, dibenzofuranyl, acridinyl, phenanthridinyl, xanthenyl and the like.

The term "heterocyclene" refers to bivalent heterocycle groups as defined above.

"Substituted heterocycle", "substituted heterocyclic" and "substituted heterocyclo" (such as "substituted heteroaryl") refer to heterocycle, heterocyclic or heterocyclo groups substituted with one or more substituents, preferably 1 to 4 substituents, at any available point of attachment, wherein the substituents are selected from those recited above for substituted cycloalkyl groups.

The term "quaternary nitrogen" refers to a tetravalent positively charged nitrogen atom including, for example, the positively charged nitrogen in a tetraalkylammonium group (e.g., tetramethylammonium, N-methylpyridinium), the positively charged nitrogen in protonated ammonium species (e.g., trimethyl-hydroammonium, N-hydropyridinium), the positively charged nitrogen in amine N-oxides (e.g., N-methyl-morpholine-N-oxide, pyridine-N-oxide), and the positively charged nitrogen in an N-amino-ammonium group (e.g., N-aminopyridinium).

The term "heteroaryl" refers to five and six membered monocyclic aromatic heterocyclo groups, as well as bicyclic and tricyclic heterocyclic ring systems in which the point of attachment of the ring system to another group is via a five or six membered aromatic ring of the ring system. Thus, for example, the term heteroaryl includes groups such as five or six membered heteroaryl groups, such as thienyl, pyrrolyl, oxazolyl, pyridyl, pyrazinyl, and the like, wherein fused rings completing bicyclic and tricyclic groups may contain only carbon atoms and may be saturated, partially saturated, or unsaturated. Heteroaryl groups which are bicyclic or tricyclic must include at least one fully aromatic ring but the other fused ring or rings may be aromatic or non-aromatic.

The term "substituted heteroaryl" refers to five and six membered monocyclic aromatic heterocyclo groups substituted with one or more substituents, such as 1 to 4 substituents (more particularly 1-3 substituents and, even more particularly, 1-2 substituents), at any available point of attachment, wherein the substituents are selected from those recited above for substituted cycloalkyl groups.

Exemplary monocyclic heteroaryl groups include those selected from the group consisting of pyrrolyl, pyrazolyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, and the like.

Exemplary bicyclic heteroaryl groups include those selected from the group consisting of indolyl, benzothiazolyl, benzodioxolyl, benzoxazolyl, benzothienyl, quinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, and the like.

Exemplary tricyclic heteroaryl groups include carbazolyl, benzidolyl, phenanthrolinyl, acridinyl, phenanthridinyl, xanthenyl and the like.

The terms "hydroxylamine" and "hydroxylamide" refer to the groups —NH—OH and —C(=O)—NH—OH, respectively.

Unless otherwise indicated, the term "substituted amino" as employed herein alone or as part of another group refers to amino substituted with one or two substituents, which may be the same or different, such as alkyl, aryl, arylalkyl, heterocyclo, heteroaryl, heteroarylalkyl, cycloheteroalkyl, cycloheteroalkylalkyl, cycloalkyl, cycloalkylalkyl, haloalkyl, hydroxyalkyl, alkoxyalkyl, thioalkyl, —C(O)R$^t$, —C(=O)OR$^t$, —C(=O)NR$^t$R$^u$, —S(O)$_2$R$^t$, —S(O)$_2$OR$^t$, or —S(O)$_2$NR$^t$R$^u$, wherein R$^t$ and R$^u$ are each independently selected from the group consisting of hydrogen, alkyl, substituted alkyl, aryl, substituted aryl or heterocyclo. These substituents may be further substituted with a carboxylic acid and/or any of the substituents for alkyl as set out above.

Also, R$^t$ and R$^u$ may be taken together with the nitrogen atom to which they are attached to form 1-pyrrolidinyl, 1-piperidinyl, 1-azepinyl, 4-morpholinyl, 4-thiamorpholinyl, 1-piperazinyl, 4-alkyl-1-piperazinyl, 4-arylalkyl-1-piperazinyl, 4-diarylalkyl-1-piperazinyl, 1-pyrrolidinyl, 1-piperidinyl, or 1-azepinyl, optionally substituted with alkyl, aryl, heterocyclo, alkoxy, alkylthio, halo, trifluoromethyl, hydroxy, amino, —C(O)R$^f$, —C(=O)OR$^f$, —C(=O)NR$^f$R$^g$, —S(O)$_2$R$^f$, —S(O)$_2$OR$^f$, or —S(O)$_2$NR$^f$R$^g$, wherein R$^f$ and R$^g$ can be hydrogen, alkyl, substituted alkyl, aryl, substituted aryl or heterocyclo.

The term "heteroatoms" shall include oxygen, sulfur and nitrogen.

The terms "halogen" or "halo" refer to chlorine, bromine, fluorine or iodine.

The term "haloalkyl" means an alkyl having one or more halo substituents, particularly when the alkyl portion is selected from the group consisting of $C_1$-$C_3$. For example, haloalkyl can be $CF_3$.

The term "haloalkoxy" means an alkoxy group having one or more halo substituents, particularly when the alkoxy portion comprises $C_1$-$C_3$. For example, "haloalkoxy" includes —OCF$_3$.

The term "lower alkyl sulfonyl" refers to a lower alkyl group as described above bonded through a sulfonyl linkage (—S(=O)(=O)—). The term "substituted lower alkyl sulfonyl" refers to a substituted alkyl group as described above bonded through a sulfonyl linkage.

The term "carbocyclic" means a saturated or unsaturated monocyclic or bicyclic ring in which all atoms of all rings are carbon. Thus, the term includes cycloalkyl and aryl rings. The carbocyclic ring may be substituted, in which case the substituents are selected from those recited above for cycloalkyl and aryl groups.

When the term "unsaturated" is used herein to refer to a ring or group, the ring or group may be fully unsaturated or partially unsaturated.

When it is stated that a group may be "optionally substituted," this is intended to include unsubstituted groups and substituted groups wherein the substituents are selected from those recited above for the particularly named group. Thus, when reference is made to an optionally substituted aryl, it is intended to refer to unsubstituted aryl groups, such as phenyl or naphthyl, and such groups having one or more (preferably 1 to 4, and more preferably 1 or 2) substituents selected from alkyl, substituted alkyl, and those substituents recited for substituted alkyl groups. When the term "optionally substituted" precedes a Markush group, the term "optionally substituted" is intended to modify each one of the species recited in the Markush group. Thus, for example, the phrase "optionally substituted aryl, cycloalkyl, or heterocycle" includes aryl, substituted aryl, cycloalkyl, substituted cycloalkyl, heterocycle, and substituted heterocycle.

Among the compounds of the invention, in the case of a compound which has a sulfide, the sulfur atom may be converted into oxido at an appropriate oxidation state, and all of these oxido derivatives are included herein.

"N-oxide" refers to compounds wherein the basic nitrogen atom of either a heteroaromatic ring or tertiary amine is oxidized to give a quaternary nitrogen bearing a positive formal charge and an attached oxygen atom bearing a negative formal charge.

"Solvate" refers to a molecular or ionic complex of molecules or ions of solvent with molecules or ions of solute. It should further be understood that solvates (e.g., hydrates) of the compounds of Formula I are also within the scope of the present invention. Methods of solvation are generally known in the art.

When a functional group is termed "protected", this means that the group is in modified form to mitigate, especially preclude, undesired side reactions at the protected site. Suitable protecting groups for the methods and compounds described herein include, without limitation, those described in standard textbooks, such as Greene, T. W. et al., *Protective Groups in Organic Synthesis*, Wiley, N.Y. (1991), incorporated by reference as to the listing of such protective groups.

Unless otherwise indicated, any carbon atom or heteroatom with unsatisfied valences is assumed to have hydrogen atoms sufficient to satisfy the valences.

Carboxylate anion refers to a negatively charged group —COO$^-$.

The present invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds have a variety of potential uses, e.g., as standards and reagents in determining the ability of a potential pharmaceutical compound to bind to target proteins or receptors, or for imaging compounds of this invention bound to biological receptors in vivo or in vitro.

The compounds of the present invention may form salts which are also within the scope of this invention. Pharmaceutically acceptable (i.e., non-toxic, physiologically acceptable) salts are preferred, although other salts are also useful, e.g., in isolating or purifying the compounds of this invention.

The compounds of the present invention may form salts with alkali metals such as sodium, potassium, and lithium; with alkaline earth metals such as calcium and magnesium; and with organic bases such as dicyclohexylamine, tributylamine, pyridine, and amino acids such as arginine, lysine, and the like. Such salts can be formed as known to those skilled in the art.

The compounds of the present invention may form salts with a variety of organic and inorganic acids. Such salts include those formed with hydrogen chloride, hydrogen bromide, methanesulfonic acid, sulfuric acid, acetic acid, trifluoroacetic acid, oxalic acid, maleic acid, benzenesulfonic acid, toluenesulfonic acid, and various others (e.g., nitrates, phosphates, borates, tartrates, citrates, succinates, benzoates, ascorbates, salicylates, and the like). Such salts can be formed as known to those skilled in the art. Salt forms of the compounds may be advantageous for improving the compound dissolution rate and oral bioavailability.

In addition, zwitterions ("inner salts") may be formed.

All stereoisomers of the compounds of the instant invention are contemplated, either in admixture or in pure or substantially pure form. The definition of compounds according to the invention embraces all the possible stereoisomers and their mixtures; it also embraces the racemic forms and the isolated optical isomers having the specified activity. The racemic forms can be resolved by physical methods, such as, for example, fractional crystallization, separation, or crystallization of diastereomeric derivatives or separation by chiral column chromatography. The individual optical isomers can be obtained from the racemates from the conventional methods, such as, for example, salt formation with an optically active acid followed by crystallization.

Compounds of the present invention may also have prodrug forms. Any compound that will be converted in vivo to provide the bioactive agent (i.e., the compound for Formula I) is a prodrug within the scope and spirit of the invention.

Various forms of prodrugs are well known in the art. For examples of such prodrug derivatives, see:

a) *Design of Prodrugs*, H. Bundgaard, ed., Elsevier (1985), and *Methods in Enzymology*, 112:309-396, K. Widder et al., eds., Academic Press (1985);

b) Bundgaard, H., Chapter 5, "Design and Application of Prodrugs," *A Textbook of Drug Design and Development*, pp. 113-191, P. Krosgaard-Larsen et al., eds., Harwood Academic Publishers (1991); and c) Bundgaard, H., *Adv. Drug Deliv. Rev.*, 8:1-38 (1992)), each of which is incorporated herein by reference.

DETAILED DESCRIPTION OF THE INVENTION

One embodiment of the present invention relates to a compound of Formula I

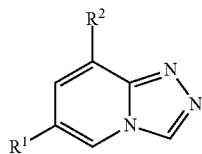

I and enantiomers, diastereomers and pharmaceutically-acceptable salts thereof, wherein:

$R^1$ is selected from the group consisting of optionally substituted aryl and optionally substituted heteroaryl; and $R^2$ is selected from the group consisting of hydrogen, optionally substituted lower alkyl, optionally substituted alkoxy, optionally substituted cycloalkoxy, optionally substituted aryloxy, optionally substituted arylamino, optionally substituted monocyclic aryl, optionally substituted heterocyclo, optionally substituted cycloalkyl and optionally substituted cycloalkenyl, with the provisos that:

(i) when $R^1$ is substituted thiazolyl, then the thiazolyl is not substituted with ethoxy; and (ii) when $R^2$ is substituted phenyl, then the phenyl is not substituted with trifluoromethyl or methylsulfonyl.

In another particular embodiment, $R^1$ is optionally substituted thiazolyl.

Another embodiment of the present invention relates to a compound of Formula I

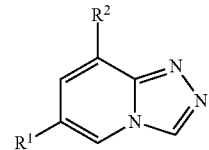

I and enantiomers, diastereomers and pharmaceutically-acceptable salts thereof, wherein:

$R^1$ is optionally substituted thiazolyl; and $R^2$ is selected from the group consisting of hydrogen, optionally substituted lower alkyl, optionally substituted alkoxy, optionally substituted cycloalkoxy, optionally substituted aryloxy, optionally substituted arylamino, optionally substituted monocyclic aryl, optionally substituted heterocyclo, optionally substituted cycloalkyl and optionally substituted cycloalkenyl, with the provisos that:

(i) when $R^1$ is substituted thiazolyl, then the thiazolyl is not substituted with ethoxy; and (ii) when $R^2$ is substituted phenyl, then the phenyl is not substituted with trifluoromethyl or methylsulfonyl.

In a particular embodiment when $R^1$ is optionally substituted thiazolyl, the thiazolyl is substituted at a carbon atom with a substituent selected from the group consisting of optionally substituted lower alkyl, optionally substituted alkylthio, optionally substituted alkenyl, optionally substituted alkynyl, hydroxy, cyano, optionally substituted aryl, optionally substituted heterocyclo, optionally substituted cycloalkyl, optionally substituted cycloalkenyl, optionally substituted thiol, optionally substituted alkoxycarbonyl, optionally substituted alkylcarbonyl, optionally substituted alkylcarbonyloxy, optionally substituted amino, optionally substituted amido, optionally substituted amidinyl, optionally substituted carbamoyl, optionally substituted carbamate, optionally substituted urea, optionally substituted hydroxylamine, optionally substituted hydroxylamide, halo, haloalkyl and haloalkoxy.

A yet more particular value for $R^1$ is thiazol-5-yl. In a particular embodiment when the value for $R^1$ is thiazol-5-yl, the thiazol-5-yl is substituted at the 2 position with a substituent selected from the group consisting of optionally substituted lower alkyl, optionally substituted alkylthio, optionally substituted alkenyl, optionally substituted alkynyl, hydroxy, cyano, optionally substituted aryl, optionally substituted heterocyclo, optionally substituted cycloalkyl, optionally substituted cycloalkenyl, optionally substituted thiol, optionally substituted alkoxycarbonyl, optionally substituted alkylcarbonyl, optionally substituted alkylcarbonyloxy, optionally substituted amino, optionally substituted amido, optionally substituted amidinyl, optionally substituted carbamoyl, optionally substituted carbamate, optionally substituted urea, optionally substituted hydroxylamine, optionally substituted hydroxylamide, halo, haloalkyl and haloalkoxy.

In yet another particular embodiment when the value for $R^1$ is thiazol-5-yl, the thiazol-5-yl is substituted at the 2 position with optionally substituted amino.

In yet a more particular embodiment when the value for $R^1$ is thiazol-5-yl, the thiazol-5-yl is substituted at the 2 position with lower alkyl amino.

Even more particular values of $R^1$ are found in the compounds set forth in the Examples, such as the compounds listed in Table 1. For example, $R^1$ may be selected from the group consisting of:

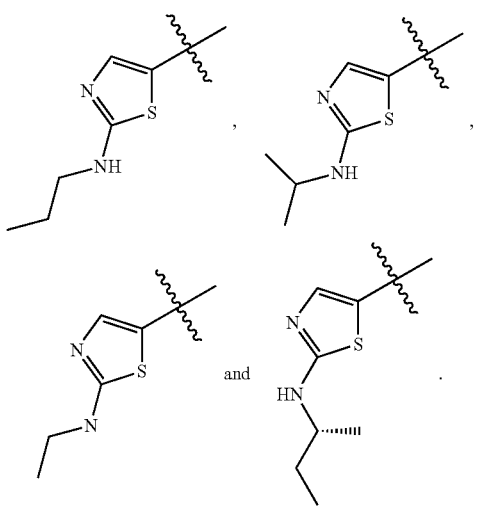

In another particular embodiment, $R^2$ is selected from the group consisting of hydrogen and optionally substituted monocyclic aryl.

A more particular value for $R^2$ is optionally substituted phenyl.

Another more particular value for $R^2$ is unsubstituted phenyl.

Yet another more particular value for $R^2$ is substituted phenyl.

When $R^2$ is phenyl, the phenyl may be optionally substituted independently at one or more position with substituents selected from the group consisting of optionally substituted lower alkyl, optionally substituted alkoxy, optionally substituted alkylthio, optionally substituted alkenyl, optionally substituted alkynyl, hydroxy, cyano, optionally substituted aryl, optionally substituted heterocyclo, optionally substituted cycloalkyl, optionally substituted cycloalkenyl, optionally substituted thiol, optionally substituted alkoxycarbonyl, optionally substituted alkylcarbonyl, optionally substituted alkylcarbonyloxy, optionally substituted amino, optionally substituted amido, optionally substituted amidinyl, optionally substituted carbamoyl, optionally substituted carbamate, optionally substituted urea, optionally substituted hydroxylamine, optionally substituted hydroxylamide, halo and haloalkoxy.

When $R^2$ is phenyl, the phenyl is more particularly optionally substituted independently at one or more position with substituents selected from the group consisting of halo, cyano, $C_1$-$C_4$ alkyl and hydroxy.

When $R^2$ is phenyl, the phenyl is even more particularly optionally substituted independently at one or more position with substituents selected from the group consisting of halo, cyano, methyl and hydroxy.

In another particular embodiment, $R^1$ is optionally substituted thiazolyl and $R^2$ is optionally substituted phenyl.

In yet another particular embodiment, $R^1$ is lower alkyl amino thiazolyl and $R^2$ is phenyl substituted with a halo group.

In another embodiment, the instant invention is directed to a pharmaceutical composition comprising at least one compound according to Formula I (including all of the subgroups and particular groups described above) and a pharmaceutically-acceptable carrier or diluent.

In a more particular embodiment, the pharmaceutical composition is a solid dosage form.

Other embodiments of the present invention are 1) a method of treating a disease or disorder comprising administering to a patient in need of treatment a therapeutically effective amount of a compound of Formula I, 2) a compound of Formula I for use in treating a disease or disorder, and 3) use of a compound of Formula I in the manufacture of a medicament for treatment of a disease or disorder; wherein the disease or disorder is an inflammatory disorder.

In a further embodiment, the aforementioned inflammatory disorder is selected from the group consisting of rheumatoid arthritis, asthma, acute respiratory distress syndrome, chronic obstructive pulmonary disease, chronic pulmonary inflammatory disease, inflammatory bowel disease, osteoporosis, psoriasis, graft vs. host rejection, atherosclerosis, multiple myeloma, multiple sclerosis, pain, myocardial ischemia and arthritis. More particularly, the disorder is selected from the group consisting of psoriasis, atherosclerosis, pain, and rheumatoid arthritis.

In yet another embodiment, the present invention is directed to a method of inhibiting p38 kinase in a patient in need of such treatment comprising administering to the patient a therapeutically effective amount of a compound of Formula I (including all of the subgroups and particular groups described above).

The invention may be embodied in other specific forms without departing from the spirit or essential attributes thereof. This invention also encompasses all combinations of alternative aspects and embodiments of the invention noted herein. It is understood that any and all embodiments may be taken in conjunction with any other embodiment to describe additional embodiments of the present invention. Furthermore, any elements of an embodiment are meant to be combined with any and all other elements from any of the embodiments to describe additional embodiments.

Utility

The compounds of the invention are selective inhibitors of p38 kinase activity. Accordingly, compounds of Formula I have utility in treating conditions associated with p38 kinase activity. Such conditions include diseases in which cytokine levels are modulated as a consequence of intracellular signaling via p38, and in particular, diseases that are associated with an overproduction of cytokines IL-1, IL-4, IL-8, and TNF-α. As used herein, the terms "treating" or "treatment" encompass either or both responsive and prophylaxis measures, e.g., measures designed to inhibit or delay the onset of the disease or disorder, achieve a full or partial reduction of the symptoms or disease state, and/or to alleviate, ameliorate, lessen, or cure the disease or disorder and/or its symptoms.

In view of their activity as inhibitors of p-38 kinase, compounds of Formula I are useful in treating p-38 associated conditions including, but not limited to, inflammatory diseases, autoimmune diseases, destructive bone disorders, proliferative disorders, angiogenic disorders, infectious diseases, neurodegenerative diseases, and viral diseases.

More particularly, the specific conditions or diseases that may be treated with the inventive compounds include, without limitation, pancreatitis (acute or chronic), asthma, allergies, acute respiratory distress syndrome, chronic obstructive pulmonary disease, glomerulonephritis, rheumatoid arthritis, systemic lupus erythematosis, scleroderma, chronic thyroiditis, Graves' disease, autoimmune gastritis, diabetes, autoimmune hemolytic anemia, autoimmune neutropenia, thrombocytopenia, atopic dermatitis, chronic active hepatitis, myasthenia gravis, multiple sclerosis, inflammatory bowel disease, ulcerative colitis, Crohn's disease, psoriasis, graft vs.

host disease, inflammatory reaction induced by endotoxin, tuberculosis, atherosclerosis, muscle degeneration, cachexia, psoriatic arthritis, Reiter's syndrome, gout, traumatic arthritis, rubella arthritis, acute synovitis, pancreatic β-cell disease; diseases characterized by massive neutrophil infiltration; rheumatoid spondylitis, gouty arthritis and other arthritic conditions, cerebral malaria, chronic pulmonary inflammatory disease, silicosis, pulmonary sarcoidosis, bone resorption disease, allograft rejections, fever and myalgias due to infection, cachexia secondary to infection, meloid formation, scar tissue formation, ulcerative colitis, pyresis, influenza, osteoporosis, osteoarthritis and multiple myeloma-related bone disorder, acute myelogenous leukemia, chronic myelogenous leukemia, metastatic melanoma, Kaposi's sarcoma, multiple myeloma, sepsis, septic shock, and Shigellosis; Alzheimer's disease, Parkinson's disease, cerebral ischemias or neurodegenerative disease caused by traumatic injury; angiogenic disorders including solid tumors, ocular neovasculization, and infantile haemangiomas; viral diseases including acute hepatitis infection (including hepatitis A, hepatitis B and hepatitis C), HIV infection and CMV retinitis, AIDS, ARC or malignancy, and herpes; stroke, myocardial ischemia, ischemia in stroke heart attacks, organ hyposia, vascular hyperplasia, cardiac and renal reperfusion injury, thrombosis, cardiac hypertrophy, thrombin-induced platelet aggregation, endotoxemia and/or toxic shock syndrome, and conditions associated with prostaglandin endoperoxidase syndase-2.

In addition, p38 inhibitors of this invention inhibit the expression of inducible pro-inflammatory proteins such as prostaglandin endoperoxide synthase-2 (PGHS-2), also referred to as cyclooxygenase-2 (COX-2). Accordingly, additional p38-associated conditions include edema, analgesia, fever and pain, such as neuromuscular pain, headache, pain caused by cancer, dental pain and arthritis pain. The inventive compounds also may be used to treat veterinary viral infections, such as lentivirus infections, including, but not limited to equine infectious anemia virus; or retro virus infections, including feline immunodeficiency virus, bovine immunodeficiency virus, and canine immunodeficiency virus.

When the terms "p38 associated condition" or "p38 associated disease or disorder" are used herein, each is intended to encompass all of the conditions identified above as if repeated at length, as well as any other condition that is affected by p38 kinase activity.

Particular examples of diseases that would benefit from p38 inhibitors are rheumatoid arthritis, asthma, adult respiratory distress syndrome, chronic obstructive pulmonary disease, chronic pulmonary inflammatory disease, diabetes, inflammatory bowel disease, ulcerative colitis, Crohn's disease, osteoporosis, psoriasis, graft vs. host rejection, atherosclerosis, acute coronary disease, multiple myeloma, multiple sclerosis, acute myelogenous leukemia, chronic myelogenous leukemia, pain, myocardial ischemia and arthritis including rheumatoid arthritis, psoriatic arthritis, traumatic arthritis, rubella arthritis, gouty arthritis and osteoarthritis. Even more particular examples include disorders selected from the group consisting of rheumatoid arthritis, asthma, acute respiratory distress syndrome, chronic obstructive pulmonary disease, chronic pulmonary inflammatory disease, inflammatory bowel disease, osteoporosis, psoriasis, graft vs. host rejection, atherosclerosis, multiple myeloma, multiple sclerosis, pain, myocardial ischemia and arthritis, especially those disorders selected from the group consisting of psoriasis, atherosclerosis, pain, and rheumatoid arthritis.

The present invention thus provides methods for treating such conditions, comprising administering to a subject in need thereof an effective amount of at least one compound of Formula I or a salt thereof. The methods of treating p38 kinase-associated conditions may comprise administering compounds of Formula I alone or in combination with other suitable therapeutic agents useful in treating such conditions. Exemplary of such other therapeutic agents include corticosteroids, rolipram, calphostin, CSAIDs, 4-substituted imidazo[1,2-A]quinoxalines as disclosed in U.S. Pat. No. 4,200,750; Interleukin-10, glucocorticoids, salicylates, nitric oxide, and other immunosuppressants; nuclear translocation inhibitors, such as deoxyspergualin (DSG); non-steroidal antiinflammatory drugs (NSAIDs) such as ibuprofen, celecoxib and rofecoxib; steroids such as prednisone or dexamethasone; antiviral agents such as abacavir; antiproliferative agents such as methotrexate, leflunomide, FK506 (tacrolimus, PROGRAF®); cytotoxic drugs such as azathiprine and cyclophosphamide; TNF-α inhibitors such as tenidap, anti-TNF antibodies or soluble TNF receptor, and rapamycin (sirolimus or RAPAMUNE®) or derivatives thereof.

The above other therapeutic agents, when employed in combination with the compounds of the present invention, may be used, for example, in those amounts indicated in the Physicians' Desk Reference (PDR) or as otherwise determined by one of ordinary skill in the art. In the methods of the present invention, such other therapeutic agent(s) may be administered prior to, simultaneously with, or following the administration of the inventive compounds.

The present invention also provides pharmaceutical compositions capable of treating p38-kinase associated conditions, including TNF-α, IL-1, and/or IL-8 mediated conditions, as described above. The inventive compositions may contain other therapeutic agents as described above and may be formulated, for example, by employing conventional solid or liquid vehicles or diluents, as well as pharmaceutical additives of a type appropriate to the mode of desired administration (e.g., excipients, binders, preservatives, stabilizers, flavors, etc.) according to techniques such as those well known in the art of pharmaceutical formulation.

The compounds of Formula I may be administered by any means suitable for the condition to be treated, which may depend on the need for site-specific treatment or quantity of drug to be delivered. Topical administration is generally preferred for skin-related diseases, and systematic treatment preferred for cancerous or pre-cancerous conditions, although other modes of delivery are contemplated. For example, the compounds may be delivered orally, such as in the form of tablets, capsules, granules, powders, or liquid formulations including syrups; topically, such as in the form of solutions, suspensions, gels or ointments; sublingually; bucally; parenterally, such as by subcutaneous, intravenous, intramuscular or intrasternal injection or infusion techniques (e.g., as sterile injectable aq. or non-aq. solutions or suspensions); nasally such as by inhalation spray; topically, such as in the form of a cream or ointment; rectally such as in the form of suppositories; or liposomally. Dosage unit formulations containing non-toxic, pharmaceutically acceptable vehicles or diluents may be administered. The compounds may be administered in a form suitable for immediate release or extended release. Immediate release or extended release may be achieved with suitable pharmaceutical compositions or, particularly in the case of extended release, with devices such as subcutaneous implants or osmotic pumps.

Exemplary compositions for topical administration include a topical carrier such as Plastibase (mineral oil gelled with polyethylene).

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The inventive compounds may also be orally delivered by sublingual and/or buccal administration, e.g., with molded, compressed, or freeze-dried tablets. Exemplary compositions may include fast-dissolving diluents such as mannitol, lactose, sucrose, and/or cyclodextrins. Also included in such formulations may be high molecular weight excipients such as celluloses (AVICEL®) or polyethylene glycols (PEG); an excipient to aid mucosal adhesion such as hydroxypropyl cellulose (HPC), hydroxypropyl methyl cellulose (HPMC), sodium carboxymethyl cellulose (SCMC), and/or maleic anhydride copolymer (e.g., Gantrez); and agents to control release such as polyacrylic copolymer (e.g., Carbopol 934). Lubricants, glidants, flavors, coloring agents and stabilizers may also be added for ease of fabrication and use.

Exemplary compositions for nasal aerosol or inhalation administration include solutions which may contain, for example, benzyl alcohol or other suitable preservatives, absorption promoters to enhance absorption and/or bioavailability, and/or other solubilizing or dispersing agents such as those known in the art.

Exemplary compositions for parenteral administration include injectable solutions or suspensions which may contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, suitable non-irritating excipients, such as cocoa butter, synthetic glyceride esters or polyethylene glycols, which are solid at ordinary temperatures but liquefy and/or dissolve in the rectal cavity to release the drug.

The effective amount of a compound of the present invention may be determined by one of ordinary skill in the art, and includes exemplary dosage amounts for a mammal of from about 0.05 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats, horses, and the like. Thus, when the term "patient" is used herein, this term is intended to include all subjects, most preferably mammalian species, that are affected by mediation of p38 enzyme levels.

Compounds described in the examples infra, have been tested in one or more of the assays described below and have shown activity as inhibitors of p38 enzymes.

Biological Assays

Generation of p38 Kinases

For this assay, cDNAs of human p38α, β, and γ isozymes were cloned by PCR. These cDNAs were subcloned in the pGEX expression vector (Pharmacia). GST-p38 fusion protein was expressed in *E. Coli* and purified from bacterial pellets by affinity chromatography using glutathione agarose. p38 fusion protein was activated by incubating with constitutively active MKK6. Active p38 was separated from MKK6 by affinity chromatography. Constitutively active MKK6 was generated according to Raingeaud et al. (*Mol. Cell. Biol.*, 1247-1255 (1996)).

p38 Assay

The assays were performed in V-bottomed 96-well plates. The final assay volume was 60 μl prepared from three 20 μl additions of enzyme, substrates (MBP and ATP) and test compounds in assay buffer (50 mM Tris pH 7.5, 10 mM $MgCl_2$, 50 mM NaCl and 1 mM DTT). Bacterially expressed, activated p38 was pre-incubated with test compounds for 10 min. prior to initiation of reaction with substrates. The reaction was incubated at 25° C. for 45 min. and terminated by adding 5 μl of 0.5 M EDTA to each sample. The reaction mixture was aspirated onto a pre-wet filtermat using a SKATRON® Micro96 Cell Harvester (Skatron, Inc.), then washed with PBS. The filtermat was then dried in a microwave oven for 1 min., treated with MELTILEX® A scintillation wax (Wallac), and counted on a MICROBETA® scintillation counter Model 1450 (Wallac). Inhibition data were analyzed by nonlinear least-squares regression using PRIZM® (GraphPadSoftware). The final concentration of reagents in the assays are ATP, 1 μM; [γ-$^{33}$P]ATP, 3 nM; MBP (Sigma, #M1891), 2 g/well; p38, 10 nM; and DMSO, 0.3%.

Methods of Preparation

The compounds of the present invention can be prepared in a number of ways well known to one skilled in the art of organic synthesis. The compounds of the present invention can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The novel compounds of this invention may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and work up procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents that are compatible with the reaction conditions will be readily apparent to one skilled in the art and alternate methods must then be used. This will sometimes require a judgment to modify the order of the synthetic steps or to select one particular process scheme over another in order to obtain a desired compound of the invention. It will also be recognized that another major consideration in the planning of any synthetic route in this field is the judicious choice of the protecting group used for protection of the reactive functional groups present in the compounds described in this invention. An authoritative account describing the many alternatives to the trained practitioner is Greene, T. W. et al. (*Protective Groups in Organic Synthesis*, Third Edition, Wiley and Sons (1999)).

Abbreviations

For ease of reference, the following abbreviations are employed herein, including the methods of preparation and Examples that follow:
Ph=phenyl
Bz=benzyl
t-Bu=tertiary butyl
Me=methyl
Et=ethyl
Pr=propyl
Iso-P=isopropyl
MeOH=methanol
EtOH=ethanol
EtOAc=ethyl acetate
Boc=tert-butyloxycarbonyl
CBZ=carbobenzyloxy or carbobenzoxy or benzyloxycarbonyl
DMF=dimethyl formamide
DMSO=dimethyl sulfoxide
TFA=trifluoroacetic acid
THF=tetrahydrofuran
KOH=potassium hydroxide
$K_2CO_3$=potassium carbonate
$POCl_3$=phosphorous oxychloride
KOtBu=potassium t-butoxide
EDC or EDCI=3-ethyl-3'-(dimethylamino)propyl-carbodiimide
DIPEA=diisopropylethylamine
HOBt=1-hydroxybenzotriazole hydrate
NaH=sodium hydride
NaOH=sodium hydroxide
$Na_2S_2O_3$=sodium thiosulfate
Pd=palladium
min=minute(s)
L=liter
mL=milliliter
µL=microliter
g=gram(s)
mg=milligram(s)
mol=moles
mmol=millimole(s)
meq=milliequivalent
RT=room temperature
RBF=round bottom flask
ret. t.=HPLC retention time (minutes)
sat or sat'd=saturated
aq.=aqueous
TLC=thin layer chromatography
HPLC=high performance liquid chromatography
LC/MS=high performance liquid chromatography/mass spectrometry
MS=mass spectrometry
NMR=nuclear magnetic resonance
mp=melting point Generally, as shown in Scheme 1, p38 inhibitors of the formula (I.1) can be prepared from the substituted pyridinone 1.1 which can be prepared according methods described in the literature. Pyridinone 1.1 can be derivatized to the chloride 1.2 with, for example, $POCL_3$ then reacted with hydrazine to form intermediate 1.3. Pyridine 1.3 can be cyclized with trimethylorthoformate in the presence of acid to form the fused 6,5-triazolopyridine intermediate 1.4. Reaction with a variety of cross coupling reagents, such as an aryl boronic acid, followed by hydrolysis of the pendant ester can provide the intermediate 1.5. Reaction of 1.5 with a derivatizing reagent, such as DPPA, followed by heating in the presence of a nucleophile can provide compounds of the general formula (I.1).

Scheme 1

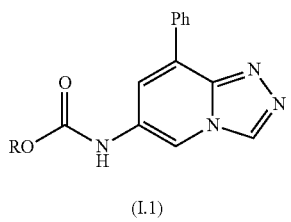

(I.1)

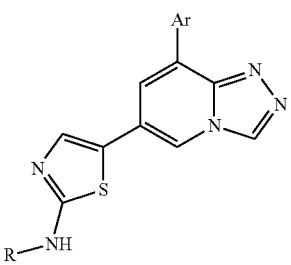

1.2a

Schemes 2 and 3 illustrate alternative methods for preparing compounds of the general invention. However, it will become evident to one of ordinary skill in the art that Schemes 2 and 3 represent only 2 specific subsets of routes and it would be possible to modify the illustrated routes to prepare additional compounds of the general formula (I). For example, the commercially available boronic acid 2.1 can be coupled to an aryl halide to give intermediate 2.2. Displacement of the fluoro group with hydrazine can afford 2.3 which, in turn can be cyclized with an orthoformate in the presence of acid to give 2.4. Coupling with a vinyl ether stannane, or an appropriate equivalent, can provide 2.5 which upon further reaction with NBS and a thiourea can afford compounds of the general structure 1.2a. Alternatively, 2-ethoxythiazole can be converted to the stannane intermediate 2.7 and then reacted with an aryl bromide 2.4 to provide additional compounds of the formula I.2b.

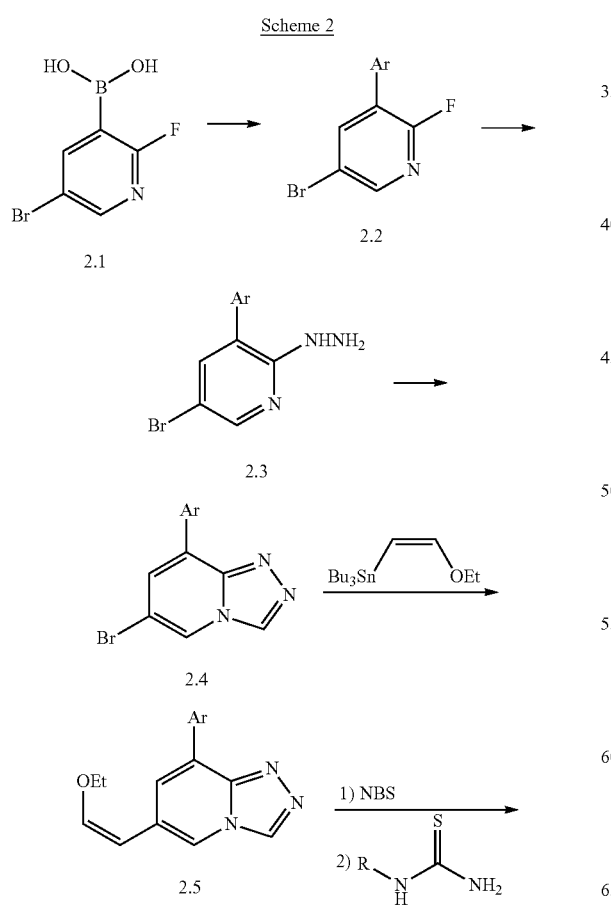

1.2b

An alternative method of preparation is outlined in Scheme 3. A pyridyl aldehyde (3.1) can be brominated to intermediate 3.2 with bromine in acetic acid. Further reaction of the aldehyde with an olefinating reagent, such as (methoxymethyl) triphenylphosphonium chloride/KOtBu can afford the vinyl ether 3.3. Treatment of this ether with NBS in water in the presence of a substituted thiourea, such as 3.4, can afford the substituted Aminothiazole 3.5. Hydrolysis can afford 3.6 which can be converted to the chloride 3.7 with POCl$_3$. The intermediate 3.7 can be reacted with hydrazine to give the 2-hydrazino pyridine 3.8 which can be cyclized to give 3.9. The bromide of 3.9 can be further reacted with a variety of cross coupling reagents to afford compounds of the general formula I.3.

Scheme 3

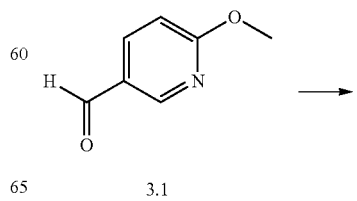

3.1

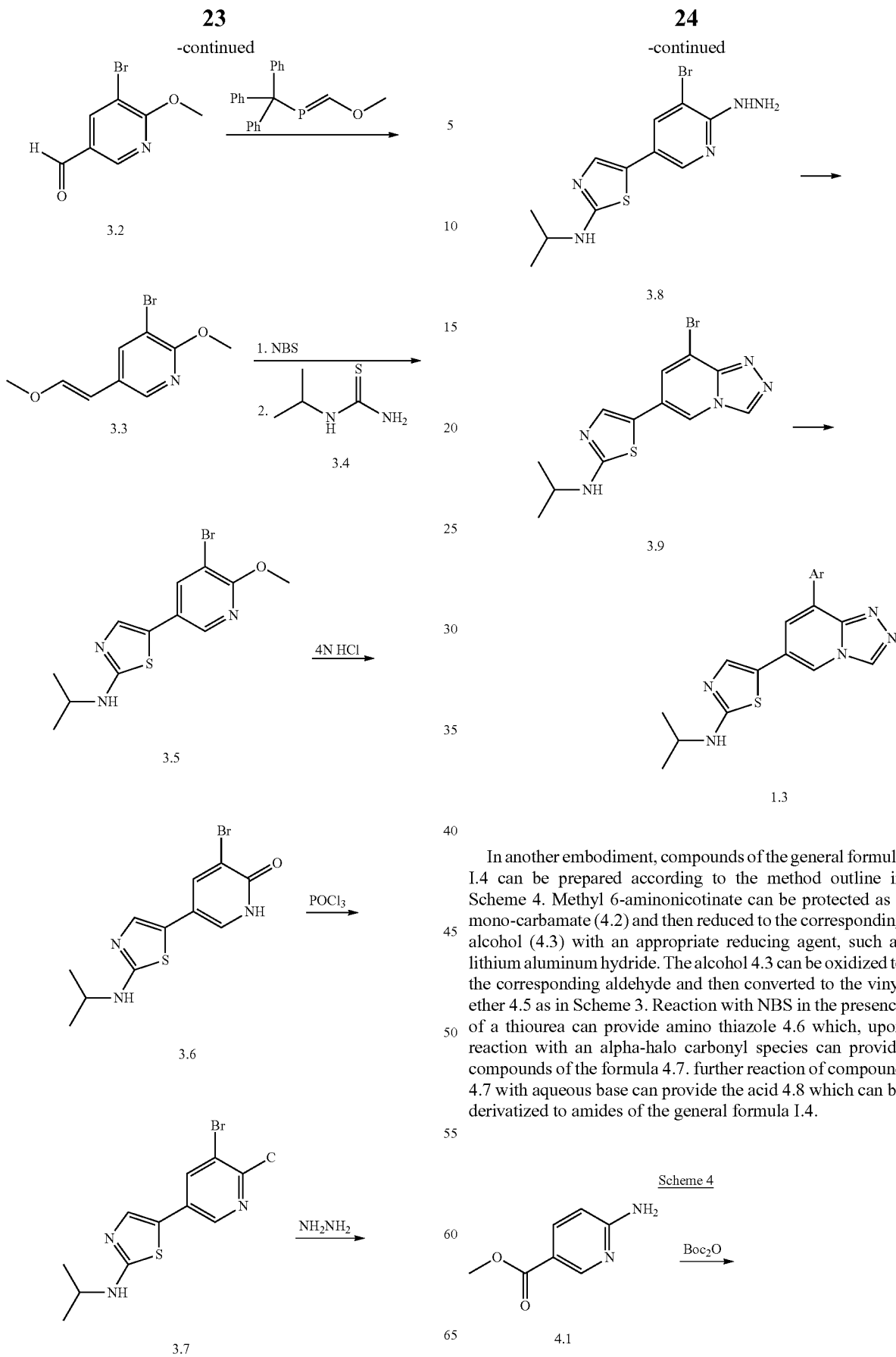

In another embodiment, compounds of the general formula I.4 can be prepared according to the method outline in Scheme 4. Methyl 6-aminonicotinate can be protected as a mono-carbamate (4.2) and then reduced to the corresponding alcohol (4.3) with an appropriate reducing agent, such as lithium aluminum hydride. The alcohol 4.3 can be oxidized to the corresponding aldehyde and then converted to the vinyl ether 4.5 as in Scheme 3. Reaction with NBS in the presence of a thiourea can provide amino thiazole 4.6 which, upon reaction with an alpha-halo carbonyl species can provide compounds of the formula 4.7. further reaction of compound 4.7 with aqueous base can provide the acid 4.8 which can be derivatized to amides of the general formula I.4.

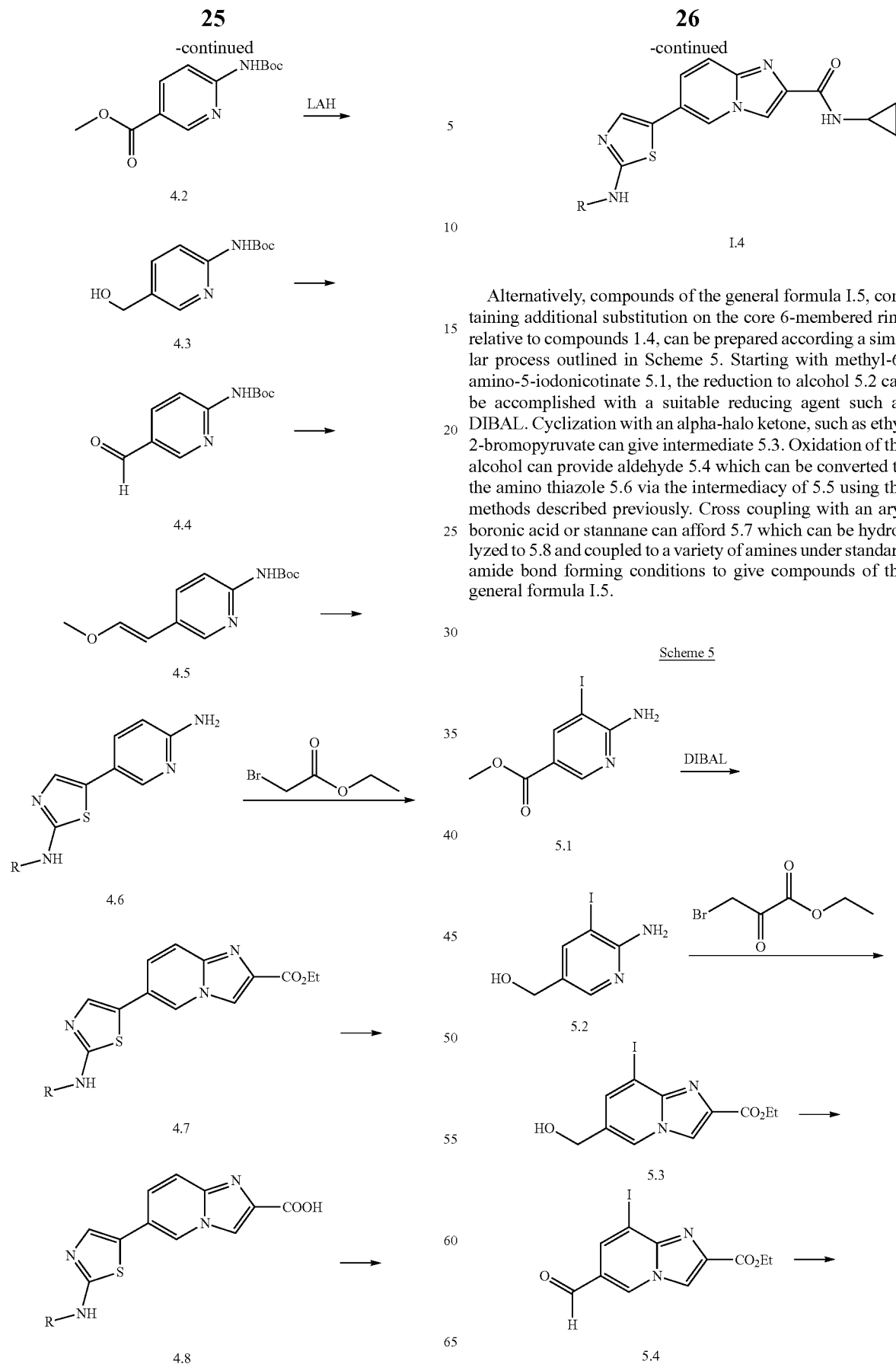

Alternatively, compounds of the general formula I.5, containing additional substitution on the core 6-membered ring relative to compounds I.4, can be prepared according a similar process outlined in Scheme 5. Starting with methyl-6-amino-5-iodonicotinate 5.1, the reduction to alcohol 5.2 can be accomplished with a suitable reducing agent such as DIBAL. Cyclization with an alpha-halo ketone, such as ethyl 2-bromopyruvate can give intermediate 5.3. Oxidation of the alcohol can provide aldehyde 5.4 which can be converted to the amino thiazole 5.6 via the intermediacy of 5.5 using the methods described previously. Cross coupling with an aryl boronic acid or stannane can afford 5.7 which can be hydrolyzed to 5.8 and coupled to a variety of amines under standard amide bond forming conditions to give compounds of the general formula I.5.

Scheme 5

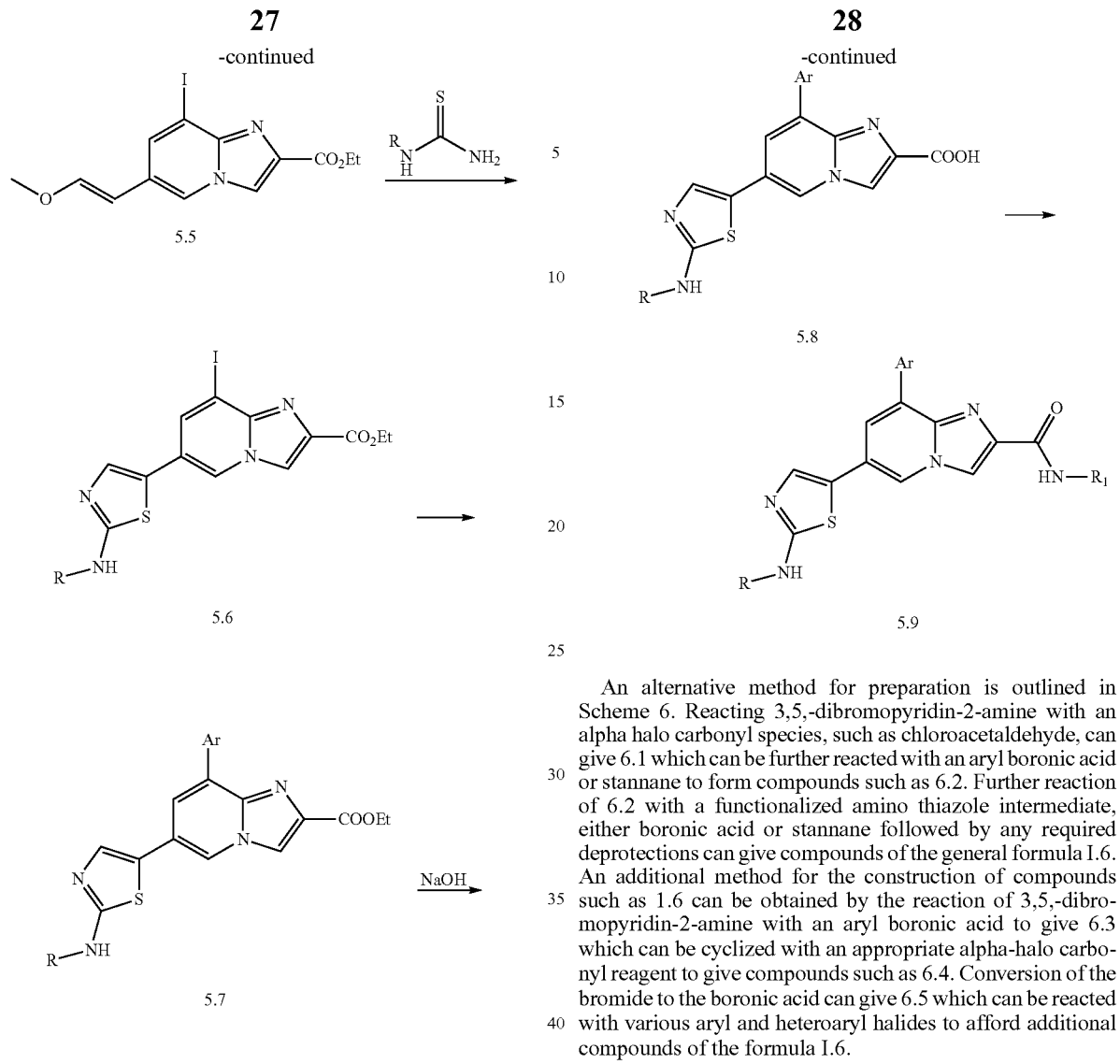

An alternative method for preparation is outlined in Scheme 6. Reacting 3,5,-dibromopyridin-2-amine with an alpha halo carbonyl species, such as chloroacetaldehyde, can give 6.1 which can be further reacted with an aryl boronic acid or stannane to form compounds such as 6.2. Further reaction of 6.2 with a functionalized amino thiazole intermediate, either boronic acid or stannane followed by any required deprotections can give compounds of the general formula I.6. An additional method for the construction of compounds such as 1.6 can be obtained by the reaction of 3,5,-dibromopyridin-2-amine with an aryl boronic acid to give 6.3 which can be cyclized with an appropriate alpha-halo carbonyl reagent to give compounds such as 6.4. Conversion of the bromide to the boronic acid can give 6.5 which can be reacted with various aryl and heteroaryl halides to afford additional compounds of the formula I.6.

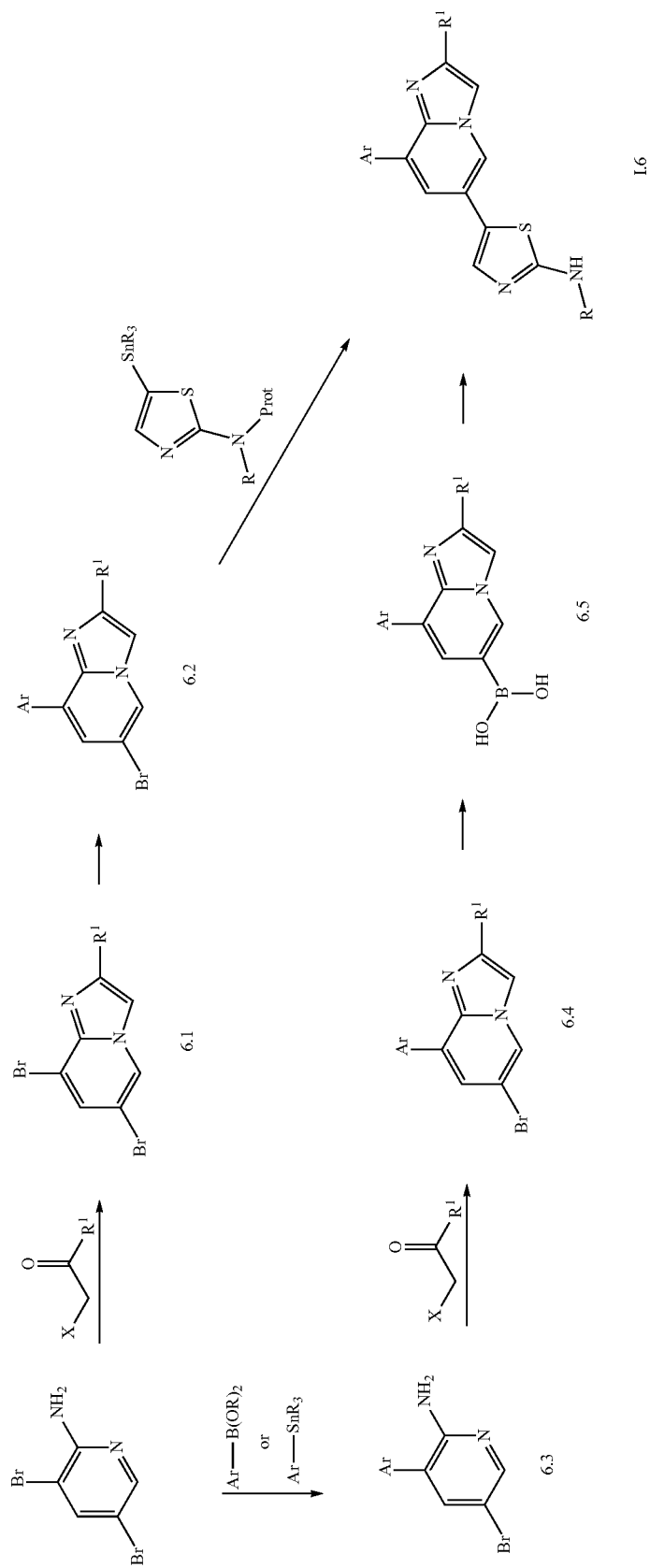

In another embodiment, compounds of the general formula I.7 can be prepared according to the method outline in Scheme 7. 3,5-Dibromopyrazine-2-amine can be reacted with a functionalized aryl group such as benzene boronic acid or an appropriate aryl stannane to afford the intermediate 7.1. Further reaction of 7.1 with a functionalized heterocycle can provide compounds of the general formula 7.2. Intermediate 7.2 can be reacted with a halo ketone to afford the cyclized analogs 7.3 which can be deprotected, if necessary, to furnish compounds of the general formula I.7.

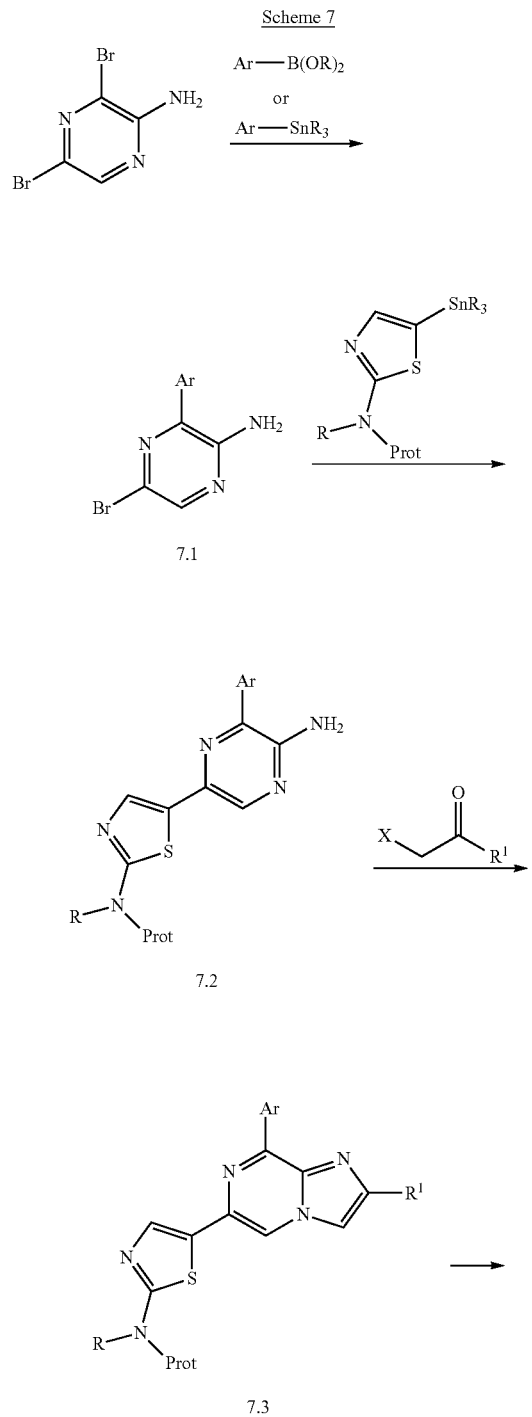

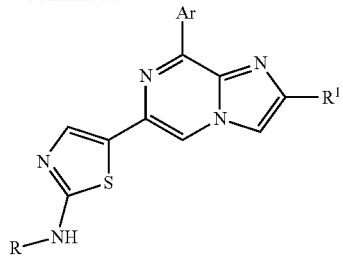

I.7

EXAMPLES

The following Examples are offered as illustrative as a partial scope of the invention and are not meant to be limiting of the scope of the invention. Unless otherwise indicated, they have been prepared, isolated and characterized using the Schemes and other methods disclosed herein. The abbreviations used herein are defined above.

In the Examples, "HPLC Condition A" refers to YMC S5 ODS-A 4.6×50 mm column, 4 mL/min flow rate, 4 min linear gradient elution (Start solvent % B=0; Final solvent % B=100), solvent A=10% MeOH/90% $H_2O$/0.2% $H_3PO_4$; solvent B=90% MeOH/10% $H_2O$/0.2% $H_3PO_4$. "HPLC Condition B" refers to Chromolith Speedrod 4.6×50 mm column, 4 mL/min flow rate, 4 min linear gradient elution (Start solvent % B=0; Final solvent % B=100), solvent A=10% MeOH/90% $H_2O$/0.2% $H_3PO_4$; solvent B=90% MeOH/10% $H_2O$/0.2% $H_3PO_4$. "HPLC Condition C" refers to Waters Sunfire C18 4.6×50 mm column, 4 mL/min flow rate, 4 min linear gradient elution (Start solvent % B=0; Final solvent % B=100), solvent A=10% MeOH/90% $H_2O$/0.1% TFA; solvent B=90% MeOH/10% $H_2O$/0.1% TFA.

Example 4

5-(8-Phenyl-[1,2,4]triazolo[4,3-a]pyridin-6-yl)-N-propylthiazol-2-amine

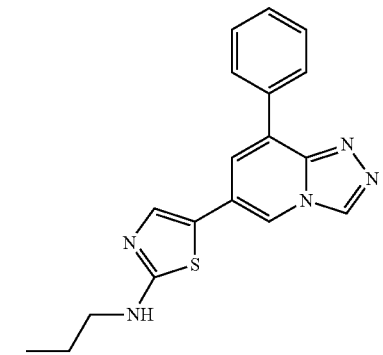 [SMILES: CCCNc1ncc(-c2cc(-c3ccccc3)c3nncn3c2)s1]

Step 1. Preparation of 5-bromo-2-fluoro-3-phenylpyridine

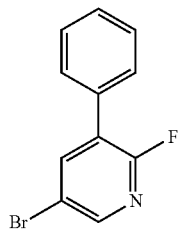

A solution of 5-bromo-2-fluoropyridin-3-ylboronic acid (620 mg, 2.82 mmol) and 1-iodobenzene (292 µL, 2.6 mmol) in 1,4-dioxane (50 µL) was degassed via nitrogen bubble for 15 mins. Then the mixture was added Pd(PPh$_3$)$_4$ (150 mg, 0.13 mmol) and aqueous Na$_2$CO$_3$ (24 µL, 5.7 mmol) and heated to 90° C. for 30 mins. The reaction was cooled to room temperature and poured into ethyl acetate (50 mL). The mixture was extracted with ethyl acetate, dried over Na$_2$SO$_4$, filtered and concentrated. The residue was purified via a flash column using 10% ethyl acetate in hexanes as an eluent. The product containing fractions were concentrated to give 5-bromo-2-fluoro-3-phenylpyridine (2.2) (326 mg, 49.8% yield).

Step 2. Preparation of 1-(5-bromo-3-phenylpyridin-2-yl)hydrazine

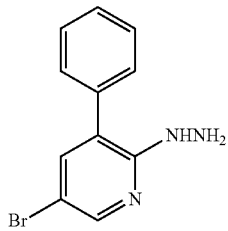 [SMILES: NNc1ncc(Br)cc1-c1ccccc1]

Hydrazine monohydrate (1.76 mL, 13 mmol) was added into a solution of 5-bromo-2-fluoro-3-phenylpyridine (326 mg, 1.29 mmol) in isopropanol (12 mL) at room temperature. The reaction mixture was heated gradually to 82° C. over 5 h and continued to heat overnight, cooled to room temperature and concentrated to give 1-(5-bromo-3-phenylpyridin-2-yl)hydrazine which was used directly in next step.

Step 3. Preparation of 6-bromo-8-phenyl-[1,2,4]triazolo[4,3-a]pyridine

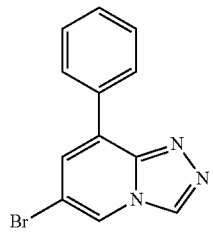 [SMILES: Brc1cc(-c2ccccc2)c2nncn2c1]

Trimethyl orthoformate (564 µL, 5.16 mmol) was added into a solution of 1-(5-bromo-3-phenylpyridin-2-yl)hydrazine (1.29 mmol, crude) in CH$_2$Cl$_2$ (12 mL). TFA (100 µL, 1.29 mmol) was added after 15 mins. The reaction mixture was stirred at room temperature for 30 mins and then concentrated. The residue was purified by a flash column using a gradient of ethyl acetate (50-80%) in heptane as an eluent. The product containing fractions were concentrated to give 6-bromo-8-phenyl-[1,2,4]triazolo[4,3-a]pyridine (328.7 mg, 85% yield).

Step 4. Preparation of (Z)-6-(2-ethoxyvinyl)-8-phenyl-[1,2,4]triazolo[4,3-a]pyridine

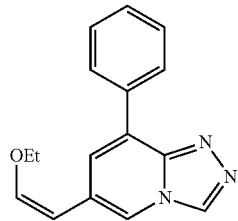 [SMILES: CCO/C=C\c1cc(-c2ccccc2)c2nncn2c1]

A mixture of 6-bromo-8-phenyl-[1,2,4]triazolo[4,3-a]pyridine (26.1 mg, 0.095 mmol), (Z)-tributyl(2-ethoxyvinyl)stannane (34.6 mg, 0.095 mmol) and tetraethylammonium chloride (16 mg, 0.095 mmol) in DMF (0.5 mL) was added PdCl$_2$(PPh$_3$)$_2$ (2 mg, 0.005 mmol). The reaction was heated at 80° C. overnight, cooled to rt, added an aqueous of KF (1.1 eq) in water (95 µL) and further stirred for 30 mins, then diluted with ethyl acetate (2 mL), filtered and rinsed with ethyl acetate (8 mL). The mixture was then washed with water (2×2 mL), separated, dried and concentrated. The residue was purified by a flash column using a gradient of ethyl acetate in hexane (50-75%) as an eluent to give compound (13 mg, 52% yield).

Step 5. Preparation of 5-(8-phenyl-[1,2,4]triazolo[4,3-a]pyridin-6-yl)-N-propylthiazol-2-amine A solution of (Z)-6-(2-ethoxyvinyl)-8-phenyl-[1,2,4]triazolo[4,3-a]pyridine (13 mg, 0.049 mmol) in 1,4-dioxane (1 mL) and water (1 mL) was added NBS (9.4 mg, 0.054 mmol) and stirred at rt for 1 h. The mixture was then added 1-propylthiourea (6.4 mg, 0.054 mmol), heated to 85-90° C. for 10 h, then cooled and concentrated. The residue was dissolved in a mixture of 20% MeOH in dichloromethane and purified by 500 µm silica gel prep plate using 75% ethyl acetate in hexanes as an eluent. The product was collected (4.5 mg, 27.4% yield). LCMS: 336.55 (M+H), Tr 2.98 min, (Conditions A).

Example 6

5-(8-(2-Fluorophenyl)-[1,2,4]triazolo[4,3-a]pyridin-6-yl)-N-isopropylthiazol-2-amine

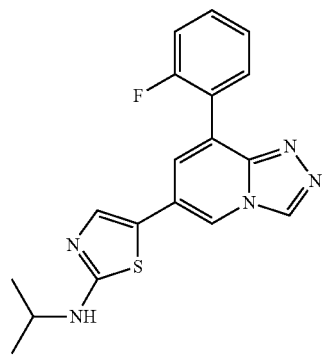 [SMILES: CC(C)Nc1ncc(-c2cc(-c3ccccc3F)c3nncn3c2)s1]

Step 1. Preparation of 5-bromo-6-methoxynicotinaldehyde

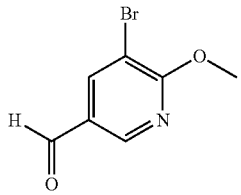

To a mixture of 6-methoxynicotinaldehyde (3 g, 0.0219 mol) and NaOAc (3.5 g, 0.0427 mol) in HOAc (10 mL) was added a solution of bromine (1.64 mL, 0.031 mol) in HOAc (10 mL) over 30 mins via an additional funnel. The mixture was heated to 90° C. for 5 h, cooled to rt. The reaction was added iced water (100 mL), neutralized to pH=7.5 with aq. NaOH (5 N), extracted with ethyl acetate (4×50 mL), washed with brine, dried over $Na_2SO_4$, filtered and concentrated. The residue was purified via flash column using dichloromethane as an eluent. The product containing fractions were collected and concentrated to give 5-bromo-6-methoxynicotinaldehyde (1.854 g, 39% yield).

Step 2. Preparation of (E)-3-bromo-2-methoxy-5-(2-methoxyvinyl)pyridine

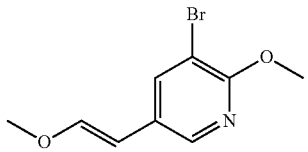

A solution of (methoxymethyl)triphenylphosphonium chloride (737 mg, 2.15 mmol) in THF (10 mL) at −78° C. was added t-BuOK (1 M in THF, 2.15 mL, 2.15 mmol) and stirred at 0° C. for 30 mins, then added dropwisely a solution of 5-bromo-6-methoxynicotinaldehyde (310 mg, 1.435 mmol) in THF (6 mL) at 0° C. via cannulation. The mixture was stirred and gradually warmed to rt overnight. The mixture was concentrated and the residue was purified via a flash column using 50% ethyl acetate in hexanes as an eluent. The product containing fractions were concentrated to give (E)-3-bromo-2-methoxy-5-(2-methoxyvinyl)pyridine (296.9 mg, 85% yield).

Step 3. Preparation of 5-(5-bromo-6-methoxypyridin-3-yl)-N-isopropylthiazol-2-amine

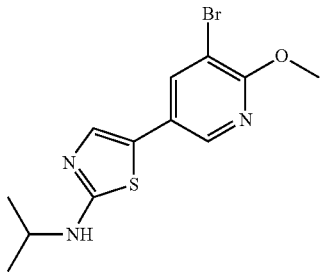 [SMILES: COc1ncc(-c2cnc(NC(C)C)s2)cc1Br]

A solution of 5-(5-bromo-6-methoxypyridin-3-yl)-N-isopropylthiazole-2-amine (1.25 g, 7.56 mmol) in a mixture of 1:1 ratio 1,4-dioxane (38 mL) and water (38 mL) was added NBS (1.57 g, 8.32 mmol) and stirred for 1.5 h. The mixture was then added isopropylthiourea (0.983 g, 8.32 mmol) and heated to 75° C. for 5 h. The mixture was cooled and concentrated. The residue was neutralized with concentrated $NH_4OH$ and the precipitate was sonicated, filtered, rinsed with water and dried to give the product.

Step 4. Preparation of 3-bromo-5-(2-(isopropylamino)thiazol-5-yl)pyridin-2(1H)-one

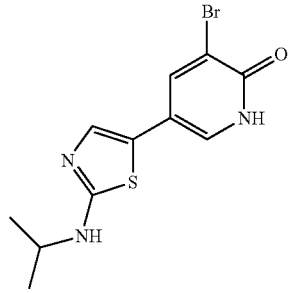 [SMILES: CC(C)Nc1ncc(-c2c[nH]c(=O)c(Br)c2)s1]

A solution of 5-(5-bromo-6-methoxypyridin-3-yl)-N-isopropylthiazol-2-amine (390 mg, 1.18 mmol) in THF (1 mL) was added HCl (4 N, 10 mL) and heated at 90° C. overnight. The mixture was cooled to rt, neutralized with aq NaOH (5 N) and stirred for 1 h. The solid was filtered, rinsed with water and dried to give 3-bromo-5-(2-(isopropylamino)thiazol-5-yl)pyridin-2(1H)-one (359.4 mg, 96%).

Step 5. Preparation of 5-(5-bromo-6-chloropyridin-3-yl)-N-isopropylthiazol-2-amine

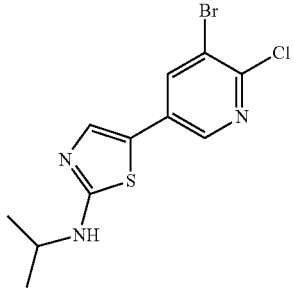 [SMILES: CC(C)Nc1ncc(-c2cnc(Cl)c(Br)c2)s1]

A mixture of 3-bromo-5-(2-(isopropylamino)thiazol-5-yl)pyridin-2(1H)-one (359 mg, 1.14 mmol) was heated at 100° C. overnight and cooled to rt. The mixture was concentrated and added dichloromethane (20 mL), water (3 mL) and saturated aq $NaHCO_3$ (3 mL). The mixture was stirred rapidly and separated. The aqueous was extracted with dichloromethane twice. The organic layers were combined, dried over $Na_2SO_4$, filtered and concentrated to give the product (378 mg, 99% yield).

Step 6. Preparation of 5-(8-bromo-[1,2,4]triazolo[4,3-a]pyridin-6-yl)-N-isopropylthiazol-2-amine

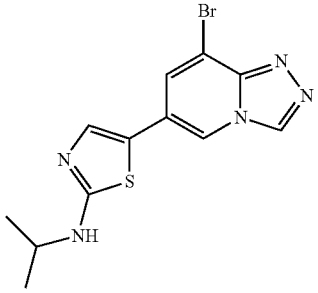 [SMILES: CC(C)Nc1ncc(-c2cc(Br)c3nncn3c2)s1]

To a mixture of 5-(5-bromo-6-chloropyridin-3-yl)-N-isopropylthiazol-2-amine (341 mg, 1.02 mmol) in n-BuOH (5 mL) was added hydrazine monohydrate (806 μL, 2.55 mmol). The reaction mixture was heated at 105° C. in a sealed tube overnight, cooled and concentrated. The residue was added trimethyl orthoformate (335 μL, 3.06 mmol), CH$_2$Cl$_2$ (5 mL) and stirred for 10 mins, then added TFA (118 μL, 1.53 mmol). The reaction was continued to stir for 45 mins, and then concentrated. The residue was added water (10 mL), neutralized with NaHCO$_3$, stirred overnight, filtered and rinsed with water. The dried solid was purified by a flash column using 5% MeOH in dichloromethane as an eluent. The product containing fractions were concentrated to give the product (208.1 mg, 60% yield in two-step).

Step 7. Preparation of 5-(8-(2-fluorophenyl)-[1,2,4]triazolo[4,3-a]pyridin-6-yl)-N-isopropylthiazol-2-amine A mixture of 5-(8-bromo-[1,2,4]triazolo[4,3-a]pyridin-6-yl)-N-isopropylthiazol-2-amine (19.6 mg, 0.0579 mmol) and 2-fluorophenylboronic acid (12.7 mg, 0.081 mmol) in toluene (0.58 mL) was degassed via nitrogen bubble, then was added Pd(PPh$_3$)$_4$ (3.3 mg, 0.003 mmol), aqueous K$_3$PO$_4$ (2 M, 58 μL, 0.116 mmol) and ethanol (84 μL). The reaction mixture was heated to 100° C. overnight, cooled to rt, diluted with EtOH (1 mL), filtered and concentrated. The residues were purified directly by reverse phase preparative HPLC and the product containing fractions were concentrated and neutralized with aqueous NaHCO$_3$ to precipitate the product. The solids were filtered, washed and dried to give (9.7 mg, 47% yield). LCMS 354.23, Tr 3.50 min (Conditions A).

Examples 7 to 29

Additional compounds of the general formula 3.I prepared according to the methods previously described in Schemes 2 and 3 are illustrated in Table 1.

TABLE 1

| Example No. | Structure | LCMS | HPLC Tr (min) |
|---|---|---|---|
| 7 | | 322.47 | 2.69, A |
| 8 | 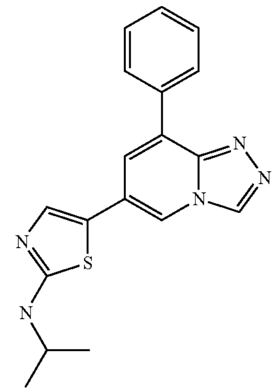 [SMILES: CC(C)Nc1ncc(-c2cc(-c3ccccc3)c3nncn3c2)s1] | 336.54 | 2.87, A |
| 9 | 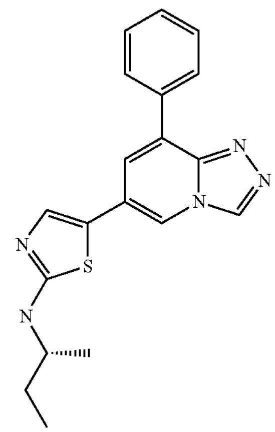 [SMILES: CC[C@@H](C)Nc1ncc(-c2cc(-c3ccccc3)c3nncn3c2)s1] | 350.5 | 3.10, A |
| 10 | 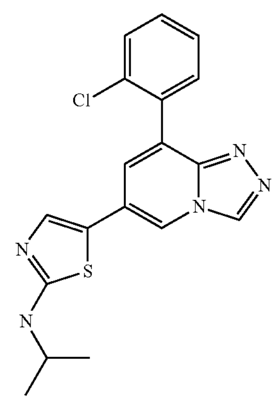 [SMILES: CC(C)Nc1ncc(-c2cc(-c3ccccc3Cl)c3nncn3c2)s1] | 370.22 | 2.94, A |
| 12 | 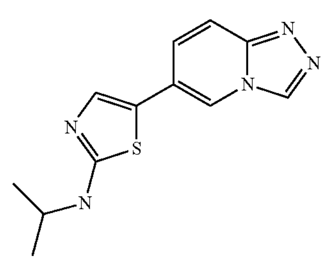 [SMILES: CC(C)Nc1ncc(-c2ccc3nncn3c2)s1] | 260.16 | 1.58, A |

TABLE 1-continued
| Example No. | Structure | LCMS | HPLC Tr (min) |
|---|---|---|---|
| 13 | 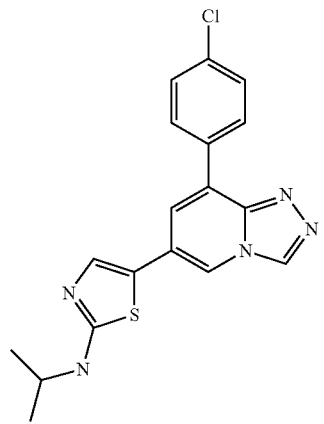 [SMILES: CC(C)Nc1ncc(-c2cc(-c3ccc(Cl)cc3)c3nncn3c2)s1] | 370.2 | 3.33, A |
| 14 | 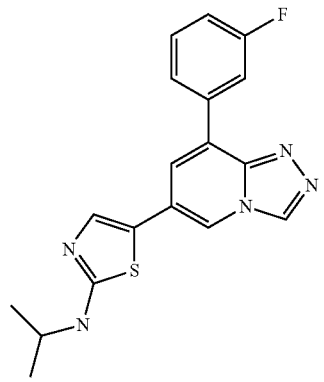 [SMILES: CC(C)Nc1ncc(-c2cc(-c3cccc(F)c3)c3nncn3c2)s1] | 370.21 | 3.33, A |
| 15 | 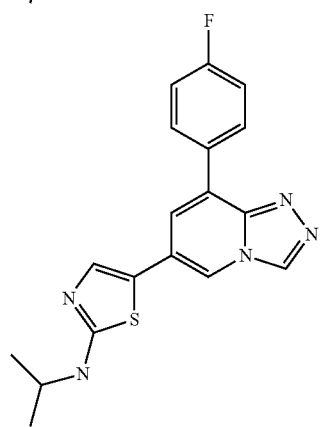 | 354.18 | 3.01, A |
| 16 | 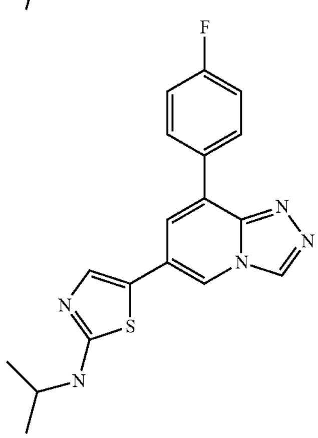 | 354.19 | 3.02, A |
TABLE 1-continued
| Example No. | Structure | LCMS | HPLC Tr (min) |
|---|---|---|---|
| 19 | 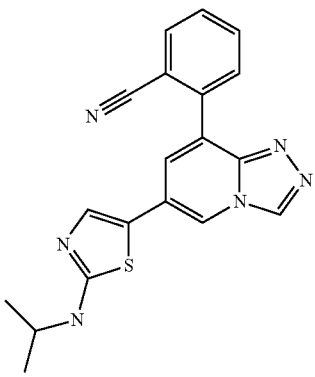 [SMILES: CC(C)Nc1ncc(-c2cc(-c3ccccc3C#N)c3nncn3c2)s1] | 361.27 | 2.67, B |
| 20 | 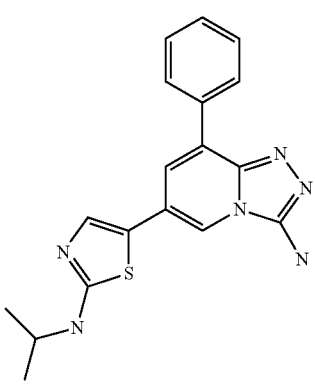 [SMILES: CC(C)Nc1ncc(-c2cc(-c3ccccc3)c3nnc(N)n3c2)s1] | 351.19 | 2.83, B |
| 21 | 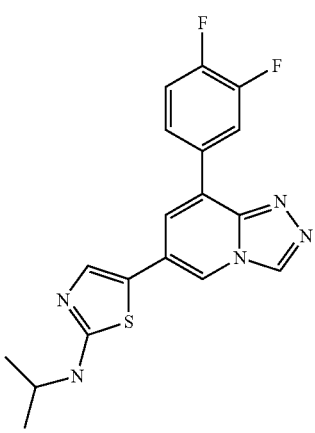 [SMILES: CC(C)Nc1ncc(-c2cc(-c3ccc(F)c(F)c3)c3nncn3c2)s1] | 372.2 | 3.39, B |
| 22 | 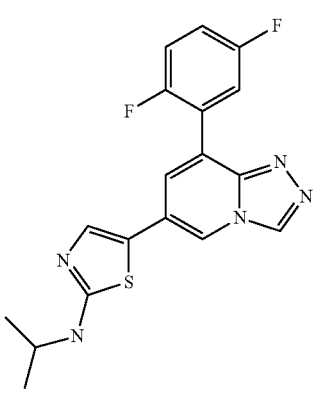 [SMILES: CC(C)Nc1ncc(-c2cc(-c3cc(F)ccc3F)c3nncn3c2)s1] | 372.22 | 3.06, B |

TABLE 1-continued

| Example No. | Structure | LCMS | HPLC Tr (min) |
|---|---|---|---|
| 23 | 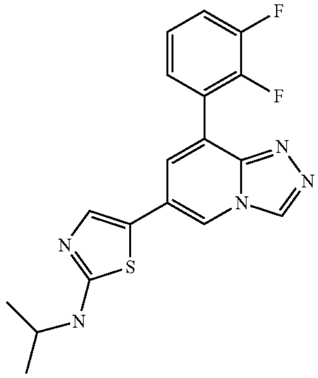 [SMILES: CC(C)Nc1ncc(-c2cc(-c3cccc(F)c3F)c3nncn3c2)s1] | 372.23 | 3.16, B |
| 25 | 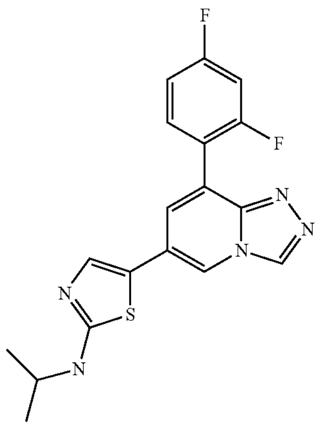 [SMILES: CC(C)Nc1ncc(-c2cc(-c3ccc(F)cc3F)c3nncn3c2)s1] | 372.22 | 3.11, A |
| 26 | 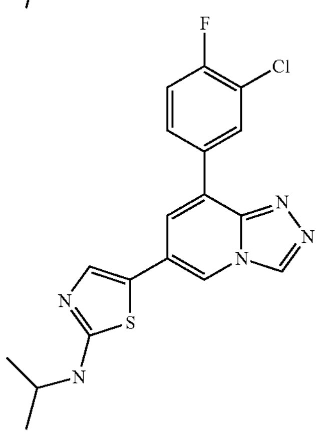 | 388.18 | 3.64, B |
| 27 | 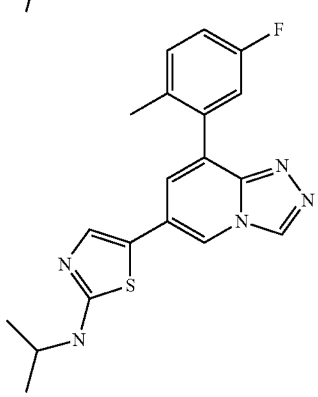 | 268.25 | 3.19, B |
| 28 | | 352.2 | 2.69, B |

Example 32

(R)-6-(2-(Sec-butylamino)thiazol-5-yl)-N-methyl-8-phenylimidazo[1,2-a]pyridine-2-carboxamide Step 1. Preparation of (6-amino-5-iodopyridin-3-yl)methanol A solution of methyl 6-amino-5-iodonicotinate (335 mg, 1.205 mmol) in dichloromethane (18 mL) was added DIBAL (1.5 M in toluene, 1.61 mL, 2.41 mmol) via syringe dropwise at 0° C. The reaction was monitored by LC_MS, and added more DIBAL (0.8 mL, 1.2 mmol) to drive the reaction to complete. The reaction was quenched with addition of MeOH (1 mL) dropwise at 0° C., stirred at rt for 2 h and filtered through a CELITE® pad, rinsed with ethyl acetate and dichloromethane. The organic layers were combined and concentrated onto SiO$_2$ which was purified by a flash column using 50%, 80% and 100% ethyl acetate in heptane as an eluent to give the product (204 mg, 68 mmol).

Step 2. Preparation of ethyl 6-(hydroxymethyl)-8-iodoH-imidazo[1,2-a]pyridine-2-carboxylate

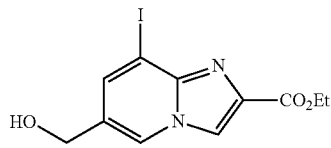 [SMILES: CCOC(=O)c1cn2cc(CO)cc(I)c2n1]

A solution of (6-amino-5-iodopyridin-3-yl)methanol (0.616 mmol) in THF (3 mL) was added ethyl 2-bromoacetate (123 µL, 0.878 mmol). The mixture was heated to reflux for 4 h. The reaction was cooled and stirred. The solid was filtered, rinsed with THF and dried to give the product (266 mg, 64% yield).

Step 3. Preparation of ethyl 6-formyl-8-iodoH-imidazo[1,2-a]pyridine-2-carboxylate

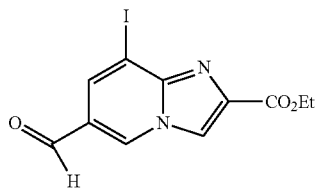 [SMILES: CCOC(=O)c1cn2cc(C=O)cc(I)c2n1]

A mixture of ethyl 6-(hydroxymethyl)-8-iodoH-imidazo[1,2-a]pyridine-2-carboxylate (266 mg, 0.768 mmol) and triethylamine (321 µL, 2.3 mmol) in DMSO (1.3 mL) was added Pyridine SO₃ (366 mg, 2.3 mmol) in portions and stirred 2.5 h at 15° C. The reaction was quenched with ice (10-15 g) and stirred for 2.5 h. The solid was filtered, rinsed with water, dried and purified by a flash column using 50% ethyl acetate as an eluent. The product containing fractions were concentrated to give the aldehyde (139 mg, 53% yield).

Step 4. Preparation of (E)-ethyl 8-iodo-6-(2-methoxyvinyl)H-imidazo[1,2-a]pyridine-2-carboxylate

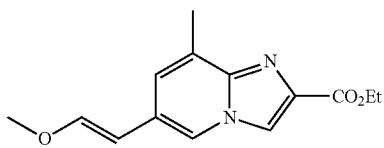 [SMILES: CCOC(=O)c1cn2cc(/C=C/OC)cc(C)c2n1]

A solution of (methoxymethyl)triphenylphosphonium chloride (239 mg, 0.696 mmol) in THF (3 mL) was added KOBU-t (1 M in THF, 696 µL, 0.696 mmol) at −78° C., then stirred at 0° C. in an ice bath for 30 mins. The mixture was then added a solution of ethyl 6-formyl-8-iodoH-imidazo[1,2-a]pyridine-2-carboxylate in THF (5 mL) and stirred at rt overnight. The mixture was filtered and concentrated. The residue was purified by a flash column using 20-33% ethyl acetate in heptane as an eluent to give the product (83 mg, 58% yield).

Step 5. Preparation of (R)-ethyl 6-(2-(sec-butylamino)thiazol-5-yl)-8-iodoindolizine-2-carboxylate

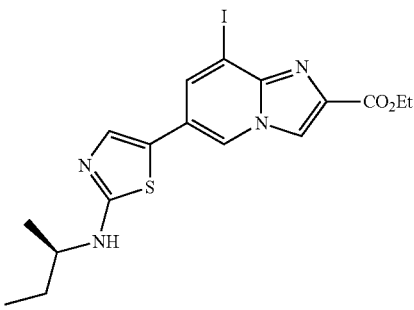 [SMILES: CCOC(=O)c1cn2cc(-c3cnc(N[C@H](C)CC)s3)cc(I)c2n1]

A solution of (E)-ethyl 8-iodo-6-(2-methoxyvinyl)H-imidazo[1,2-a]pyridine-2-carboxylate (83 mg, 0.223 mmol) in THF (1 mL) and water (1 mL) was added NBS (44 mg, 0.245 mmol). The mixture was stirred at rt for 45 mins, then added (R)-1-sec-butylthiourea (33 mg, 0.245 mmol). The reaction was heated at 65° C. overnight, cooled to rt, diluted with ethyl acetate (15 mL) and NaHCO₃ (1 mL) and water (2 mL) and separated. The aqueous was extracted with ethyl acetate and the combined organic layers were dried over Na₂SO₄, filtered and concentrated. The residue was purified by a flash column using 33-50% ethyl acetate in heptane as an eluent to give the product (73.2 mg, 69% yield).

Step 6. Preparation of (R)-ethyl 6-(2-(sec-butylamino)thiazol-5-yl)-8-phenylimidazo[1,2-a]pyridine-2-carboxylate

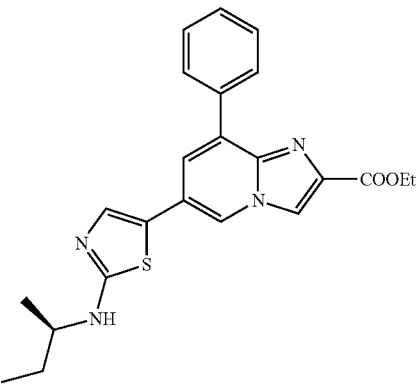 [SMILES: CCOC(=O)c1cn2cc(-c3cnc(N[C@H](C)CC)s3)cc(-c3ccccc3)c2n1]

A mixture of (E)-ethyl 8-iodo-6-(2-methoxyvinyl)H-imidazo[1,2-a]pyridine-2-carboxylate (68.6 mg, 0.1459 mmol) and phenylboronic acid (25 mg, 0.2 mmol) in toluene was degassed through nitrogen bubble for 15 mins, then added Pd(PPh₃)₄ (8.4 mg, 0.007 mmol), K₃PO₄ (2M, 146 µL, 0.29 mmol) and ethanol (180 L). The reaction was heated at 75° C. for 3 h and continued to heat at 80° C. overnight, then cooled to rt. The reaction was diluted with ethyl acetate (25 mL), washed with brine, dried over Na₂SO₄ and concentrated. The residue was purified by a flash column using 33% ethyl acetate in heptane as an eluent to give the product (66 mg, 100%). LCMS: 421.2, HPLC rt 3.84 min (Conditions B).

Step 7. Preparation of (R)-6-(2-(sec-butylamino) thiazol-5-yl)-8-phenylH-imidazo[1,2-a]pyridine-2-carboxylic acid

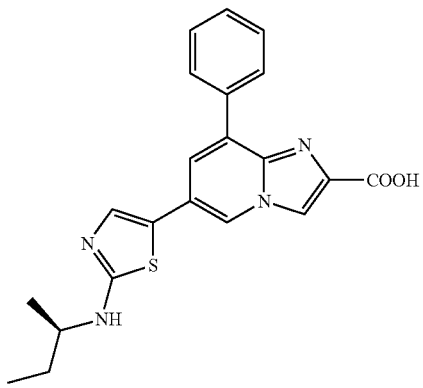 [SMILES: CC[C@@H](C)Nc1ncc(-c2cc(-c3ccccc3)c3nc(C(=O)O)cn3c2)s1]

A solution of (R)-ethyl 6-(2-(sec-butylamino)thiazol-5-yl)-8-phenylH-imidazo[1,2-a]pyridine-2-carboxylate (60 mg, 0.1429 mmol) in THF (290 uL) and MeOH (290 uL) was added 1N NaOH (290 uL, 0.29 mmol) and stirred at rt for 2 h. The mixture was then concentrated and neutralized with AcOH, stirred overnight. The precipitate was filtered, rinsed with water and dried to give the acid (42 mg, 77% yield).

Step 8. Preparation of (R)-6-(2-(sec-butylamino) thiazol-5-yl)-N-alkyl-8-phenylH-imidazo[1,2-a]pyridine-2-carboxamide A solution of (R)-6-(2-(sec-butylamino)thiazol-5-yl)-8-phenylH-imidazo[1,2-a]pyridine-2-carboxylic acid (42 mg, 0.107 mmol) in DMF (600 uL) was added HOBt (17.3 mg, 0.128 mmol) and EDCI (24.5 mg, 0.128 mmol). The mixture was stirred at rt for 1 h and equally divided into three portions. Each portion was added either methylamine (2M in THF, 45 uL, 0.089 mmol), ethylamine (7.3 mg, 0.089 mmol) or cyclopropylamine (6.2 uL, 0.089 mmol), and stirred at rt for 1 h. The mixture was added water (0.6 mL) and stirred for several hours. The solids were filtered, rinsed with water and dried to give the corresponding amides (Methyl-: 16.3 mg, 100% yield), ethyl-: 10.3 mg, 69% yield, cyclopropyl-: 7.2 mg, 47% yield). LCMS 406.3, HPLC Tr 3.67 min (Conditions B).

Example 33

Ethyl 6-(2-aminothiazol-5-yl)-8-phenylimidazo[1,2-a]pyridine-2-carboxylate

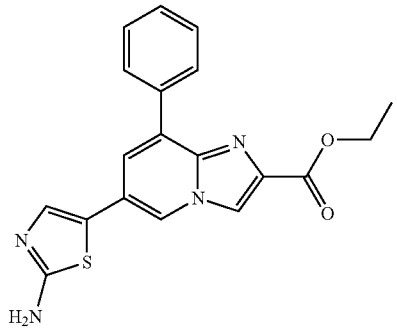 [SMILES: CCOC(=O)c1cn2cc(-c3cnc(N)s3)cc(-c3ccccc3)c2n1]

Step 1. Preparation of ethyl 6,8-dibromoimidazo[1,2-a]pyridine-2-carboxylate hydrobromide

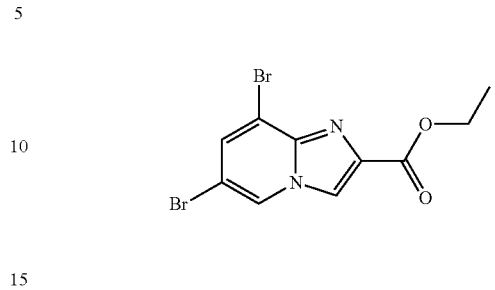

A mixture of 3,5-dibromopyridin-2-amine (2.51 g, 10 mmol) and ethyl 3-bromo-2-oxopropanoate (2.5 g, 13 mmol) in THF (50 mL) was heated at reflux 48 hrs. The solution was evaporated and the residue triturated with ether and the resulting solid was filtered and dried to give ethyl 6,8-dibromoimidazo[1,2-a]pyridine-2-carboxylate hydrobromide (3.0 g, 69% yield). LCMS (Conditions C): 2.70 min (RT); (M+H)$^+$= 347.09 (60%), 349.09 (100%), 351.08 (60%). $^1$H NMR, 400 MHz, CDCl$_3$: δ 8.39 (d, 1.5 Hz, 1 H), 8.28 (s, 1 H), 7.67 (d, 1.5 Hz, 1 H), 4.46 (q, J=7.0 Hz, 2 H), 1.43 (t, J=7.0 Hz, 3 H).

Step 2. Preparation of ethyl 6-bromo-8-phenylimidazo[1,2-a]pyridine-2-carboxylate

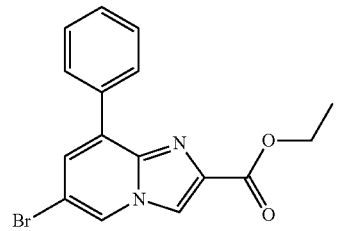 [SMILES: CCOC(=O)c1cn2cc(Br)cc(-c3ccccc3)c2n1]

A solution of ethyl 6,8-dibromoimidazo[1,2-a]pyridine-2-carboxylate hydrobromide (0.5 g, 1.2 mmol) and phenylboronic acid (0.15 g, 1.2 mmol) in toluene (10 mL) and ethanol (2 mL) was bubbled nitrogen for 20 mins. The mixture was then treated with Pd(PPh$_3$)$_4$ (30 mg, 0.026 mmol) and K$_3$PO$_4$ (2 M, 1 mL, 2 mmol) and heated at 80° C. overnight. The reaction was cooled, poured into ethyl acetate (200 mL), washed with brine, separated, and concentrated. The residue was purified by column chromatography on silica gel using ethyl acetate in hexanes (10%) as eluent. The product containing fractions were concentrated to give 0.23 g (58% yield) of ethyl 6-bromo-8-phenylimidazo[1,2-a]pyridine-2-carboxylate as a white solid. LCMS (Conditions C): 3.41 min (RT); (M+H)$^+$=347.24 (100%), 345.24 (100%). $^1$H NMR, 400 MHz, CDCl$_3$: δ 8.27 (d, J=1.6 Hz, 1 H), 8.19 (s, 1 H), 8.02 (m, 2H), 7.52-7.41 (m, 4 H), 4.45 (q, J=7.1 Hz, 2 H), 1.42 (t, J=7.0 Hz, 3 H).

Step 3. Preparation of ethyl 6-(2-(bis(tert-butoxycarbonyl)amino)thiazol-5-yl)-8-phenylimidazo[1,2-a]pyridine-2-carboxylate

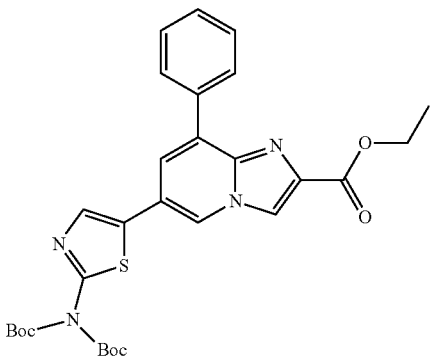 [SMILES: CCOC(=O)c1cn2cc(-c3cnc(N(C(=O)OC(C)(C)C)C(=O)OC(C)(C)C)s3)cc(-c3ccccc3)c2n1]

A solution of ethyl 6-bromo-8-phenylimidazo[1,2-a]pyridine-2-carboxylate (0.10 g, 0.29 mmol) and tert-butyl(tert-butoxycarbonyl)(5-(4,4,5,5-tetramethyl-1,3,2-dioxaborolan-2-yl)thiazol-2-yl)carbamate (0.14 g, 0.33 mmol) in toluene (3 mL) and ethanol (1 mL) was bubbled nitrogen for 20 mins. The mixture was then treated with Pd(PPh$_3$)$_4$ (30 mg, 0.026 mmol) and K$_3$PO$_4$ (2 M, 1 mL, 2 mmol) and heated at 80° C. overnight. The reaction was cooled, poured into ethyl acetate (200 mL), washed with brine, separated, and concentrated. The residue was purified by column chromatography using ethyl acetate in hexanes (10-30%) as eluent. The product containing fractions were concentrated to give 28 mg (15% yield) of ethyl 6-(2-(bis(tert-butoxycarbonyl)-amino)thiazol-5-yl)-8-phenylimidazo[1,2-a]pyridine-2-carboxylate as a white solid. LCMS (Conditions C): 4.15 min (RT); (M+H)$^+$= 565.62 (100%).

Step 4. Preparation of ethyl 6-(2-aminothiazol-5-yl)-8-phenylimidazo[1,2-a]pyridine-2-carboxylate A solution of ethyl 6-(2-(bis(tert-butoxycarbonyl)amino)thiazol-5-yl)-8-phenyl-imidazo[1,2-a]pyridine-2-carboxylate (28 mg) in 3 ml of TFA was stirred at room temperature for 2 hours. The Solvent was evaporated and the residue made basic with NH$_4$OH/MeOH/CH$_2$Cl$_2$ (1:9:90) solution, and then evaporated to dryness. The residue was purified by column chromatography on silica gel using ethyl acetate as eluent to give 7 mg of Ethyl 6-(2-aminothiazol-5-yl)-8-phenylimidazo[1,2-a]pyridine-2-carboxylate as a white solid. LCMS (Conditions C): 2.53 min (RT); (M+H)$^+$=365.28 (100%). $^1$H NMR, 400 MHz, DMSO: δ 8.56 (m, 2 H), 8.11 (m, 2 H), 7.81 (s, 1H), 7.65 (s, 1H), 7.56-7.47 (m, 3 H), 7.32 (bs, 2 H), 4.33 (q, J=7.1 Hz, 2 H), 1.31 (t, J=7.0 Hz, 3 H).

Example 34

Ethyl 6-(2-(isopropylamino)thiazol-5-yl)-8-phenylimidazo[1,2-a]pyridine-2-carboxylate

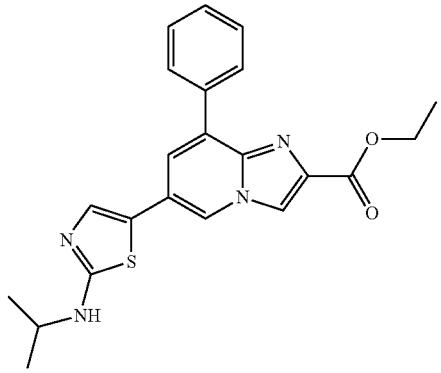 [SMILES: CCOC(=O)c1cn2cc(-c3cnc(NC(C)C)s3)cc(-c3ccccc3)c2n1]

Step 1. Preparation of tert-butyl 5-bromothiazol-2-ylcarbamate

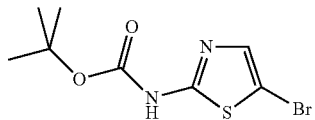

Di-tert-butyl dicarbonate (28.90 g, 132.4 mmol) was added portionwise to a suspension of 2-amino-5-bromothiazole monohydrobromide (28.64 g, 110.3 mmol) in pyridine (100 mL) over 20 minutes at room temperature. The mixture was stirred at room temperature overnight. The solvent was evaporated. The residue was extracted between 0.5 N HCl (200 mL) and ethyl acetate (200 mL). The organic layer was separated and concentrated. The residue was filtered through a pad of silica gel using 10% ethyl acetate/hexane as a solvent. The filtrate was concentrated to give tert-butyl-5-bromothiazol-2-ylcarbamate (19.5 g, 63% yield) as a white solid. LCMS (Conditions A): 3.40 min (RT); (M+H)$^+$=225.12 (100%), 223.12 (95%). $^1$H NMR, 400 MHz, CDCl$_3$: δ 7.27 (s, 1 H), 1.60 (s, 9 H).

Step 2. Preparation of tert-butyl 5-bromothiazol-2-yl(isopropyl)carbamate

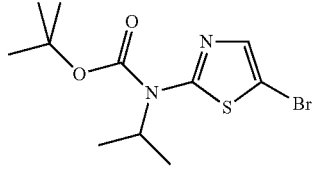 [SMILES: CC(C)N(C(=O)OC(C)(C)C)c1ncc(Br)s1]

To a solution of tert-butyl 5-bromothiazol-2-ylcarbamate (3 g, 10.7 mmol), isopropanol (6.40 g, 107.4 mmol) and triphenylphosphine (5.63 g, 21.5 mmol) in THF (30 mL) was added diethyl azodicarboxylate dropwise at 0° C. The mixture was stirred at 0° C. and slowly warmed up to room temperature overnight. The solvent was evaporated. The residue was redissolved in dichloromethane (20 mL) and filtered to get rid of the undissolved solid. The filtrate was concentrated and purified by column chromatography on silica gel using 100% hexane to give a light yellow oil (3.10 g, 90% yield). LCMS (Conditions C): 4.19 min (RT); (M+H)$^+$= 267.01 (100%), 265.01 (95%), 224.95 (60%), 222.95 (60%). $^1$H NMR, 400 MHz, CDCl$_3$: δ 7.34 (s, 1 H), 5.29 (m, 1 H), 1.59 (s, 9 H), 1.45 (d, 6.8 Hz, 6 H).

Step 3. Preparation of tert-butyl-isopropyl(5-(4,4,5,5-tetramethyl-1,3,2-dioxaborolan-2-yl)thiazol-2-yl)carbamate To a solution of tert-butyl 5-bromothiazol-2-yl(isopropyl)carbamate (7.5 g, 23.3 mmol) in THF (50 mL) was added n-butyllithium (1.6 M in hexane, 21.8 mL) dropwise at −78° C. The solution turned orange. The solution was stirred at −78° C. for minutes before 2-isopropoxy-4,4,5,5-tetramethyl-1,3,2-dioxaborolane (6.49 g, 34.9 mmol) was added dropwise. The mixture was stirred at −78° C. for 2 hours then warmed to room temperature. The reaction was quenched with 1:1 ammonium chloride/water (50 mL). The resulted mixture was extracted with ethyl acetate (100 mL). The organic layer was separated, washed with water, brine and concentrated. To the brown solid residue was added hexane (30 mL). The mixture was filtered and the filter cake was washed with hexane (20 mL) and dried to give as a yellow solid (4.17 g, 48% yield). LCMS (Conditions C): 3.21 min (RT); (M+H)+=247.12 (40%), 245.12 (50%), 233.10 (75%), 231.10 (100%). ¹H NMR, 400 MHz, CDCl₃: δ 7.95 (s, 1 H), 5.37 (m, 1 H), 1.60 (s, 9 H), 1.44 (d, 6.7 Hz, 6 H), 1.34 (s, 12 H).

Step 4. Preparation of ethyl 6-(2-(tert-butoxycarbonyl-(isopropyl)amino)thiazol-5-yl)-8-phenylimidazo-[1,2-a]pyridine-2-carboxylate

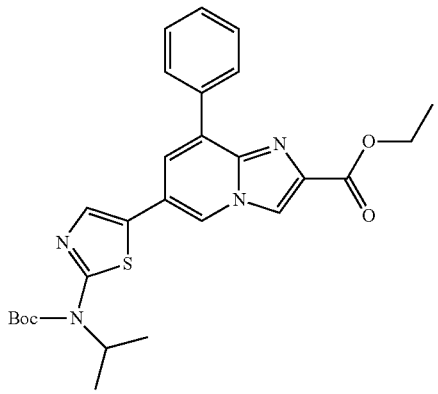 [SMILES: CCOC(=O)c1cn2cc(-c3cnc(N(C(=O)OC(C)(C)C)C(C)C)s3)cc(-c3ccccc3)c2n1]

A solution of ethyl 6-bromo-8-phenylimidazo[1,2-a]pyridine-2-carboxylate (0.10 g, 0.29 mmol) and tert-butyl isopropyl(5-(4,4,5,5-tetramethyl-1,3,2-dioxaborolan-2-yl)thiazol-2-yl)carbamate (0.128 g, 0.34 mmol) in toluene (3 mL) and ethanol (1 mL) was bubbled nitrogen for 20 mins. The mixture was then treated with Pd(PPh₃)₄ (30 mg, 0.026 mmol) and K₃PO₄ (2 M, 1 mL, 2 mmol) and heated at 80° C. overnight. The reaction was cooled, poured into ethyl acetate (200 mL), washed with brine, separated, and concentrated. The residue was purified by column chromatography on silica gel using ethyl acetate in hexanes (10-50%) as eluent. The product containing fractions were concentrated to give 75 mg (53% yield) of ethyl 6-(2-(tert-butoxycarbonyl-(isopropyl)amino)thiazol-5-yl)-8-phenylimidazo[1,2-a]pyridine-2-carboxylate as a white solid. LCMS (Conditions C): 4.30 min (RT); (M+H)+=507.38 (100%).

Step 5. Preparation of ethyl 6-(2-(isopropyl)amino)thiazol-5-yl)-8-phenylimidazo-[1,2-a]pyridine-2-carboxylate A solution of ethyl 6-(2-(tert-butoxycarbonyl-(isopropyl)amino)thiazol-5-yl)-8-phenylimidazo[1,2-a]pyridine-2-carboxylate (75 mg) in 4 ml of TFA was stirred at room temperature for 2 hours. The solvent was evaporated and the residue was purified by column chromatography on silica gel using ethyl acetate/hexane (50-100%) as eluent to give 50 mg of Ethyl 6-(2-(isopropylamino)thiazol-5-yl)-8-phenylimidazo[1,2-a]pyridine-2-carboxylate as a light yellow solid. LCMS (Conditions C): 2.90 min (RT); (M+H)+=407.33 (100%). ¹H NMR, 400 MHz, CDCl₃: δ 8.25 (s, 1 H), 8.16 (m, 1 H), 8.02 (m, 2 H), 7.52-7.43 (m, 3 H), 7.37 (d, 1H), 7.29 (s, 1H), 4.44 (q, J=7.1 Hz, 2 H), 3.60 (m, 1 H), 1.42 (m, 9 H).

Example 35

(6-(2-(Isopropylamino)thiazol-5-yl)-8-phenylimidazo[1,2-a]pyridin-2-yl)methanol

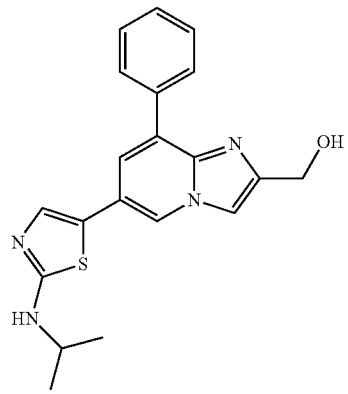 [SMILES: CC(C)Nc1ncc(-c2cc(-c3ccccc3)c3nc(CO)cn3c2)s1]

Step 1. Preparation of tert-butyl 5-(2-(hydroxymethyl)-8-phenylimidazo[1,2-a]pyridin-6-yl)thiazol-2-yl(isopropyl)carbamate

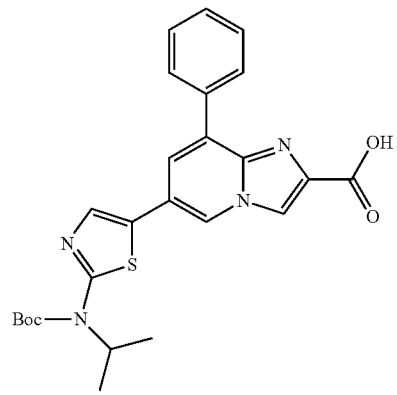 [SMILES: CC(C)N(C(=O)OC(C)(C)C)c1ncc(-c2cc(-c3ccccc3)c3nc(C(=O)O)cn3c2)s1]

A solution of ethyl 6-(2-(tert-butoxycarbonyl-(isopropyl)amino)thiazol-5-yl)-8-phenylimidazo[1,2-a]pyridine-2-carboxylate (100 mg, 0.2 mmol) in ether was cooled in an ice bath and treated with solid LAH (15 mg, 0.4 mmol). The mixture was stirred at 0° C. for 2 hours. The reaction was quenched with water, diluted with ethyl acetate and washed with water, brine and concentrated to give tert-butyl 5-(2-(hydroxymethyl)-8-phenylimidazo[1,2-a]pyridin-6-yl)thiazol-2-yl(isopropyl)carbamate. LCMS (Conditions C): 3.36 min (RT); (M+H)+=465.32 (100%).

Step 2. Preparation of (6-(2-(isopropylamino)thiazol-5-yl)-8-phenylimidazo[1,2-a]pyridin-2-yl)methanol A solution of tert-butyl 5-(2-(hydroxymethyl)-8-phenylimidazo[1,2-a]pyridin-6-yl)thiazol-2-yl(isopropyl)carbamate (75 mg) in 4 ml of TFA was stirred at room temperature for 2 hours. The solvent was evaporated and the residue was made basic with 1 N NaOH and extracted into CH₂Cl₂. The solvent was removed under vacuum and the residue purified by column chromatography on silica gel using ethyl acetate as eluent to give (6-(2-(isopropylamino)thiazol-5-yl)-8-phenylimidazo[1,2-a]pyridin-2-yl)methanol as a light yellow solid. LCMS (Conditions C): 1.82 min (RT); (M+H)$^+$= 365.31 (100%). $^1$H NMR, 400 MHz, CDCl$_3$/CD$_3$OD: δ 8.08 (d, 1 H), 7.89 (m, 2 H), 7.61-7.31 (m, 6 H), 4.74 (s, 2 H), 3.71 (m, 1 H), 1.32 (d, J=6.4 Hz, 6 H).

Example 36

6-(2-(Isopropylamino)thiazol-5-yl)-8-phenylimidazo[1,2-a]pyridine-2-carboxylic acid

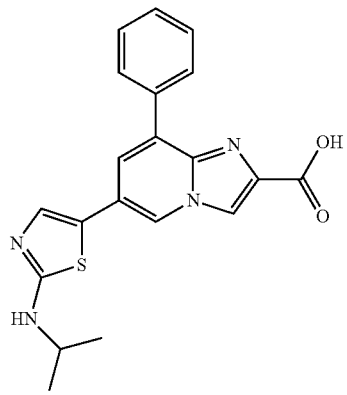 [SMILES: CC(C)Nc1ncc(-c2cc(-c3ccccc3)c3nc(C(=O)O)cn3c2)s1]

Step 1. Preparation of 6-(2-(tert-butoxycarbonyl(isopropyl)amino)thiazol-5-yl)-8-phenylimidazo[1,2-a]pyridine-2-carboxylic acid

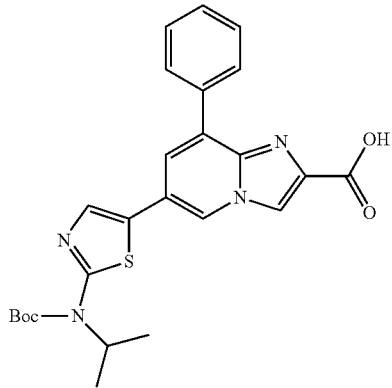 [SMILES: CC(C)N(C(=O)OC(C)(C)C)c1ncc(-c2cc(-c3ccccc3)c3nc(C(=O)O)cn3c2)s1]

A solution of ethyl 6-(2-(tert-butoxycarbonyl-(isopropyl)amino)thiazol-5-yl)-8-phenylimidazo[1,2-a]pyridine-2-carboxylate (1.00 g, 2.0 mmol) in THF/MeOH (2:1, 15 mL) was treated with 1 N NaOH (5 mL, 5 mmol) at room temperature for 5 hours. The organic solvents were removed under vacuum and the aqueous residue was acidified with 1 N HCl and the solids extracted into CH$_2$Cl$_2$. The extracts were washed with water and concentrated to give 940 mg of 6-(2-(tert-butoxycarbonyl(isopropyl)-amino)thiazol-5-yl)-8-phenylimidazo[1,2-a]pyridine-2-carboxylic acid as a yellow solid. LCMS (Conditions C): 3.98 min (RT); (M+H)$^+$=479.43 (100%).

Step 2. 6-(2-(Isopropylamino)thiazol-5-yl)-8-phenylimidazo[1,2-a]pyridine-2-carboxylic acid A solution of 6-(2-(tert-butoxycarbonyl(isopropyl)-amino)thiazol-5-yl)-8-phenyl-imidazo[1,2-a]pyridine-2-carboxylic acid (100 mg, 0.2 mmol) in 3 ml of TFA was stirred at room temperature for 2 hours. The solvent was removed under vacuum and the residue purified by HPLC to give 40 mg of 6-(2-(isopropylamino)thiazol-5-yl)-8-phenylimidazo[1,2-a]pyridine-2-carboxylic acid. LCMS (Conditions C): 2.27 min (RT); (M+H)$^+$=379.34 (100%). $^1$H NMR, 400 MHz, DMSO: δ 8.64 (s, 1 H), 8.52 (s, 1 H), 8.13 (d, J=7.3 Hz, 2 H), 7.83 (m, 2 H), 7.57-7.47 (m, 3 H), 3.87 (m, 1 H), 1.23 (d, J=6.5 Hz, 6 H).

Example 37

6-(2-(Isopropylamino)thiazol-5-yl)-N-methyl-8-phenylimidazo[1,2-a]pyridine-2-carboxamide

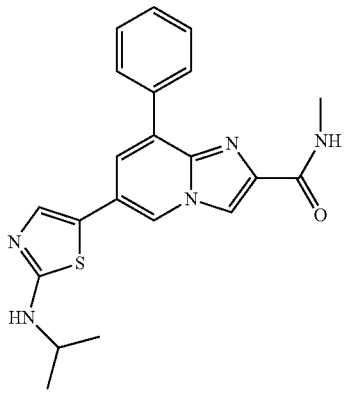 [SMILES: CNC(=O)c1cn2cc(-c3cnc(NC(C)C)s3)cc(-c3ccccc3)c2n1]

Step 1. Preparation of tert-butyl isopropyl(5-(2-(methylcarbamoyl)-8-phenylimidazo[1,2-a]pyridin-6-yl)thiazol-2-yl)carbamate

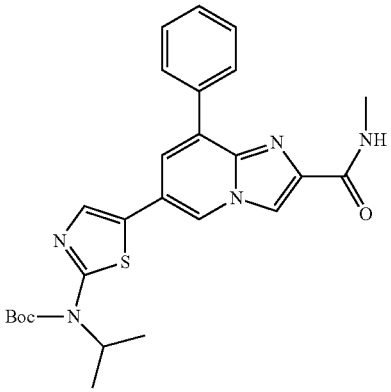 [SMILES: CNC(=O)c1cn2cc(-c3cnc(N(C(=O)OC(C)(C)C)C(C)C)s3)cc(-c3ccccc3)c2n1]

A solution of 6-(2-(tert-butoxycarbonyl(isopropyl)-amino)thiazol-5-yl)-8-phenylimidazo[1,2-a]pyridine-2-carboxylic acid (100 mg, 0.21 mmol) in dichloromethane was treated with EDC (48 mg, 0.25 mmol), HOBT (34 mg, 0.25 mmol), Et$_3$N (25 mg. 0.25 mmol), methylamine (2 M in THF: 3 ml, 6 mmol) and stirred at room temperature overnight. The reaction mixture was concentrated on a rotary evaporator and the residue purified by chromatography on silica gel using ethyl acetate/hexanes (50%) as eluent to give 30 mg (30% yield) of tert-butyl isopropyl(5-(2-(methylcarbamoyl)-8-phenylimidazo[1,2-a]pyridin-6-yl)thiazol-2-yl)carbamate as a white solid. LCMS (Conditions C): 4.26 min (RT); (M+H)$^+$=492.43 (100%).

Step 2. Preparation of 6-(2-(isopropylamino)thiazol-5-yl)-N-methyl-8-phenylimidazo[1,2-a]pyridine-2-carboxamide A solution of tert-butyl isopropyl(5-(2-(methylcarbamoyl)-8-phenylimidazo[1,2-a]pyridin-6-yl)thiazol-2-yl)carbamate (30 mg) in methylenechloride (2 ml) was treated with TFA (4 ml) and stirred at room temperature for 2 hours. The solvent was removed under vacuum and the residue chromatographed on silica gel using ethyl acetate as eluent to give 15 mg of 6-(2-(isopropylamino)thiazol-5-yl)-N-methyl-8-phenylimidazo[1,2-a]pyridine-2-carboxamide as a tan solid. LCMS (Conditions C): 2.62 min (RT); (M+H)$^+$=392.14 (100%). $^1$H NMR, 500 MHz, CDCl$_3$/CD$_3$OD: δ 8.20 (s, 1 H), 8.19 (d, J=1.65 Hz, 1 H), 7.89 (d, J=1.37 Hz, 1 H), 7.88 (s, 1 H), 7.42-7.53 (m, 3 H), 7.36 (d, J=1.92 Hz, 1 H), 7.34 (s, 1 H), 3.55-3.64 (m, 1 H), 1.34 (d, J=6.32 Hz, 6 H).

Examples 38 to 69

Additional compounds prepared according to the general methods outlined above are included in Table 2.

TABLE 2

| Example No. | Structure | LCMS | HPLC rt |
| --- | --- | --- | --- |
| 38 | 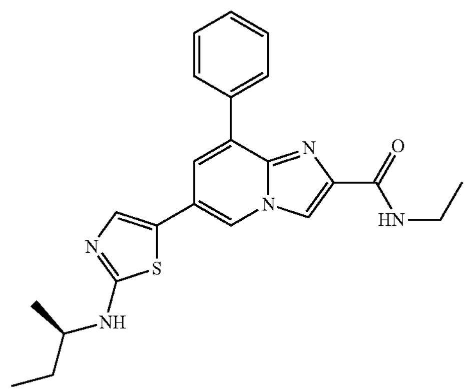 [SMILES: CCNC(=O)c1cn2cc(-c3cnc(N[C@H](C)CC)s3)cc(-c3ccccc3)c2n1] | 420.3 | 3.88, B |
| 39 | 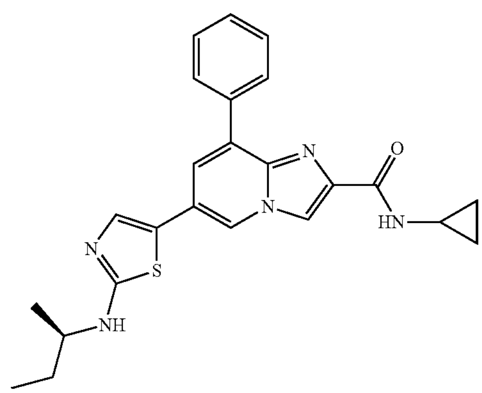 [SMILES: CC[C@@H](C)Nc1ncc(-c2cc(-c3ccccc3)c3nc(C(=O)NC4CC4)cn3c2)s1] | 432.4 | 3.97, B |
| 41 | 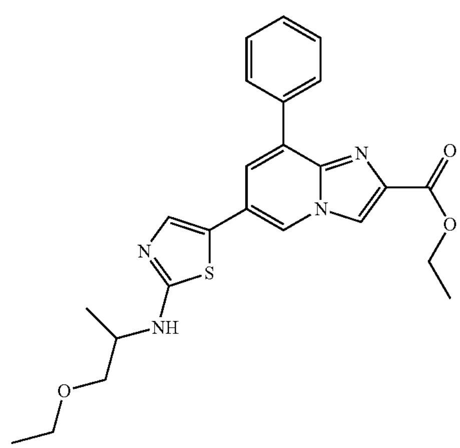 [SMILES: CCOCC(C)Nc1ncc(-c2cc(-c3ccccc3)c3nc(C(=O)OCC)cn3c2)s1] | 451.3 | 3.90, C |

TABLE 2-continued

| Example No. | Structure | LCMS | HPLC rt |
|---|---|---|---|
| 45 | 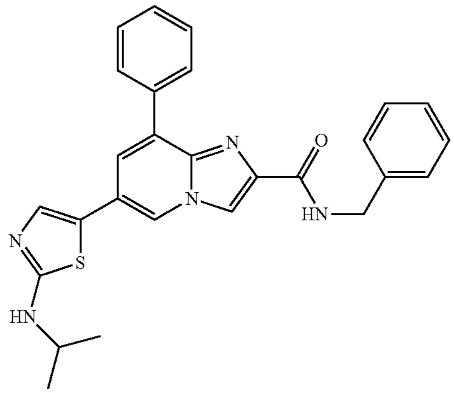 [SMILES: CC(C)Nc1ncc(-c2cc(-c3ccccc3)c3nc(C(=O)NCc4ccccc4)cn3c2)s1] | 468.4 | 3.36, C |
| 47 | 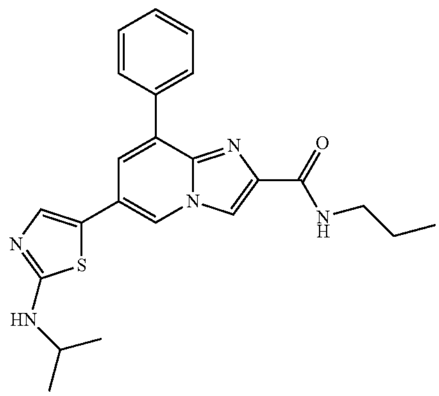 [SMILES: CCCNC(=O)c1cn2cc(-c3cnc(NC(C)C)s3)cc(-c3ccccc3)c2n1] | 420.4 | 3.11, C |
| 48 | 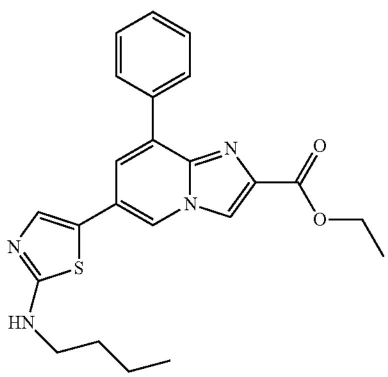 [SMILES: CCCCNc1ncc(-c2cc(-c3ccccc3)c3nc(C(=O)OCC)cn3c2)s1] | 421.3 | 3.17, C |
| 49 | 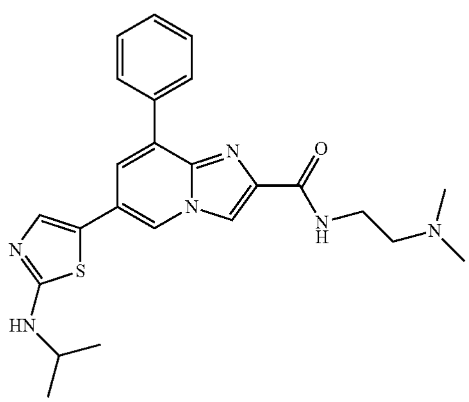 [SMILES: CC(C)Nc1ncc(-c2cc(-c3ccccc3)c3nc(C(=O)NCCN(C)C)cn3c2)s1] | 449.4 | 2.14, C |

TABLE 2-continued

| Example No. | Structure | LCMS | HPLC rt |
|---|---|---|---|
| 50 | 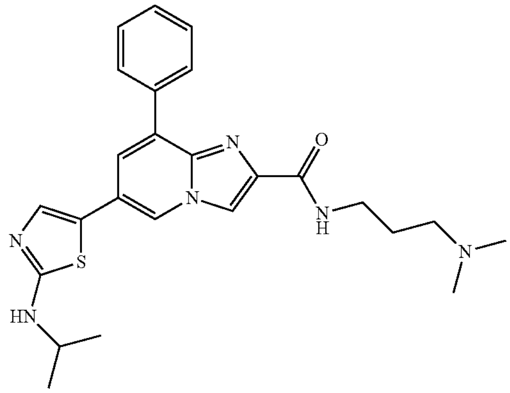 [SMILES: CC(C)Nc1ncc(-c2cc(-c3ccccc3)c3nc(C(=O)NCCCN(C)C)cn3c2)s1] | 463.5 | 2.17, C |
| 51 | 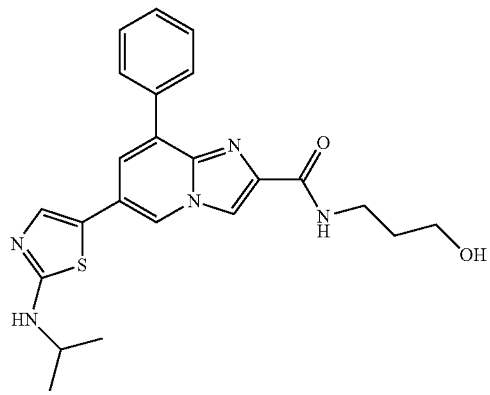 [SMILES: CC(C)Nc1ncc(-c2cc(-c3ccccc3)c3nc(C(=O)NCCCO)cn3c2)s1] | 436.4 | 2.63, C |
| 52 | 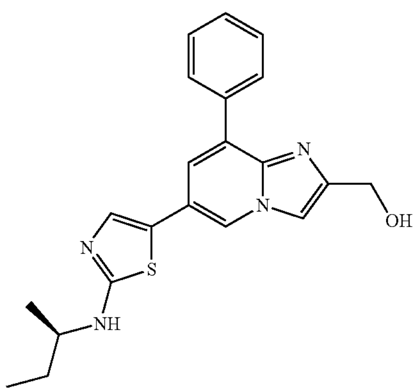 [SMILES: CC[C@@H](C)Nc1ncc(-c2cc(-c3ccccc3)c3nc(CO)cn3c2)s1] | 379.4 | 1.99, C |
| 53 | 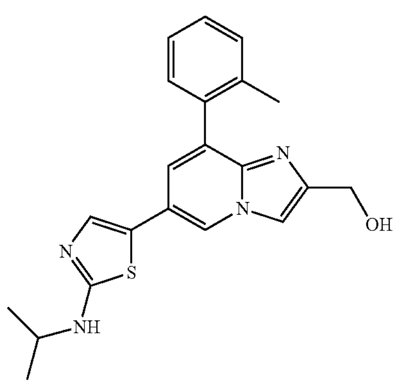 [SMILES: Cc1ccccc1-c1cc(-c2cnc(NC(C)C)s2)cn2cc(CO)nc12] | 379.4 | 1.90, C |

TABLE 2-continued

| Example No. | Structure | LCMS | HPLC rt |
|---|---|---|---|
| 54 | 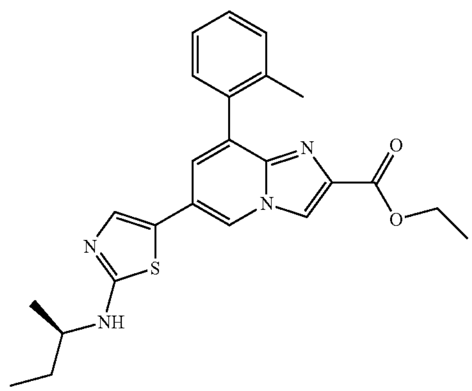 [SMILES: CCOC(=O)c1cn2cc(-c3cnc(N[C@H](C)CC)s3)cc(-c3ccccc3C)c2n1] | 435.4 | 3.01, C |
| 55 | 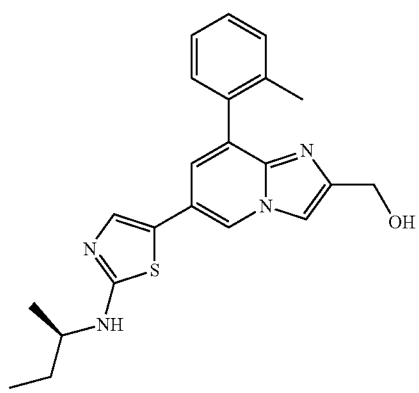 [SMILES: CC[C@@H](C)Nc1ncc(-c2cc(-c3ccccc3C)c3nc(CO)cn3c2)s1] | 393.4 | 2.10, C |
| 56 | 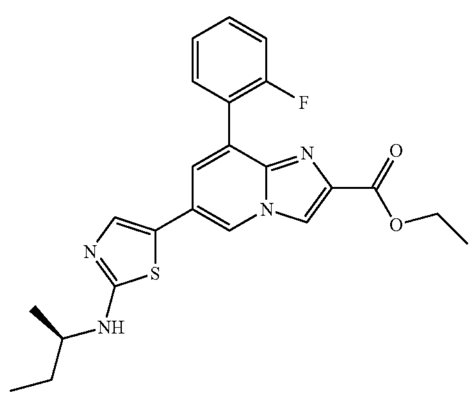 [SMILES: CCOC(=O)c1cn2cc(-c3cnc(N[C@H](C)CC)s3)cc(-c3ccccc3F)c2n1] | 439.4 | 2.95, C |
| 57 | 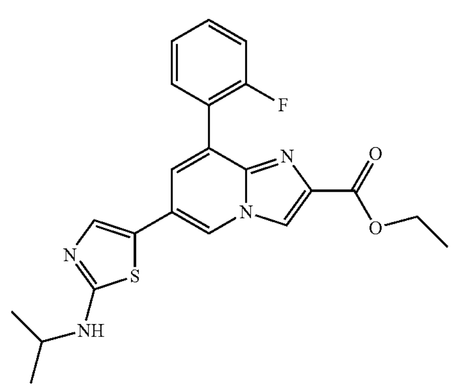 [SMILES: CCOC(=O)c1cn2cc(-c3cnc(NC(C)C)s3)cc(-c3ccccc3F)c2n1] | 425.4 | 2.78, C |

TABLE 2-continued

| Example No. | Structure | LCMS | HPLC rt |
|---|---|---|---|
| 58 | 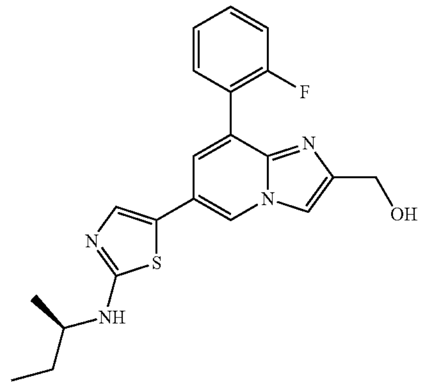 [SMILES: CC[C@@H](C)Nc1ncc(-c2cc(-c3ccccc3F)c3nc(CO)cn3c2)s1] | 397.4 | 1.32, C |
| 59 | 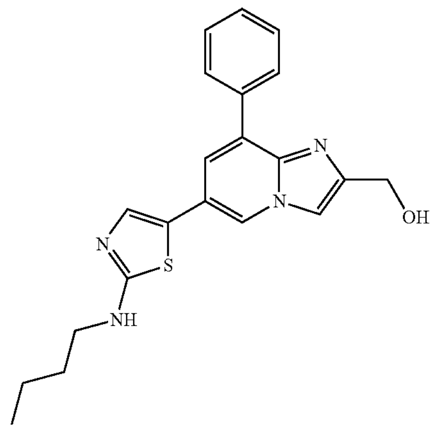 [SMILES: CCCCNc1ncc(-c2cc(-c3ccccc3)c3nc(CO)cn3c2)s1] | 379.4 | 2.15, C |
| 60 | 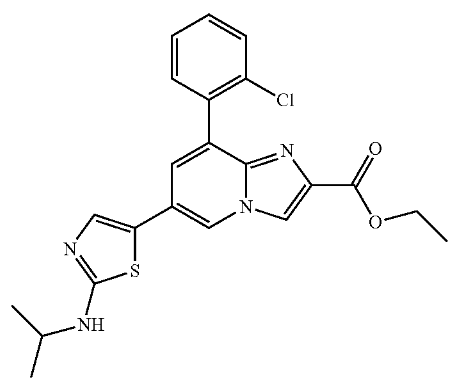 [SMILES: CCOC(=O)c1cn2cc(-c3cnc(NC(C)C)s3)cc(-c3ccccc3Cl)c2n1] | 440.9 | 2.89, C |
| 61 | 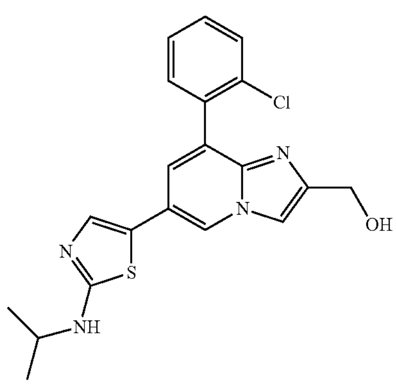 [SMILES: CC(C)Nc1ncc(-c2cc(-c3ccccc3Cl)c3nc(CO)cn3c2)s1] | 399.0 | 2.00, C |

TABLE 2-continued

| Example No. | Structure | LCMS | HPLC rt |
|---|---|---|---|
| 62 | 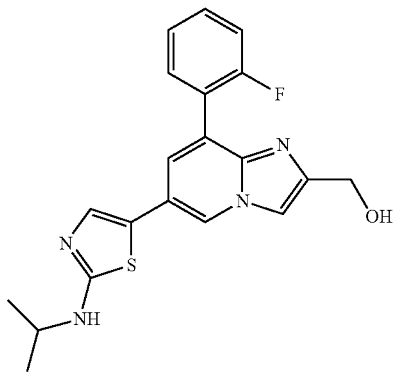 [SMILES: CC(C)Nc1ncc(-c2cc(-c3ccccc3F)c3nc(CO)cn3c2)s1] | 383.0 | 1.83, C |
| 63 | 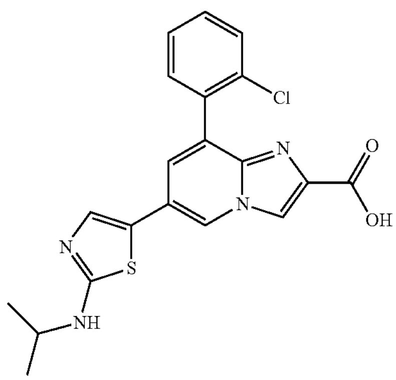 [SMILES: CC(C)Nc1ncc(-c2cc(-c3ccccc3Cl)c3nc(C(=O)O)cn3c2)s1] | 412.9 | 2.34, C |
| 64 | 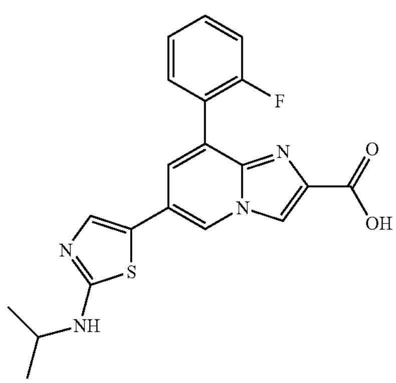 [SMILES: CC(C)Nc1ncc(-c2cc(-c3ccccc3F)c3nc(C(=O)O)cn3c2)s1] | 397.0 | 2.22, C |
| 65 | 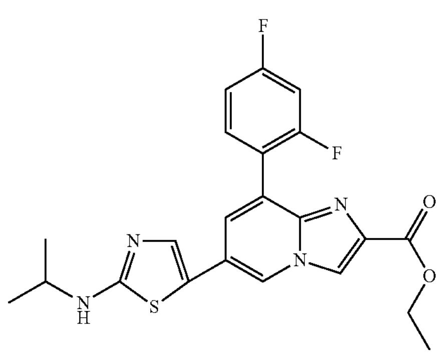 [SMILES: CCOC(=O)c1cn2cc(-c3cnc(NC(C)C)s3)cc(-c3ccc(F)cc3F)c2n1] | 443.3 | 2.9, C |

TABLE 2-continued

| Example No. | Structure | LCMS | HPLC rt |
|---|---|---|---|
| 66 | 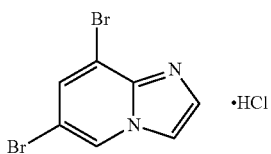 | 401.3 | 1.93, C |
| 67 | 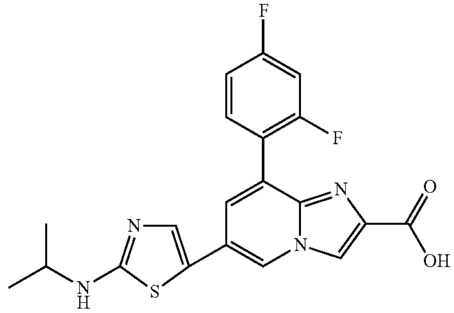 [SMILES: CC(C)Nc1ncc(-c2cc(-c3ccc(F)cc3F)c3nc(C(=O)O)cn3c2)s1] | 415.2 | 2.37, C |

Preparation of 6,8-dibromoH-imidazo[1,2-a]pyridine hydrochloride

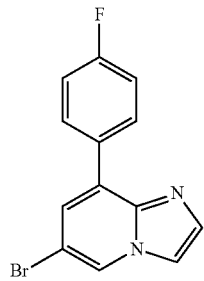 [SMILES: Fc1ccc(-c2cc(Br)cn3ccnc23)cc1]

·HCl

A mixture of 3,5-dibromopyridin-2-amine (9.03 g, 35.8 mmol) and chloroacetonaldehyde (50% in H₂O, 9.1 mL, 71.6 mmol) in ethanol (50 mL) was heated at 50° C. overnight, cooled and concentrated. The residue was added acetone (20 mL) and stirred rapidly for 2 h. The solid was filtered and dried to give 6,8-dibromoH-imidazo[1,2-a]pyridine hydrochloride (1) (9.7 g, 75.9% yield).

Preparation of 6-bromo-8-(4-fluorophenyl)H-imidazo[1,2-a]pyridine

A solution of 6,8-dibromoH-imidazo[1,2-a]pyridine hydrochloride (1.51 g, 4.8 mmol) and 4-fluorophenylboronic acid (0.67 g, 4.84 mmol) in toluene (10 mL) and ethanol (0.5 mL) was degassed via nitrogen bubble for 20 mins. The mixture was then added Pd(PPh₃)₄ (279 mg, 0.242 mmol) and K₃PO₄ (2 M, 7.26 mL, 14.5 mmol) and heated at 80° C. overnight. The reaction was cooled, poured into ethyl acetate (200 mL), washed with brine, separated, dried over Na₂SO₄ and concentrated. The residue was purified by a flash column using ethyl acetate in hexanes (8%) as an eluent. The product containing fractions were concentrated to a solid which was titrated with dichloromethane (10 mL) and filtered to give a yellow solid (0.56 g, 39.8% yield).

Preparation of 5-bromo-3-(2,4-difluorophenyl)pyridin-2-amine

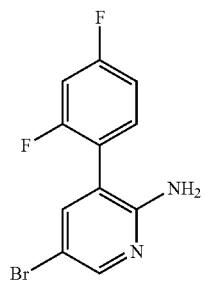 [SMILES: Nc1ncc(Br)cc1-c1ccc(F)cc1F]

A solution of 3,5-dibromopyridin-2-amine (2.95 g, 11.71 mmol) and 2,4-difluorophenylboronic acid (1.85 g, 11.71 mmol) in toluene was degassed via nitrogen bubble for 20 mins. The mixture was then added Pd(PPh₃)₄ (0.677 g, 0.585 mmol), K₃PO₄ (2 M, 11.8 mL, 23.4 mmol) and Ethanol (1 mL) and heated at 80° C. overnight. The reaction was cooled, poured into ethyl acetate (150 mL), washed with brine, separated, dried over Na₂SO₄ and concentrated to give a crude 5-bromo-3-(2,4-difluorophenyl)pyridin-2-amine (3) which was used directly in next step without purification.

Preparation of 6-bromo-8-(2,4-difluorophenyl)H-imidazo[1,2-a]pyridine

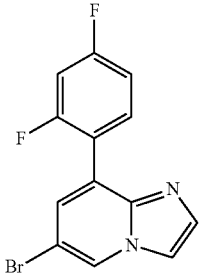 [SMILES: Fc1ccc(-c2cc(Br)cn3ccnc23)c(F)c1]

A solution of 5-bromo-3-(2,4-difluorophenyl)pyridin-2-amine (2) (crude, 0.93 g, 3.26 mmol) and chloroacetaldehyde (0.54 mL, 4.24 mmol) in ethanol (15 mL) was heated at 60° C. overnight. The reaction was cooled, concentrated and added ethyl acetate (150 mL). The mixture was washed with brine (50 ml), separated, dried over $Na_2SO_4$ and concentrated. The residue was purified by a flash column using ethyl acetate in hexanes (8%) as an eluent to give an off-white solid (4) (0.54 g, 53.6% yield).

Preparation of 8-(2,4-difluorophenyl)H-imidazo[1,2-a]pyridin-6-ylboronic acid

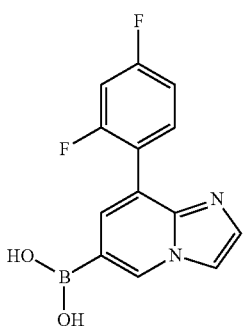 [SMILES: OB(O)c1cc(-c2ccc(F)cc2F)c2nccn2c1]

A solution of 6-bromo-8-(2,4-difluorophenyl)H-imidazo[1,2-a]pyridine (4) (185 mg, 0.599 mmol) and triisopropyl borate (165 μL, 0.718 mmol) in THF (10 mL) was degassed via nitrogen bubble for 20 mins and was added n-BuLi (2.5 M, 287 μL, 0.718 mmol) at −78° C. under nitrogen. The mixture was stirred at −40° C. for 1 h, then warm to room temperature gradually and quenched with HCl (2 N, 4 mL). The mixture was stirred for 2 h at rt, neutralized by aqueous NaOH (4 N), extracted with THF (3×20 mL). The organic layer was dried over and concentrated. The residue was added acetonitrile (5 mL), sonicated and stirred for 2 h. The solid was filtered, rinsed with acetonitrile and dried to give 8-(2,4-difluorophenyl)H-imidazo[1,2-a]pyridin-6-ylboronic acid (5) (146 mg, 88.9% yield).

Example 70

Preparation of 5-(8-(2,4-difluorophenyl)H-imidazo[1,2-a]pyridin-6-yl)-N-(3-methylbutan-2-yl)thiazol-2-amine

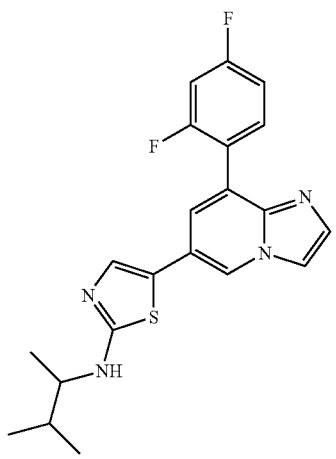 [SMILES: CC(C)C(C)Nc1ncc(-c2cc(-c3ccc(F)cc3F)c3nccn3c2)s1]

A solution of 8-(2,4-difluorophenyl)H-imidazo[1,2-a]pyridin-6-ylboronic acid (5) (20 mg, 0.073 mmol) and tert-butyl 5-bromothiazol-2-yl(3-methylbutan-2-yl)carbamate (25 mg, 0.073 mmol) in toluene (2 mL) and ethanol (100 μL) was degassed via nitrogen bubble for 20 mins. The mixture was then added Pb(PPh$_3$)$_4$ (4.2 mg, 0.00365 mmol) and $K_3PO_4$ (2 M, 73 μL, 0.146 mmol) and heated to 80° C. overnight. The reaction was cooled and extracted with ethyl acetate (2×10 mL), washed with brine, dried over and concentrated. The residue was purified via a flash column using a gradient of ethyl acetate in hexanes (10-40%). The product containing fractions were concentrated and was added dichloromethane (2 mL) and TFA (500 μL). The mixture was stirred at rt for 4 h and concentrated. The residue was purified directly by reverse phase preparative HPLC and the product containing fractions were concentrated and neutralized with aqueous $NaHCO_3$ to precipitate the products. The solids were filtered, washed and dried to give 5-(8-(2,4-difluorophenyl)H-imidazo[1,2-a]pyridin-6-yl)-N-(3-methylbutan-2-yl)thiazol-2-amine (6) (10 mg, 34.4% yield).

Examples 71 to 160

Additional compounds prepared according to the general methods outlined above are included in Table 3.

TABLE 3

| Example No. | Structure | LCMS | HPLC Tr (min) |
|---|---|---|---|
| 71 | 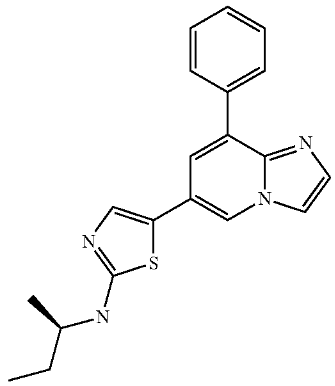 [SMILES: CC[C@@H](C)Nc1ncc(-c2cc(-c3ccccc3)c3nccn3c2)s1] | 349.22 | 2.67, B |
| 72 | 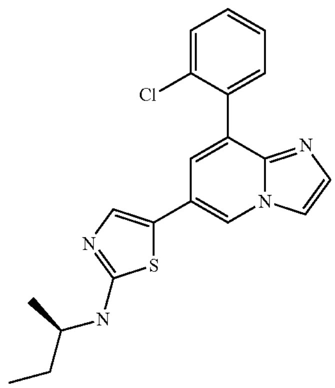 [SMILES: CC[C@@H](C)Nc1ncc(-c2cc(-c3ccccc3Cl)c3nccn3c2)s1] | 385.17 | 2.92, B |
| 73 | 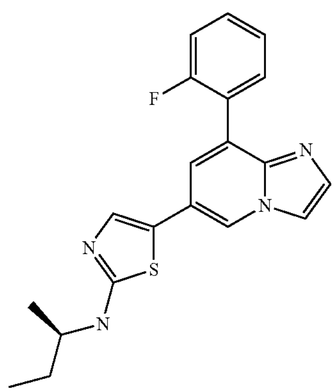 [SMILES: CC[C@@H](C)Nc1ncc(-c2cc(-c3ccccc3F)c3nccn3c2)s1] | 367.23 | 2.73, B |
| 74 | 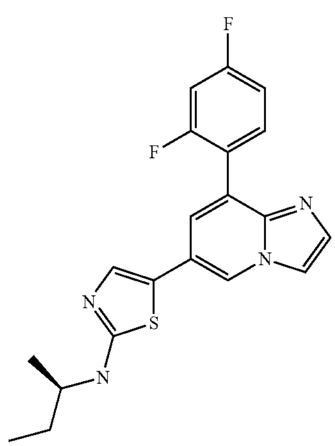 [SMILES: CC[C@@H](C)Nc1ncc(-c2cc(-c3ccc(F)cc3F)c3nccn3c2)s1] | 385.22 | 2.73, B |

| Example No. | Structure | LCMS | HPLC Tr (min) |
|---|---|---|---|
| 75 | 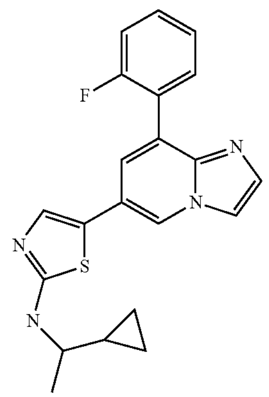 [SMILES: CC(Nc1ncc(-c2cc(-c3ccccc3F)c3nccn3c2)s1)C1CC1] | 379.22 | 2.82, B |
| 76 | 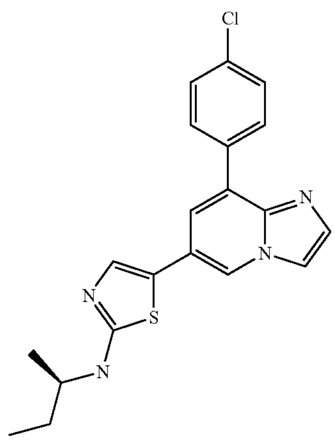 [SMILES: CC[C@@H](C)Nc1ncc(-c2cc(-c3ccc(Cl)cc3)c3nccn3c2)s1] | 383.22 | 3.02, B |
| 77 | 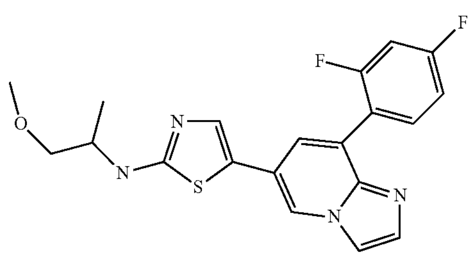 [SMILES: COCC(C)Nc1ncc(-c2cc(-c3ccc(F)cc3F)c3nccn3c2)s1] | 401.2 | 2.40, B |
| 78 | 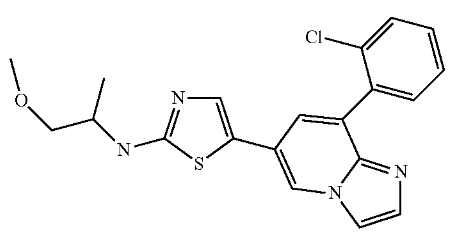 [SMILES: COCC(C)Nc1ncc(-c2cc(-c3ccccc3Cl)c3nccn3c2)s1] | 399.2 | 2.48, B |
| 79 | 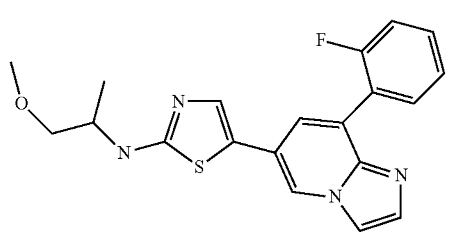 [SMILES: COCC(C)Nc1ncc(-c2cc(-c3ccccc3F)c3nccn3c2)s1] | 383.2 | 2.32, B |

TABLE 3-continued

| Example No. | Structure | LCMS | HPLC Tr (min) |
|---|---|---|---|
| 80 | 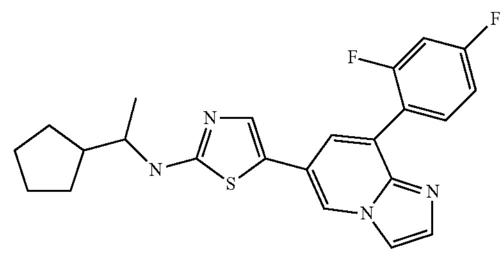 [SMILES: CC(Nc1ncc(-c2cc(-c3ccc(F)cc3F)c3nccn3c2)s1)C1CCCC1] | 425.2 | 3.17, B |
| 81 | 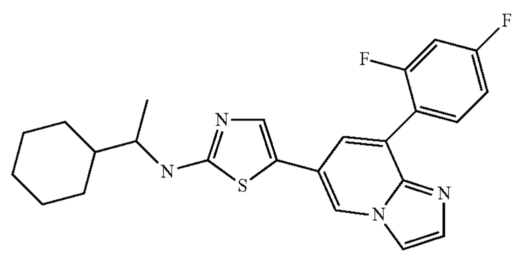 [SMILES: CC(Nc1ncc(-c2cc(-c3ccc(F)cc3F)c3nccn3c2)s1)C1CCCCC1] | 439.2 | 3.42, B |
| 82 | 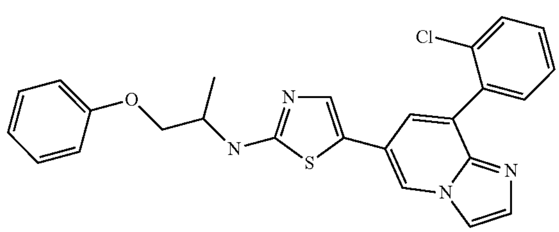 [SMILES: CC(COc1ccccc1)Nc1ncc(-c2cc(-c3ccccc3Cl)c3nccn3c2)s1] | 461.2 | 3.30, B |
| 83 | 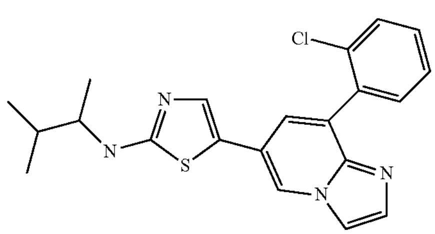 [SMILES: CC(C)C(C)Nc1ncc(-c2cc(-c3ccccc3Cl)c3nccn3c2)s1] | 397.2 | 2.90, B |
| 84 | 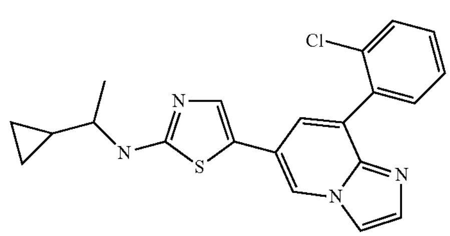 [SMILES: CC(Nc1ncc(-c2cc(-c3ccccc3Cl)c3nccn3c2)s1)C1CC1] | 395.2 | 2.75, B |
| 85 | 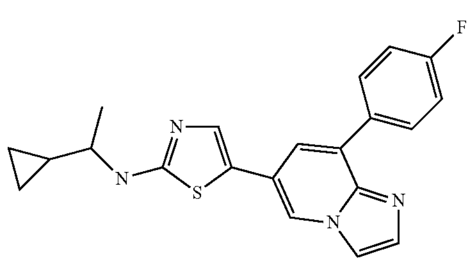 [SMILES: CC(Nc1ncc(-c2cc(-c3ccc(F)cc3)c3nccn3c2)s1)C1CC1] | 379.3 | 2.80, B |

TABLE 3-continued

| Example No. | Structure | LCMS | HPLC Tr (min) |
|---|---|---|---|
| 86 | 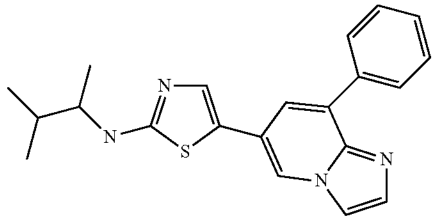 [SMILES: CC(C)C(C)Nc1ncc(-c2cc(-c3ccccc3)c3nccn3c2)s1] | 363.3 | 2.64, B |
| 87 | 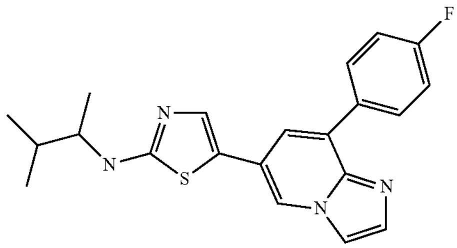 [SMILES: CC(C)C(C)Nc1ncc(-c2cc(-c3ccc(F)cc3)c3nccn3c2)s1] | 381.3 | 2.71, B |
| 88 | 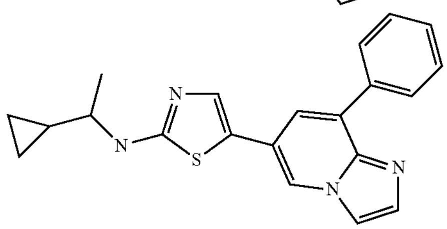 | 361.3 | 2.57, B |
| 89 | 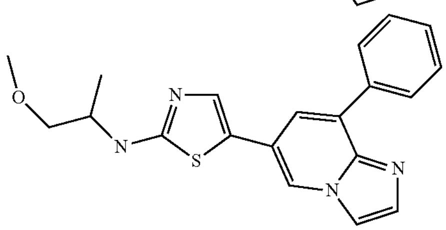 | 353.17 | 2.85, B |
| 90 | 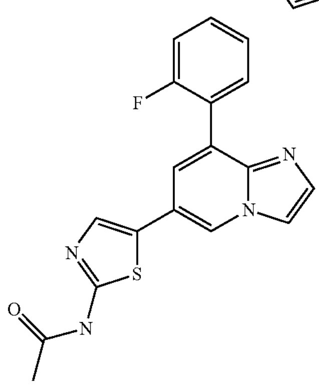 | 353.17 | 2.85, B |
| 91 | 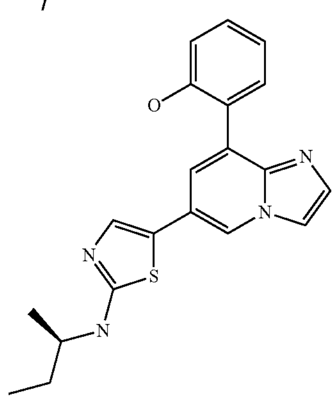 | 365.25 | 2.51, B |

TABLE 3-continued
| Example No. | Structure | LCMS | HPLC Tr (min) |
|---|---|---|---|
| 92 | 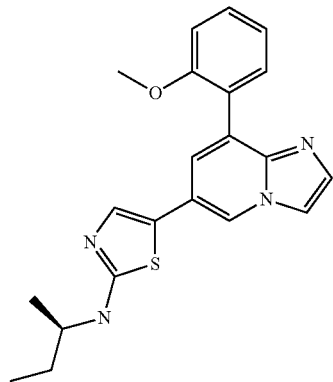 [SMILES: CC[C@@H](C)Nc1ncc(-c2cc(-c3ccccc3OC)c3nccn3c2)s1] | 379.21 | 2.77, B |
| 94 | 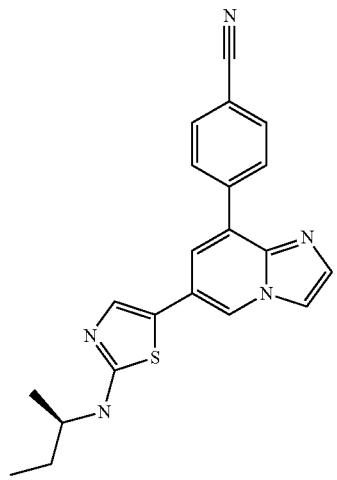 [SMILES: CC[C@@H](C)Nc1ncc(-c2cc(-c3ccc(C#N)cc3)c3nccn3c2)s1] | 374.16 | 2.53, B |
| 95 | 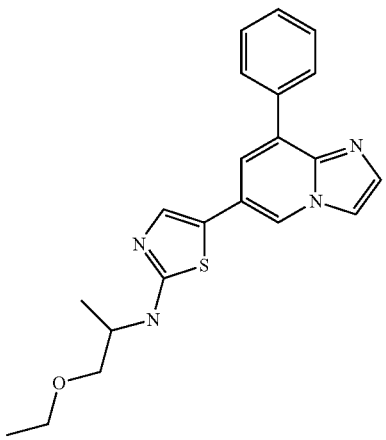 [SMILES: CCOCC(C)Nc1ncc(-c2cc(-c3ccccc3)c3nccn3c2)s1] | 379.24 | 2.66, B |

TABLE 3-continued
| Example No. | Structure | LCMS | HPLC Tr (min) |
|---|---|---|---|
| 96 | 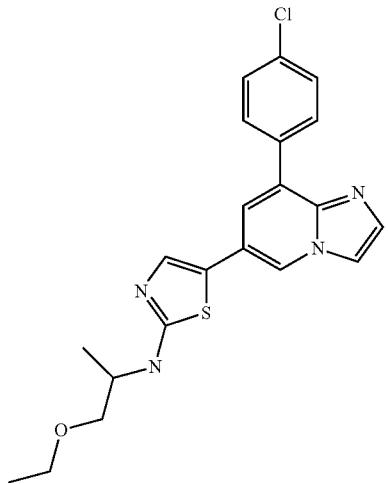 [SMILES: CCOCC(C)Nc1ncc(-c2cc(-c3ccc(Cl)cc3)c3nccn3c2)s1] | 413.17 | 3.03, B |
| 97 | 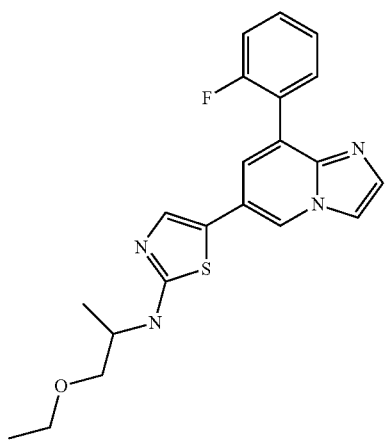 [SMILES: CCOCC(C)Nc1ncc(-c2cc(-c3ccccc3F)c3nccn3c2)s1] | 397.23 | 2.69, B |
| 98 | 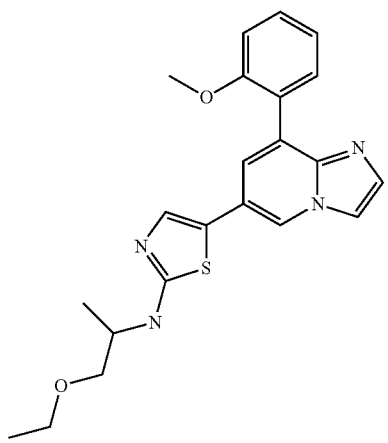 [SMILES: CCOCC(C)Nc1ncc(-c2cc(-c3ccccc3OC)c3nccn3c2)s1] | 409.21 | 2.81, B |

TABLE 3-continued
| Example No. | Structure | LCMS | HPLC Tr (min) |
|---|---|---|---|
| 101 | 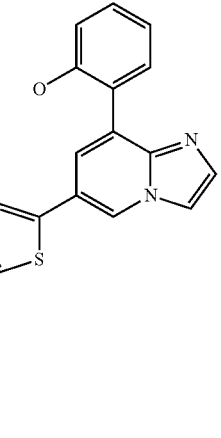 | 395.22 | 2.53, B |
| 102 | 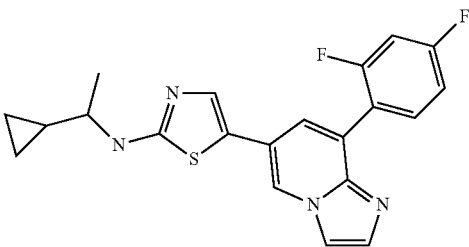 [SMILES: CC(Nc1ncc(-c2cc(-c3ccc(F)cc3F)c3nccn3c2)s1)C1CC1] | 397.2 | 2.68, B |
| 103 | 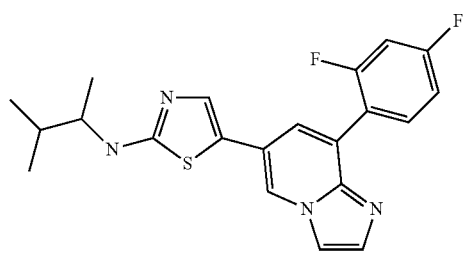 [SMILES: CC(C)C(C)Nc1ncc(-c2cc(-c3ccc(F)cc3F)c3nccn3c2)s1] | 399.2 | 2.82, B |
| 104 | 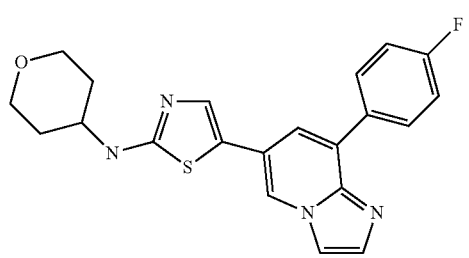 [SMILES: Fc1ccc(-c2cc(-c3cnc(NC4CCOCC4)s3)cn3ccnc23)cc1] | 395.2 | 3.5, B |
| 105 | 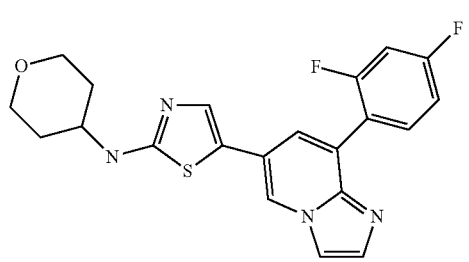 [SMILES: Fc1ccc(-c2cc(-c3cnc(NC4CCOCC4)s3)cn3ccnc23)c(F)c1] | 413.2 | 3.5, B |

TABLE 3-continued

| Example No. | Structure | LCMS | HPLC Tr (min) |
|---|---|---|---|
| 106 | 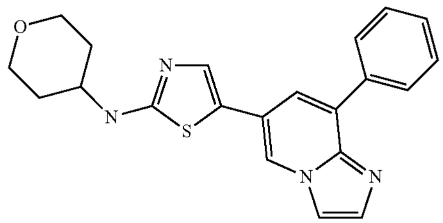 [SMILES: c1ccc(-c2cc(-c3cnc(NC4CCOCC4)s3)cn3ccnc23)cc1] | 377.3 | 2.28, B |
| 107 | 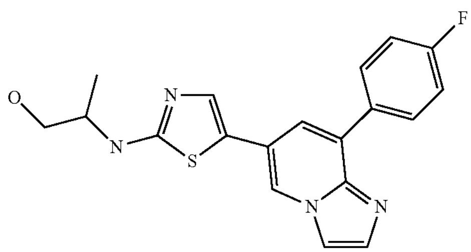 [SMILES: CC(CO)Nc1ncc(-c2cc(-c3ccc(F)cc3)c3nccn3c2)s1] | 369.2 | 1.89, B |
| 108 | 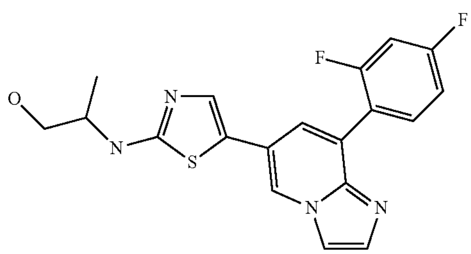 [SMILES: CC(CO)Nc1ncc(-c2cc(-c3ccc(F)cc3F)c3nccn3c2)s1] | 387.2 | 1.99, B |
| 109 | 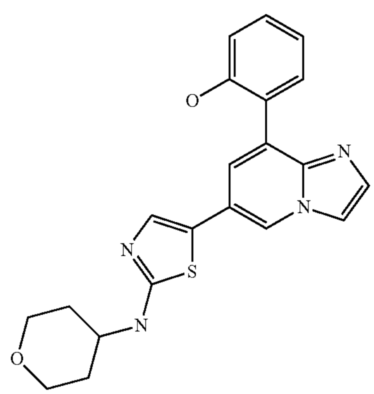 | 393.24 | 2.34, B |
| 110 | 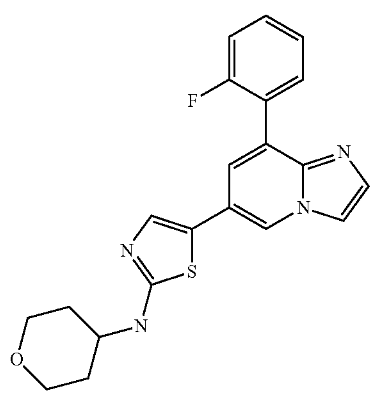 [SMILES: Oc1ccccc1-c1cc(-c2cnc(NC3CCOCC3)s2)cn2ccnc12] | 395.23 | 2.5, B |

TABLE 3-continued

| Example No. | Structure | LCMS | HPLC Tr (min) |
|---|---|---|---|
| 112 | 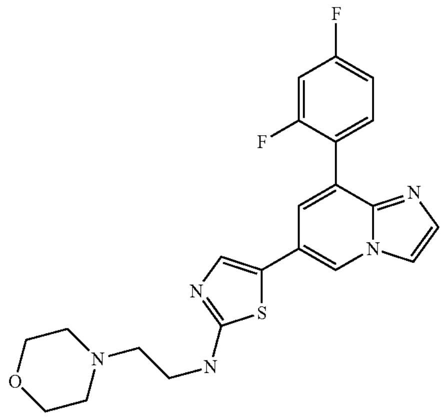 [SMILES: Fc1ccc(-c2cc(-c3cnc(NCCN4CCOCC4)s3)cn3ccnc23)c(F)c1] | 442.29 | 2.05, B |
| 113 | 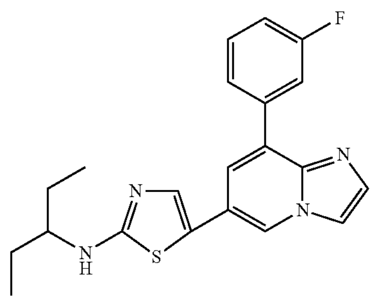 [SMILES: CCC(CC)Nc1ncc(-c2cc(-c3cccc(F)c3)c3nccn3c2)s1] | 381.3 | 2.22, C |
| 114 | 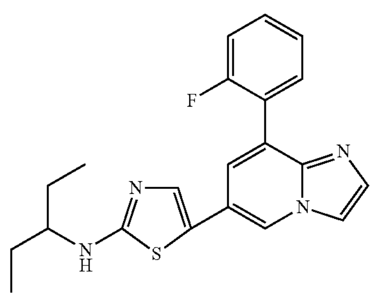 [SMILES: CCC(CC)Nc1ncc(-c2cc(-c3ccccc3F)c3nccn3c2)s1] | 381.3 | 2.23, C |
| 115 | 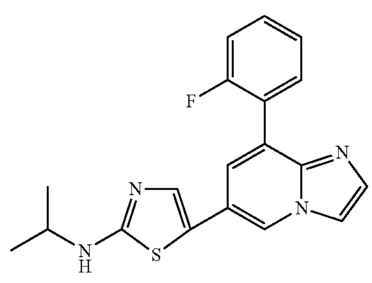 [SMILES: CC(C)Nc1ncc(-c2cc(-c3ccccc3F)c3nccn3c2)s1] | 353.3 | 1.85, C |
| 116 | 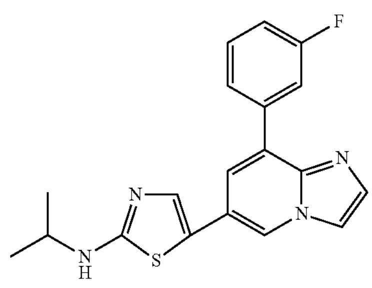 [SMILES: CC(C)Nc1ncc(-c2cc(-c3cccc(F)c3)c3nccn3c2)s1] | 353.4 | 1.84, C |

TABLE 3-continued
| Example No. | Structure | LCMS | HPLC Tr (min) |
|---|---|---|---|
| 117 | 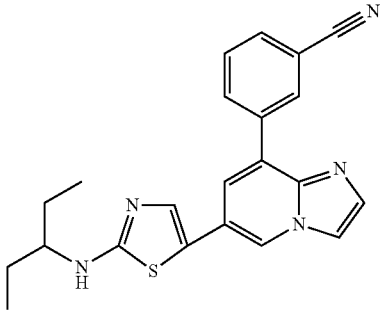 [SMILES: CCC(CC)Nc1ncc(-c2cc(-c3cccc(C#N)c3)c3nccn3c2)s1] | 388.4 | 2.07, C |
| 118 | 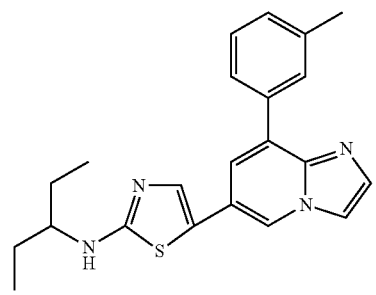 [SMILES: CCC(CC)Nc1ncc(-c2cc(-c3cccc(C)c3)c3nccn3c2)s1] | 377.4 | 2.47, C |
| 119 | 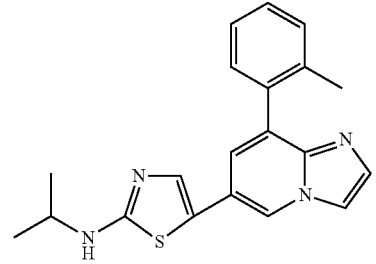 [SMILES: Cc1ccccc1-c1cc(-c2cnc(NC(C)C)s2)cn2ccnc12] | 349.4 | 1.93, C |
| 120 | 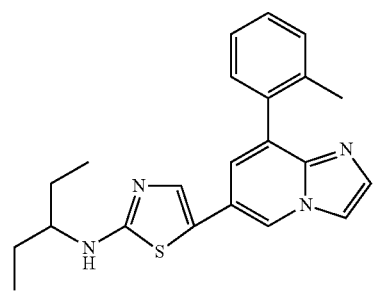 [SMILES: CCC(CC)Nc1ncc(-c2cc(-c3ccccc3C)c3nccn3c2)s1] | 377.4 | 2.32, C |
| 121 | 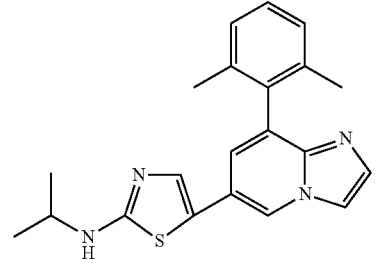 [SMILES: Cc1cccc(C)c1-c1cc(-c2cnc(NC(C)C)s2)cn2ccnc12] | 363.4 | 2.05, C |

TABLE 3-continued

| Example No. | Structure | LCMS | HPLC Tr (min) |
|---|---|---|---|
| 122 | 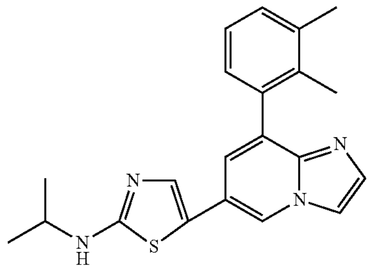 [SMILES: Cc1cccc(-c2cc(-c3cnc(NC(C)C)s3)cn3ccnc23)c1C] | 363.4 | 2.19, C |
| 123 | 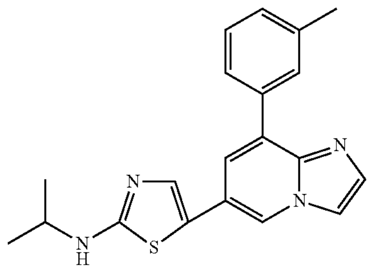 [SMILES: Cc1cccc(-c2cc(-c3cnc(NC(C)C)s3)cn3ccnc23)c1] | 349.3 | 2.11, C |
| 124 | 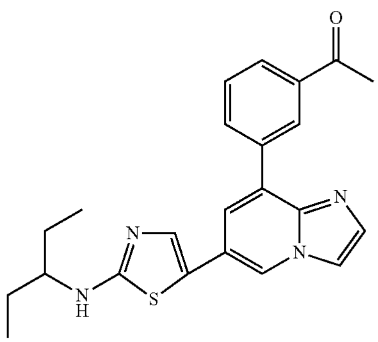 [SMILES: CCC(CC)Nc1ncc(-c2cc(-c3cccc(C(C)=O)c3)c3nccn3c2)s1] | 405.3 | 2.15, C |
| 125 | 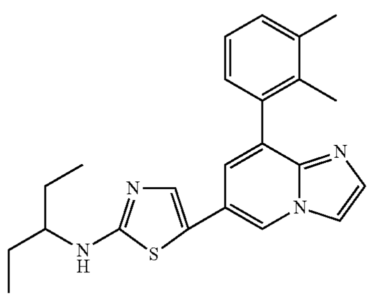 [SMILES: CCC(CC)Nc1ncc(-c2cc(-c3cccc(C)c3C)c3nccn3c2)s1] | 391.4 | 2.56, C |
| 126 | 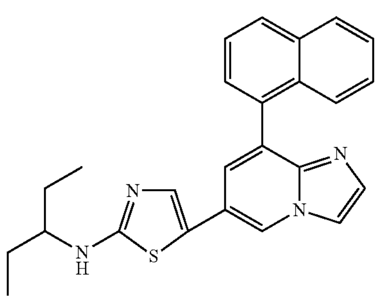 [SMILES: CCC(CC)Nc1ncc(-c2cc(-c3cccc4ccccc34)c3nccn3c2)s1] | 413.4 | 2.58, C |

TABLE 3-continued

| Example No. | Structure | LCMS | HPLC Tr (min) |
|---|---|---|---|
| 127 | 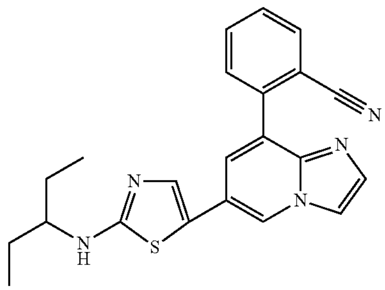 [SMILES: CCC(CC)Nc1ncc(-c2cc(-c3ccccc3C#N)c3nccn3c2)s1] | 388.4 | 2.05, C |
| 128 | 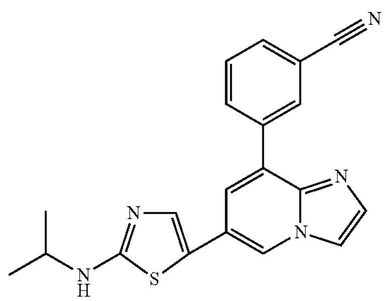 [SMILES: CC(C)Nc1ncc(-c2cc(-c3cccc(C#N)c3)c3nccn3c2)s1] | 360.3 | 1.7, C |
| 129 | 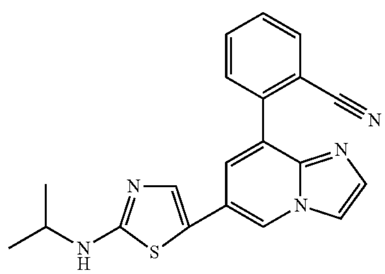 [SMILES: CC(C)Nc1ncc(-c2cc(-c3ccccc3C#N)c3nccn3c2)s1] | 360.3 | 1.68, C |
| 130 | 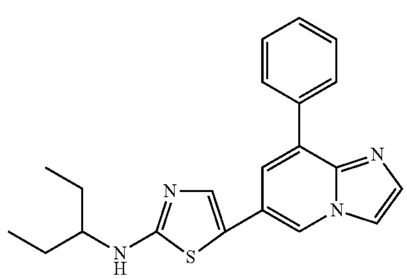 [SMILES: CCC(CC)Nc1ncc(-c2cc(-c3ccccc3)c3nccn3c2)s1] | 363.3 | 2.67, C |
| 131 | 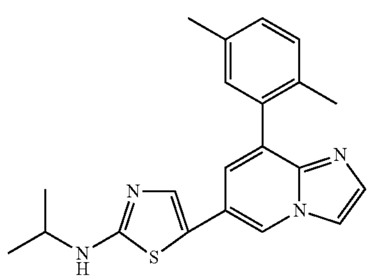 [SMILES: Cc1ccc(C)c(-c2cc(-c3cnc(NC(C)C)s3)cn3ccnc23)c1] | 363.3 | 2.71, C |

TABLE 3-continued

| Example No. | Structure | LCMS | HPLC Tr (min) |
|---|---|---|---|
| 132 | 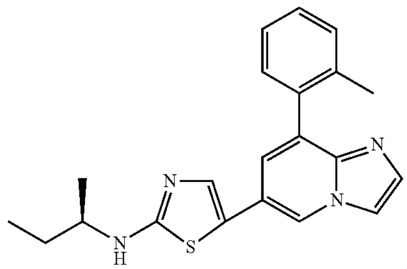 [SMILES: CC[C@@H](C)Nc1ncc(-c2cc(-c3ccccc3C)c3nccn3c2)s1] | 363.4 | 2.13, C |
| 133 | 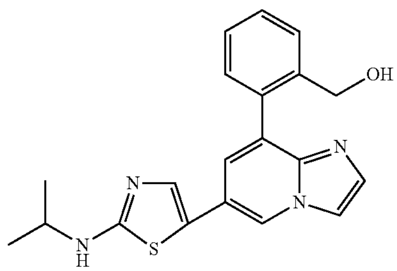 [SMILES: CC(C)Nc1ncc(-c2cc(-c3ccccc3CO)c3nccn3c2)s1] | 365.4 | 1.55, C |
| 134 | 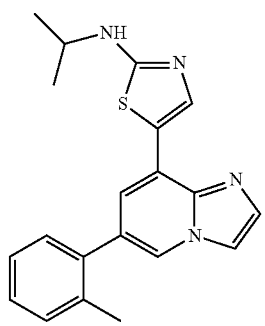 [SMILES: Cc1ccccc1-c1cc(-c2cnc(NC(C)C)s2)c2nccn2c1] | 349.4 | 2.44, C |
| 135 | 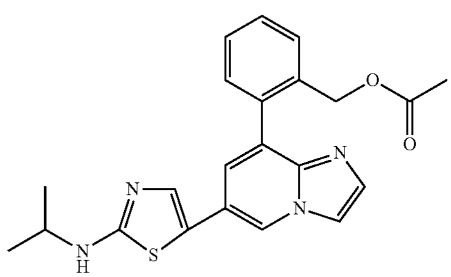 [SMILES: CC(=O)OCc1ccccc1-c1cc(-c2cnc(NC(C)C)s2)cn2ccnc12] | 407.4 | 1.81, C |
| 136 | 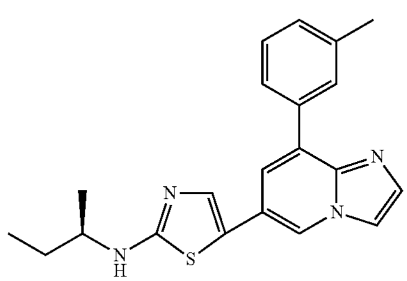 [SMILES: CC[C@@H](C)Nc1ncc(-c2cc(-c3cccc(C)c3)c3nccn3c2)s1] | 367.4 | 2.07, C |

TABLE 3-continued

| Example No. | Structure | LCMS | HPLC Tr (min) |
|---|---|---|---|
| 137 | 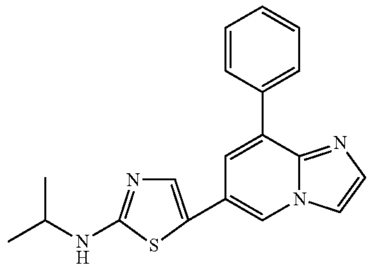 [SMILES: CC(C)Nc1ncc(-c2cc(-c3ccccc3)c3nccn3c2)s1] | 335.4 | 2.29, C |
| 138 | 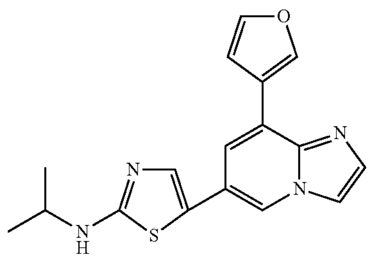 [SMILES: CC(C)Nc1ncc(-c2cc(-c3ccoc3)c3nccn3c2)s1] | 325.0 | 1.93, C |
| 139 | 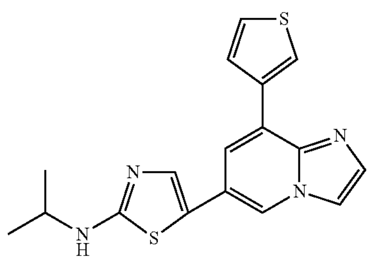 [SMILES: CC(C)Nc1ncc(-c2cc(-c3ccsc3)c3nccn3c2)s1] | 341.1 | 2.12, C |
| 140 | 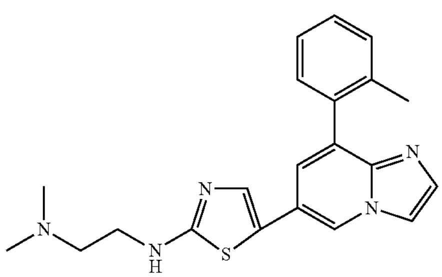 [SMILES: Cc1ccccc1-c1cc(-c2cnc(NCCN(C)C)s2)cn2ccnc12] | 365.0 | 1.77, C |
| 141 | 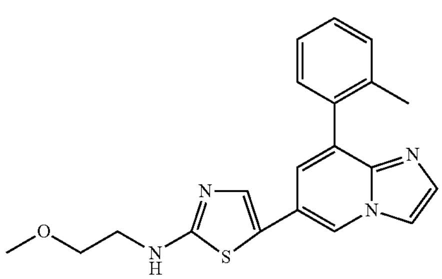 [SMILES: COCCNc1ncc(-c2cc(-c3ccccc3C)c3nccn3c2)s1] | 378.0 | 1.58, C |

TABLE 3-continued
| Example No. | Structure | LCMS | HPLC Tr (min) |
|---|---|---|---|
| 142 | 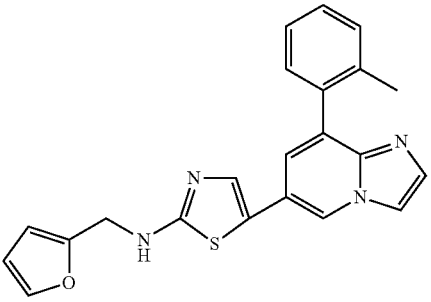 [SMILES: Cc1ccccc1-c1cc(-c2cnc(NCc3ccco3)s2)cn2ccnc12] | 387.0 | 2.28, C |
| 143 | 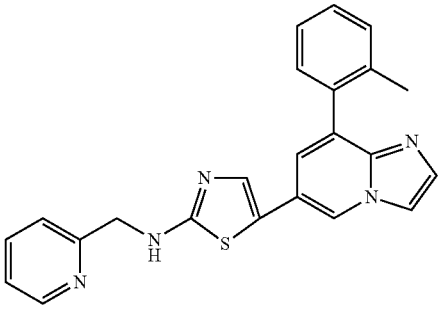 [SMILES: Cc1ccccc1-c1cc(-c2cnc(NCc3ccccn3)s2)cn2ccnc12] | 398.0 | 1.7, C |
| 144 | 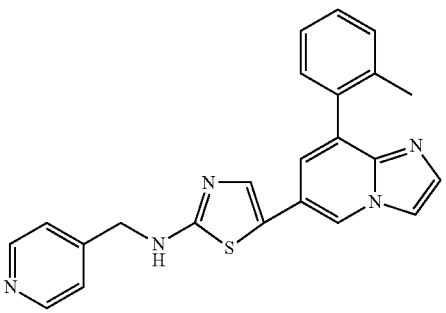 [SMILES: Cc1ccccc1-c1cc(-c2cnc(NCc3ccncc3)s2)cn2ccnc12] | 398.0 | 1.64, C |
| 145 | 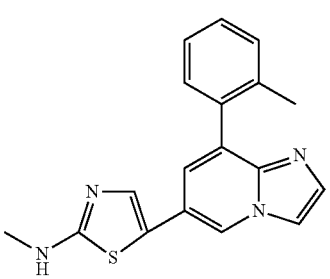 [SMILES: CNc1ncc(-c2cc(-c3ccccc3C)c3nccn3c2)s1] | 321.0 | 1.55, C |
| 146 | 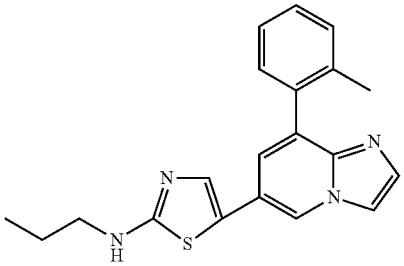 [SMILES: CCCNc1ncc(-c2cc(-c3ccccc3C)c3nccn3c2)s1] | 349.0 | 2.00, C |

TABLE 3-continued
| Example No. | Structure | LCMS | HPLC Tr (min) |
|---|---|---|---|
| 149 | 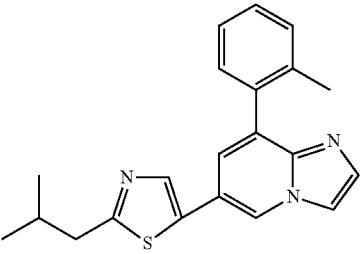 [SMILES: Cc1ccccc1-c1cc(-c2cnc(CC(C)C)s2)cn2ccnc12] | 348.0 | 2.86, C |
| 150 | 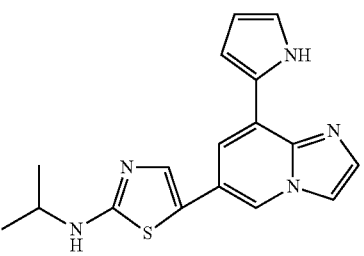 [SMILES: CC(C)Nc1ncc(-c2cc(-c3ccc[nH]3)c3nccn3c2)s1] | 324.1 | 1.75, C |
| 151 | 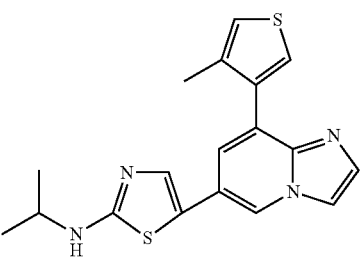 [SMILES: Cc1cscc1-c1cc(-c2cnc(NC(C)C)s2)cn2ccnc12] | 355.0 | 1.83, C |
| 152 | 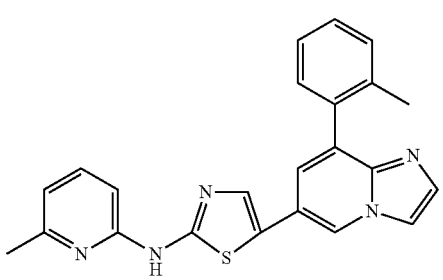 [SMILES: Cc1cccc(Nc2ncc(-c3cc(-c4ccccc4C)c4nccn4c3)s2)n1] | 398.3 | 2.57, C |
| 153 | 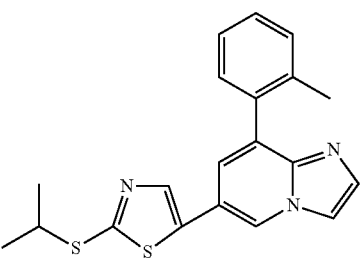 [SMILES: Cc1ccccc1-c1cc(-c2cnc(SC(C)C)s2)cn2ccnc12] | 366.3 | 2.96, C |
| 156 | 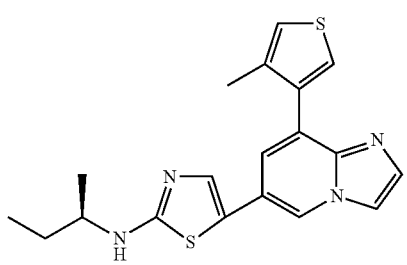 [SMILES: CC[C@@H](C)Nc1ncc(-c2cc(-c3cscc3C)c3nccn3c2)s1] | 369.2 | 2.03, C |

TABLE 3-continued

| Example No. | Structure | LCMS | HPLC Tr (min) |
|---|---|---|---|
| 157 | 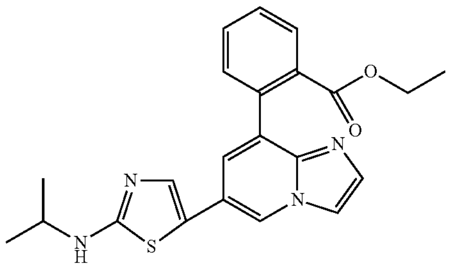 [SMILES: CCOC(=O)c1ccccc1-c1cc(-c2cnc(NC(C)C)s2)cn2ccnc12] | 407.3 | 1.96, C |
| 158 | 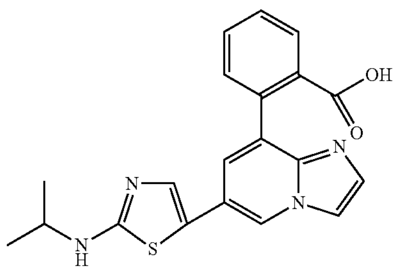 [SMILES: CC(C)Nc1ncc(-c2cc(-c3ccccc3C(=O)O)c3nccn3c2)s1] | 379.3 | 1.62, C |
| 159 | 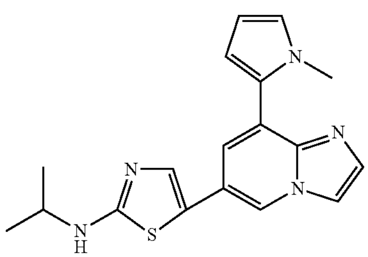 [SMILES: CC(C)Nc1ncc(-c2cc(-c3cccn3C)c3nccn3c2)s1] | 338.3 | 1.68, C |

Example 161

Methyl 2-(6-(5-(isopropylamino)thiazol-2-yl)-8-phenylimidazo[1,2-a]pyridin-2-yl)acetate

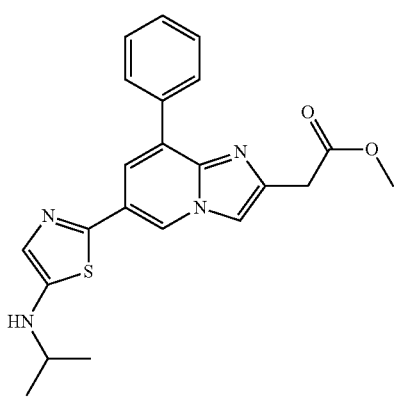 [SMILES: COC(=O)Cc1cn2cc(-c3ncc(NC(C)C)s3)cc(-c3ccccc3)c2n1]

Step 1. Preparation of methyl 2-(6,8-dibromoimidazo[1,2-a]pyridin-2-yl)acetate hydrochloride

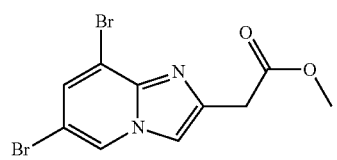 [SMILES: COC(=O)Cc1cn2cc(Br)cc(Br)c2n1]

A mixture of 3,5-dibromopyridin-2-amine (9.03 g, 35.8 mmol) and methyl 4-chloro-3-oxobutanoate (2.0 g, 13 mmol) in THF (50 mL) was heated at reflux 48 hrs. The solid was filtered and dried to give methyl 2-(6,8-dibromoimidazo[1,2-a]pyridin-2-yl)acetate hydrochloride (1.48 g, 36% yield). LCMS B: 1.54 min (RT); (M+H)$^+$=347.07 (75%), 349.07 (100%), 351.04 (75%). $^1$H NMR, 400 MHz, CDCl$_3$: δ 9.01 (d, 1.4 Hz, 1 H), 8.38 (s, 1 H), 8.07 (d, 1.4 Hz, 1 H), 4.25 (s, 2 H), 3.40 (s, 3 H).

Step 2. Preparation of methyl 2-(6-bromo-8-phenylimidazo[1,2-a]pyridin-2-yl)acetate

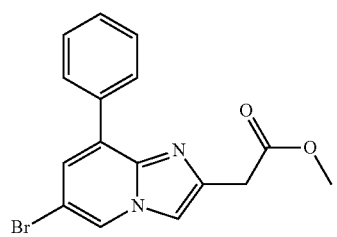 [SMILES: COC(=O)Cc1cn2cc(Br)cc(-c3ccccc3)c2n1]

A solution of methyl 2-(6,8-dibromoimidazo[1,2-a]pyridin-2-yl)acetate hydrochloride (0.26 g, 0.68 mmol) and phenylboronic acid (0.083 g, 0.68 mmol) in toluene (9 mL) and ethanol (0.5 mL) was bubbled nitrogen for 20 mins. The mixture was then treated with Pd(PPh$_3$)$_4$ (26 mg, 0.022 mmol) and K$_3$PO$_4$ (2 M, 1 mL, 2.0 mmol) and heated at 80° C. overnight. The reaction was cooled, poured into ethyl acetate (200 mL), washed with brine, separated, and concentrated. The residue was purified by column chromatography on silica gel using ethyl acetate in hexanes (10-25%) as eluent. The product containing fractions were concentrated to give 170 mg (73% yield) of methyl 2-(6-bromo-8-phenylimidazo[1,2-a]pyridin-2-yl)acetate as a white solid. LCMS B: 2.11 min (RT); (M+H)$^+$=347.21 (100%), 345.21 (100%). $^1$H NMR, 400 MHz, CDCl$_3$: δ 8.20 (d, J=1.6 Hz, 1 H), 7.96 (m, 2 H), 7.65 (s, 1H), 7.50-7.40 (m, 3 H), 7.33 (d, J=1.6 Hz, 1 H), 3.92 (s, 2 H), 3.75 (s, 3 H).

Step 3. Methyl 2-(6-(5-(isopropylamino)thiazol-2-yl)-8-phenylimidazo[1,2-a]pyridin-2-yl)acetate Prepared in an similar fashion as Example 34, step #4 from tert-butyl isopropyl(5-(4,4,5,5-tetramethyl-1,3,2-dioxaborolan-2-yl)thiazol-2-yl)carbamate and Methyl 2-(6-bromo-8-phenylimidazo[1,2-a]pyridin-2-yl)acetate. LCMS 407.4, HPLC Tr 2.02 min (Conditions C).

Example 162

2-(6-(5-(Isopropylamino)thiazol-2-yl)-8-phenylimidazo[1,2-a]pyridin-2-yl)-N-methylacetamide

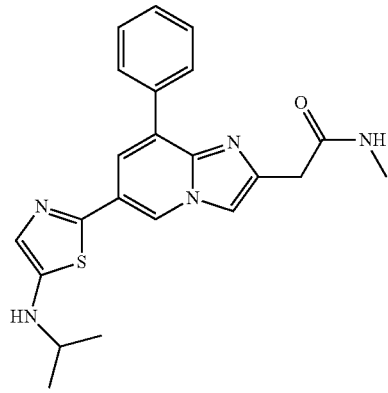 [SMILES: CNC(=O)Cc1cn2cc(-c3ncc(NC(C)C)s3)cc(-c3ccccc3)c2n1]

Example 162 was prepared from methyl 2-(6-(5-(isopropylamino)thiazol-2-yl)-8-phenylimidazo[1,2-a]pyridin-2-yl)acetate in a similar fashion as Example 32, steps 7-8. LCMS 406.7 (M+H), HPLC Tr 1.84 min (Conditions C).

Example 163

2-(6-(5-(Isopropylamino)thiazol-2-yl)-8-phenylimidazo[1,2-a]pyridin-2-yl)ethanol

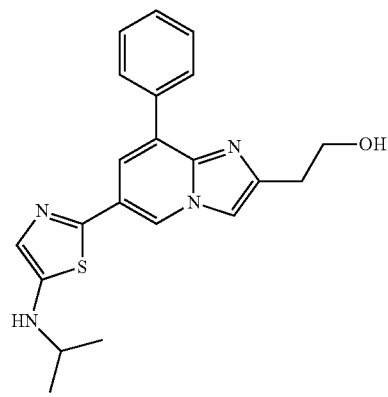 [SMILES: CC(C)Nc1cnc(-c2cc(-c3ccccc3)c3nc(CCO)cn3c2)s1]

Example 163 was prepared from methyl 2-(6-(5-(isopropylamino)thiazol-2-yl)-8-phenylimidazo[1,2-a]pyridin-2-yl)acetate in a similar fashion as Example 35. LCMS 379.4 (M+H), HPLC Tr 1.84 min (Conditions C).

Examples 164 to 170

Additional compounds prepared according to the general methods outlined above are included in Table 4.

TABLE 4

| Example No. | Structure | HPLC | LCMS |
|---|---|---|---|
| 164 | 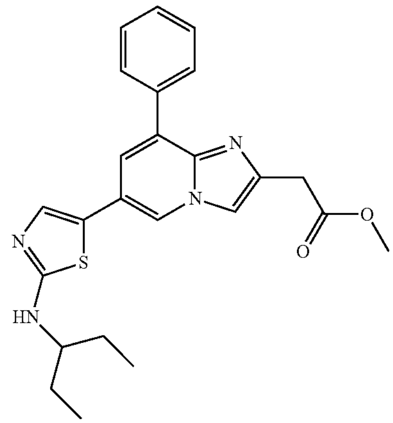 [SMILES: CCC(CC)Nc1ncc(-c2cc(-c3ccccc3)c3nc(CC(=O)OC)cn3c2)s1] | 435.4 | 2.33, C |
| 165 | 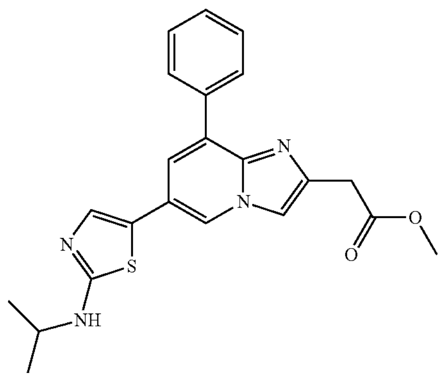 [SMILES: COC(=O)Cc1cn2cc(-c3cnc(NC(C)C)s3)cc(-c3ccccc3)c2n1] | 407.4 | 2.02, C |
| 166 | 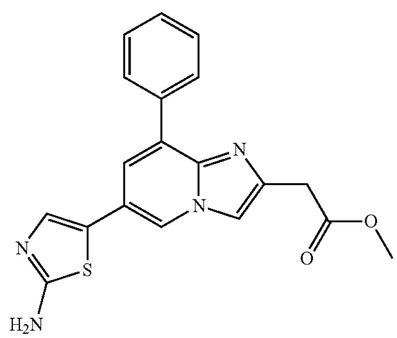 [SMILES: COC(=O)Cc1cn2cc(-c3cnc(N)s3)cc(-c3ccccc3)c2n1] | 365.3 | 1.55, C |
| 167 | 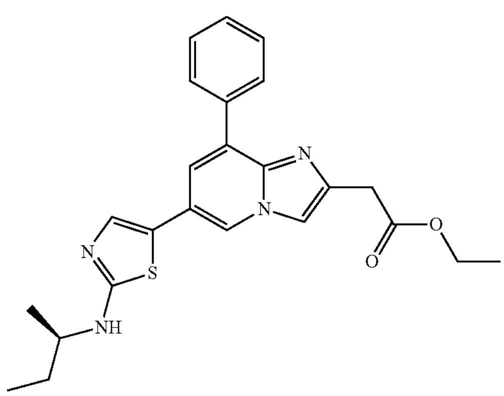 [SMILES: CCOC(=O)Cc1cn2cc(-c3cnc(N[C@H](C)CC)s3)cc(-c3ccccc3)c2n1] | 435.5 | 2.38, C |

TABLE 4-continued

| Example No. | Structure | HPLC | LCMS |
|---|---|---|---|
| 168 | 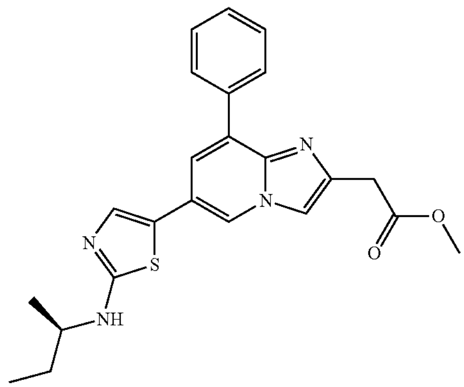 [SMILES: CC[C@@H](C)Nc1ncc(-c2cc(-c3ccccc3)c3nc(CC(=O)OC)cn3c2)s1] | 421.4 | 2.22, C |
| 169 | 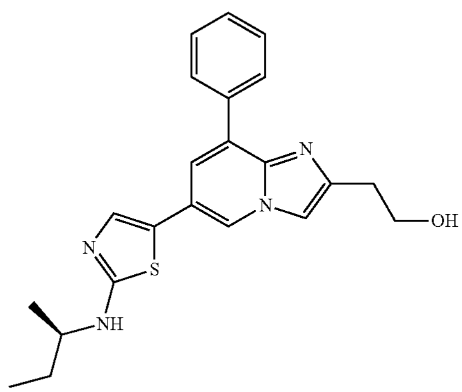 [SMILES: CC[C@@H](C)Nc1ncc(-c2cc(-c3ccccc3)c3nc(CCO)cn3c2)s1] | 393.1 | 2.00, C |
| 170 | 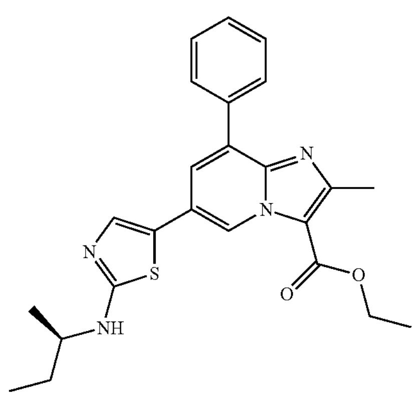 [SMILES: CCOC(=O)c1c(C)nc2c(-c3ccccc3)cc(-c3cnc(N[C@H](C)CC)s3)cn12] | 435.4 | 3.33, C |

109

Preparation of tert-butyl
isopropyl(thiazol-2-yl)carbamate

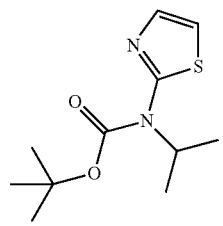 [SMILES: CC(C)N(C(=O)OC(C)(C)C)c1nccs1]

To a solution of Boc-2-aminothiazole (400 mg, 2 mmol) in THF (8 mL) at 0° C. was added triphenylphosphine (655 mg, 2.5 mmol) and IPA (0.19 mL, 2.5 mmol). DEAD (0.39 mL<2.5 mmol) was added and the reaction was allowed to warm to room temperature. The reaction was stirred for 2 h then stored at −20° C. overnight. The reaction was then concentrated to an oil and purified directly on silica gel (2.5% EtOAc/heptane) to give tert-butyl isopropyl(thiazol-2-yl)carbamate (432 mg, 90% yield).

Preparation of tert-butyl isopropyl(5-(tributylstannyl)
thiazol-2-yl)carbamate

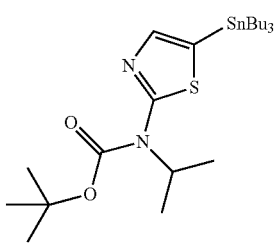

LDA (0.55M 1.1 mmol, 2M) was added to a RBF containing THF (5 mL) cooled to −78° C. A solution of tert-butyl isopropyl(thiazol-2-yl)carbamate (242 mg, 1 mmol) in THF (5 mL) was added via cannula and the resulting solution stirred for 2 h at −78° C. Tributyltin chloride (0.27 mL, 1 mmol) was added and the reaction mixture allowed to slowly warm to room temperature then stirred overnight. The reaction mixture was then quenched with NH$_4$Cl (2 mL, sat. aq.) and diluted with water. The mixture was then extracted with EtOAc (3×25 mL) and the combined organic extracts were dried (Na$_2$SO$_4$), filtered and concentrated in vacuo. The product was isolated via column chromatography (SiO$_2$, 2% EtOAc/heptane) to afford the product (214 mg, 40% yield) as a colorless oil.

Example 171

N-Isopropyl-5-(8-phenylimidazo[1,2-a]pyrazin-6-yl)
thiazol-2-amine

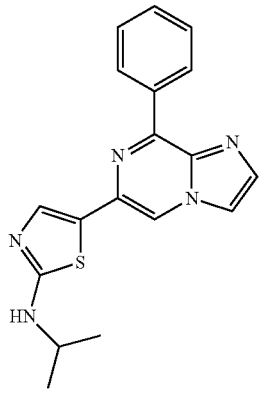 [SMILES: CC(C)Nc1ncc(-c2cn3ccnc3c(-c3ccccc3)n2)s1]

110

Step 1. Preparation of
5-bromo-3-phenylpyrazin-2-amine

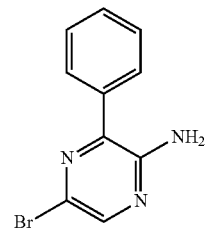 [SMILES: Nc1ncc(Br)nc1-c1ccccc1]

A mixture of 3,5-dibromopyrazin-2-amine (214 mg, 0.83 mmol) and phenyl boronic acid (100 mg, 0.8 mmol) in toluene (8 mL) was degassed and backfilled with nitrogen 3 times. Pd(PPh$_3$)$_4$ (46 mg) was added followed by 2M K$_3$PO$_4$ (0.8 mL) and EtOH (1 mL). The mixture was heated at reflux for 18 h. The solution was cooled to room temperature, partitioned between EtOAc (25 mL) and water (5 mL). The layers were separated and the organic layer dried over Na$_2$SO$_4$, filtered and concentrated to an oil which was purified via silica gel chromatography (15% EtOAc/heptane) to afford the product (187 mg, 95% yield).

Step 2. Preparation of tert-butyl 2-(5-amino-6-phe-
nylpyrazin-2-yl)thiazol-5-yl(isopropyl)carbamate

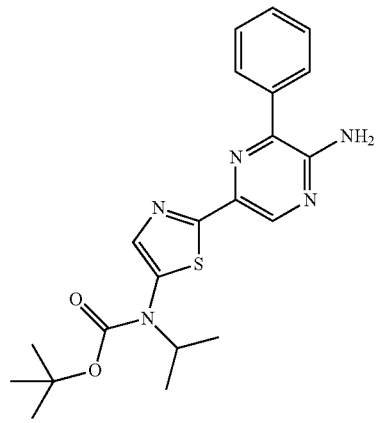 [SMILES: CC(C)N(C(=O)OC(C)(C)C)c1cnc(-c2cnc(N)c(-c3ccccc3)n2)s1]

To a solution of 5-bromo-3-phenylpyrazin-2-amine (26 mg, 0.1 mmol) and tert-butyl isopropyl(5-(tributylstannyl) thiazol-2-yl)carbamate (80 mg, 0.15 mmol) in DMF (0.4 mL) was added PdCl$_2$ (PPh$_3$)$_2$ (7 mg, 0.01 mmol) followed by DIPEA (0.044 mL, 0.25 mmol) and the reaction heated at 85° C. for 18 h. The reaction mixture was cooled to room temperature and diluted with EtOAc (6 mL) and water (2 mL). the layers were separated and the aqueous layer further extracted with EtOAc. The combined organic extracts were dried (Na$_2$SO$_4$), filtered, and concentrated in vacuo. The product was isolated via column chromatography (SiO$_2$, 25% EtOAc/ heptane) to afford the product (44 mg, 100% yield).

Step 3. Preparation of tert-butyl isopropyl(2-(8-phenylimidazo[1,2-a]pyrazin-6-yl)thiazol-5-yl)carbamate

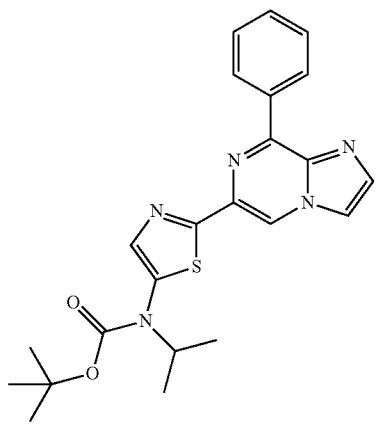 [SMILES: CC(C)N(C(=O)OC(C)(C)C)c1cnc(-c2cn3ccnc3c(-c3ccccc3)n2)s1]

A solution of tert-butyl 2-(5-amino-6-phenylpyrazin-2-yl)thiazol-5-yl(isopropyl)carbamate (23.7 mg, 0.06 mmol) in EtOH (0.25 mL) was added chloroacetaldehyde (11.8 µL, 50% in water) and the reaction mixture was then heated to 60° C. for 24 h and then concentrated to dryness. The crude product was dried under high vacuum and used without further purification.

Step 4. Preparation of N-isopropyl-5-(8-phenylimidazo[1,2-a]pyrazin-6-yl)thiazol-2-amine The crude tert-butyl isopropyl(2-(8-phenylimidazo[1,2-a]pyrazin-6-yl)thiazol-5-yl)carbamate prepared in step 3, was dissolved in dichloromethane (0.5 mL) and added TFA (0.5 mL). The reaction mixture was stirred for 4 h and the solvents were then removed. The residue was dissolved in water (0.5 mL) and neutralized with NaHCO₃ (sat. aq.). The solids were stirred overnight, filtered, and purified via prep plate chromatography (50% EtOAc/heptane) to afford N-isopropyl-5-(8-phenylimidazo[1,2-a]pyrazin-6-yl)thiazol-2-amine as a yellow solid (9.5 mg, 49% yield). LCMS 336.2 (M+H), HPLC 3.49 min (Conditions B).

Examples 172 to 175

Additional compounds prepared according to the general methods outlined above are included in Table 5.

TABLE 5

| Example No. | Structure | LCMS | HPLC |
|---|---|---|---|
| 172 | | 368.2 | 3.20, B |
| 173 | 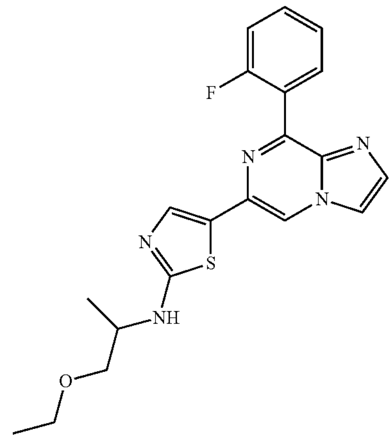 [SMILES: CCOCC(C)Nc1ncc(-c2cn3ccnc3c(-c3ccccc3F)n2)s1] | 398.2 | 3.17, B |
| 174 | 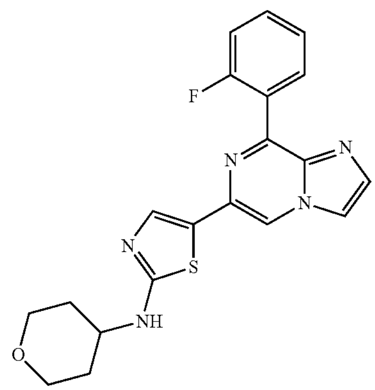 [SMILES: Fc1ccccc1-c1nc(-c2cnc(NC3CCOCC3)s2)cn2ccnc12] | 369.2 | 2.86, B |
| 175 | 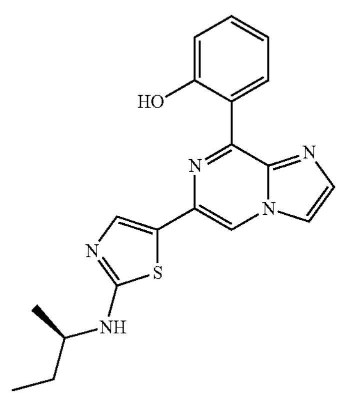 [SMILES: CC[C@@H](C)Nc1ncc(-c2cn3ccnc3c(-c3ccccc3O)n2)s1] | 366.4 | 3.74, B |

Example 176

5-(8-Ethoxyimidazo[1,2-a]pyridin-6-yl)-N-isopropylthiophen-2-amine

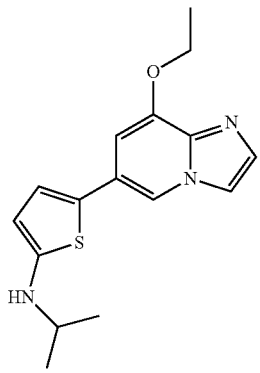 [SMILES: CCOc1cc(-c2ccc(NC(C)C)s2)cn2ccnc12]

Step 1. Preparation of 6-bromoimidazo[1,2-a]pyridin-8-ol hydrochloride

2-Amino-3-hydroxy-5-bromopyridine (Heterocycles, 1995, 41, 2799) (124 mg, 0.65 mmol) was dissolved in EtOH (3 mL) and added chloroacetaldehyde (0.2 mL, 1.3 mmol, 50% in water) and the resulting solution heated at 60° C. overnight. The solvents were then removed and the solids were crystallized from acetone to give 6-bromoimidazo[1,2-a]pyridin-8-ol hydrochloride (151 mg, 92%).

Step 2. Preparation of 6-bromo-8-ethoxyimidazo[1,2-a]pyridine

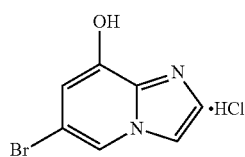 [SMILES: Oc1cc(Br)cn2ccnc12 ; Cl]

6-Bromoimidazo[1,2-a]pyridin-8-ol hydrochloride (40 mg, 0.16 mmol) and $Cs_2CO_3$ (104 mg, 0.32 mmol) in acetone (0.64 mL) and DMF (0.2 mL) was added ethyl bromide (12 μL). The reaction was stirred for 48 h then the volatile solvents were removed and the residue then added water (0.8 mL). The resulting solids were stirred, filtered, and rinsed with water. The water filtrate was extracted with EtOAc and then combined with the solid crude products. The residue was purified via column chromatography (25% then 50% EtOAc/heptane) to afford the product (19 mg, 50% yield).

Step 3

To the product of step 2 above (19 mg) was added tert-butyl isopropyl(5-(tributylstannyl)thiazol-2-yl)carbamate (64 mg, 0.12 mmol) and DMF (0.5 mL). PdCl2(PPh3)2 (5.6 mg, 0.008 mmol) was added and the reaction mixture heated at 85° C. for 24 h. The reaction was then cooled to room temperature and the solution applied directly to a silica gel plug (50% EtOAc/heptane) and the product containing fractions concentrated and used directly without further purification.

The above crude solid was dissolved in dichloromethane (1 mL) and added TFA (0.25 mL) and stirred overnight. The solvents were removed and the resulting oil was added NaHCo3 91 mL, sat. aq.). The solids were collected and then purified via HPLC to give 5-(8-ethoxyimidazo[1,2-a]pyridin-6-yl)-N-isopropylthiophen-2-amine (11.3 mg, 47% yield) as the TFA salt. LCMS 303.22 (M+H); HPLC Tr 1.98 min (Conditions B).

Examples 177 to 179

Additional compounds prepared according to the general methods outlined above are included in Table 6.

TABLE 6

| Example No. | Structure | LCMS | HPLC |
|---|---|---|---|
| 177 | 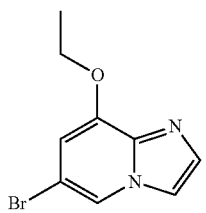 | 343.2 | 2.56, B |
| 178 | 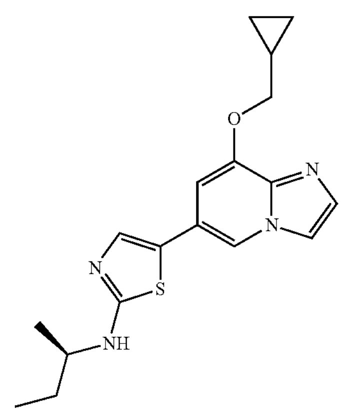 [SMILES: CC[C@@H](C)Nc1ncc(-c2cc(OCC3CC3)c3nccn3c2)s1] | 343.3 | 2.53, B |

TABLE 6-continued

| Example No. | Structure | LCMS | HPLC |
|---|---|---|---|
| 179 | 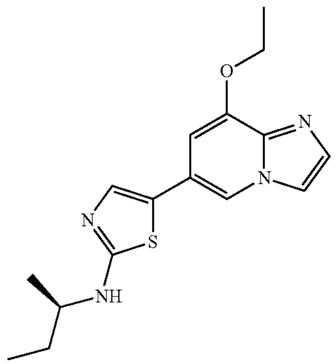 [SMILES: CCOc1cc(-c2cnc(N[C@H](C)CC)s2)cn2ccnc12] | 317.2 | 2.19, B |

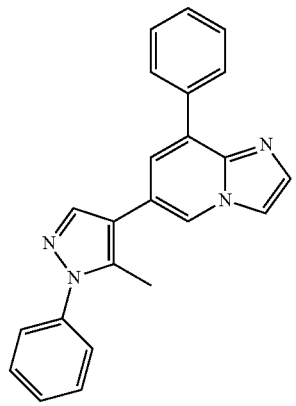 [SMILES: Cc1c(-c2cc(-c3ccccc3)c3nccn3c2)cnn1-c1ccccc1]

Example 180

6-(5-Methyl-1-phenyl-1H-pyrazol-4-yl)-8-phenylimidazo[1,2-a]pyridine

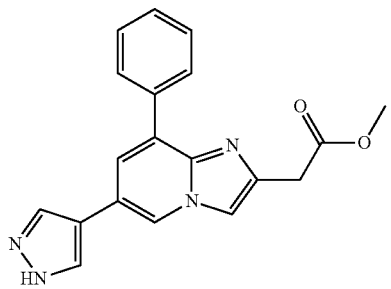 [SMILES: COC(=O)Cc1cn2cc(-c3cn[nH]c3)cc(-c3ccccc3)c2n1]

Example 180 was prepared in a similar fashion as Example 70 starting from 4-bromo-5-methyl-1-phenyl-1H-pyrazole. LCMS 351.3 (M+H); HPLC Tr 3.35 min (Conditions B).

Example 181

Methyl 2-(8-phenyl-6-(1H-pyrazol-4-yl)imidazo[1,2-a]pyridin-2-yl)acetate

Example 181 was prepared in a similar fashion as Example 161, Step 3 using tert-butyl 4-(4,4,5,5-tetramethyl-1,3,2-dioxaborolan-2-yl)-1H-pyrazole-1-carboxylate. LCMS 333.3 (M+H); HPLC Tr 1.92 min (Conditions C).

Example 182

Ethyl 8-(2,4-difluorophenyl)-6-(2-isobutylthiazol-5-yl)imidazo[1,2-a]pyridine-2-carboxylate

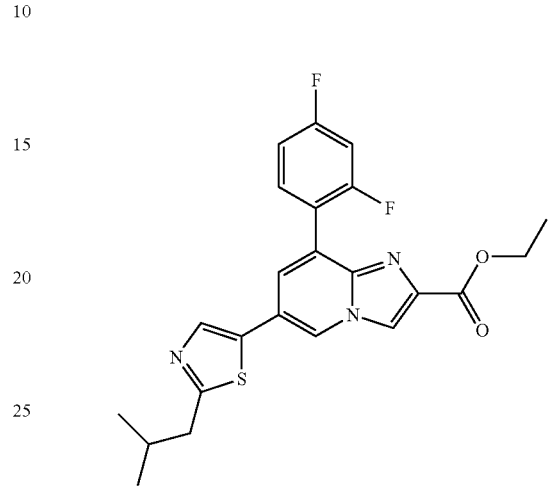

Step 1. 2-Isobutyl-5-(4,4,5,5-tetramethyl-1,3,2-dioxaborolan-2-yl)thiazole

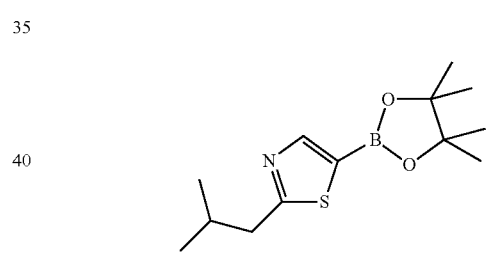

To a solution of 5-bromo-2-isobutylthiazole (2.10 g, 9.54 mmol) in THF (20 mL) was added 1.6 M n-butyllithium in hexane solution (7.15 mL, 11.44 mmol) dropwise over 45 minutes at −78° C. The resulting solution was stirred at −78° C. for 10 minutes. Then the 2-isopropoxy-4,4,5,5-tetramethyl-1,3,2-dioxaborolane (2.13 g, 11.44 mmol) was added to the above solution and stirred at −78° C. for 1.5 hours. The reaction was quenched with 1:1 saturated ammonium chloride and water and warmed up to close to room temperature. The resulting mixture was extracted with ethyl acetate, washed with water, brine and concentrated. The residue was subjected to flash column chromatography using 30% ethyl acetate/hexane to give a yellow oil (454 mg, 18% yield). $^1$H NMR, 400 MHz, CDCl$_3$: δ 8.13 (s, 1 H), 2.95 (d, J=7.1 Hz, 2 H), 2.10-2.19 (m, 1 H), 1.36 (s, 12 H), 1.00 (d, J=6.6 Hz, 6 H).

Example 182 was prepared in a similar fashion as Example 33, step 2. LCMS (Conditions C): 3.92 min (Tr); (M+H)$^+$= 442.29 (100%), 443.32 (30%), 444.32 (10%).

Example 183

8-(2,4-Difluorophenyl)-6-(2-isobutylthiazol-5-yl)imidazo[1,2-a]pyridine-2-methanol

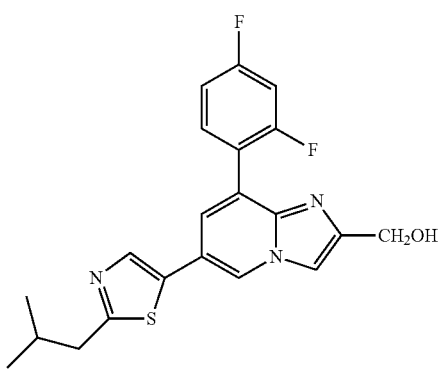 [SMILES: CC(C)Cc1ncc(-c2cc(-c3ccc(F)cc3F)c3nc(CO)cn3c2)s1]

To a solution of ethyl 8-(2,4-difluorophenyl)-6-(2-isobutylthiazol-5-yl)imidazo[1,2-a]pyridine-2-carboxylate (47.2 mg, 0.107 mmol) in THF (2 mL) was added lithium aluminum hydride powder (12.2 mg, 0.321 mmol). The mixture was stirred at room temperature overnight, then added 1N NaOH (12 mL) and water (3 mL), extracted with dichloromethane, concentrated. The residue was subjected to flash column chromatography using 80% ethyl acetate and hexane to give a white solid (3.9 mg, 9% yield). LCMS (Conditions C): Tr 2.83 min; (M+H)$^+$=400.25 (100%), 401.36 (20%), 402.36 (10%). $^1$H NMR, 400 MHz, CDCl$_3$: 8.22 (d, J=1.5 Hz, 1H), 7.81 (m, 1H), 7.76 (s, 1H), 7.58 (s, 1H), 7.39 (s, 1H), 7.00-6.88 (m, 2H), 4.78 (s, 2H), 2.84 (d, J=7.1 Hz, 2H), 2.08 (m, 1H), 0.97 (d, J=6.6 Hz, 6H).

Example 184

8-(2,4-Difluorophenyl)-6-(2-isobutylthiazol-5-yl)imidazo[1,2-a]pyridine-2-carboxylic acid

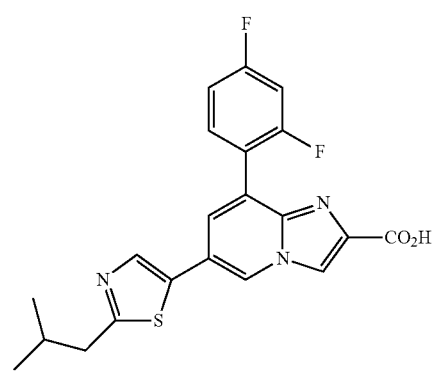 [SMILES: CC(C)Cc1ncc(-c2cc(-c3ccc(F)cc3F)c3nc(C(=O)O)cn3c2)s1]

To a solution of ethyl 8-(2,4-difluorophenyl)-6-(2-isobutylthiazol-5-yl)imidazo[1,2-a]pyridine-2-carboxylate (47.7 mg, 0.108 mmol) in MeOH (2 mL) and THF (2 mL) was added 1N NaOH (2 mL). The mixture was stirred at room temperature overnight. The mixture was concentrated, diluted with EtOAc (10 mL), washed with water (5 mL) and concentrated. The residue was purified by prep HPLC to give a white solid as a TFA salt form (32 mg, 56% yield). LCMS (Conditions C): Tr 3.55 min; (M+H)$^+$=414.29 (100%), 415.37 (20%), 416.26 (10%). $^1$H NMR, 400 MHz, CDCl$_3$: 8.37 (d, J=1.5 Hz, 1H), 8.33 (s, 1H), 7.92 (s, 1H), 7.88 (m, 1H), 7.61 (s, 1H), 7.13-7.03 (m, 2H), 2.96 (d, J=7.1 Hz, 2H), 2.18 (m, 1H), 1.06 (d, J=6.6 Hz, 6H).

Example 186

An additional compound prepared according to the general methods outlined above is included in Table 7.

TABLE 7

| Example No. | Structure | LCMS | HPLC |
|---|---|---|---|
| 186 | 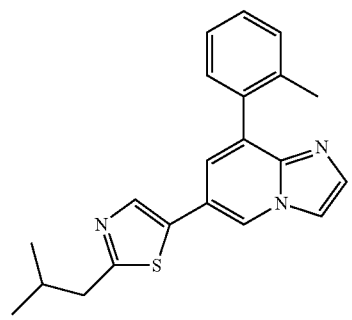 [SMILES: Cc1ccccc1-c1cc(-c2cnc(CC(C)C)s2)cn2ccnc12] | 420.2 | 3.87, C |

Example 189

2-Isobutyl-5-(8-o-tolylimidazo[1,2-a]pyridin-6-yl)thiazole

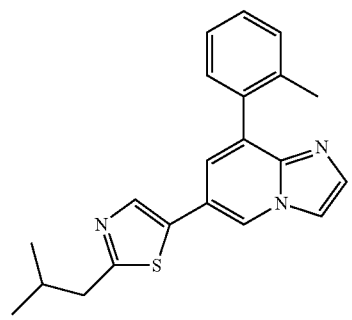 [SMILES: Cc1ccccc1-c1cc(-c2cnc(CC(C)C)s2)cn2ccnc12]

Step 1. 5-Bromo-2-isobutylthiazole

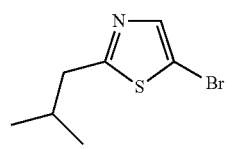

To a solution of 2-isobutylthiazole (600 mg, 4.25 mmol) in DMF (2 mL) was added N-bromosuccinimide (1.134 g, 6.37 mmol). The mixture was stirred at room temperature for 3 hours then subjected to flash column chromatography using 10% ethyl acetate/hexane to give a yellow oil (815.2 mg, 87% yield). LCMS (Conditions C): Tr 3.51 min; (M+H)+: 219.90 (100%), 221.90 (100%).

Step 2

Example 189 was prepared using the procedure describe for Example 34, step 4, from 5-bromo-2-isobutylthiazole and 8-o-tolylimidazo[1,2-a]pyridin-6-ylboronic acid. LCMS (Conditions C): Tr 2.86 min.; (M+H)+: 348.0

Example 190

2-(Isopropylthio)-5-(8-o-tolylimidazo[1,2-a]pyridin-6-yl)thiazole

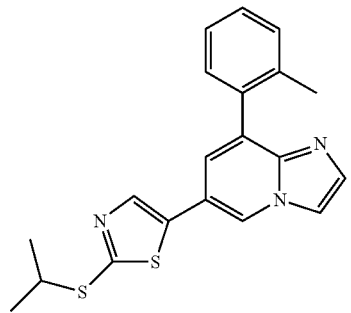 [SMILES: Cc1ccccc1-c1cc(-c2cnc(SC(C)C)s2)cn2ccnc12]

Step 1. 2-(Isopropylthio)thiazole

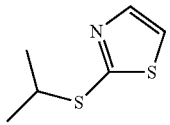

To a solution of thiazole-2-thiol (300 mg, 2.56 mmol), isopropanol (154 mg, 2.56 mmol) and triphenylphosphine (671.5 mg, 2.56 mmol) in THF (5 mL) was added DEAD (445.8 mg, 2.56 mmol) dropwise at room temperature. The mixture was stirred at room temperature for 3 hours. Reaction was completed according to t.l.c. The reaction mixture was allowed to stir over the weekend then concentrated and the residue was subjected to flash column chromatography using 10% ethyl acetate/hexane as solvent to give a colorless oil (260 mg, 64% yield).

Step 2. 5-Bromo-2-(isopropylthio)thiazole

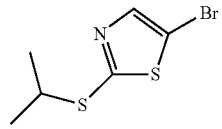

To a solution of 2-(isopropylthio)thiazole (260 mg, 1.63 mmol) in DMF (2 mL) was added N-bromosuccinimide (435.8 mg, 2.45 mmol). The mixture was stirred at room temperature for 3 hours then subjected to flash column chromatography using 10% ethyl acetate/hexane to give a yellow oil (390 mg, 100% yield). LCMS (Conditions C): Tr 3.67 min.; (M+H): 237.86 (30%), 239.86 (30%), 195.86 (100%), 197.86 (100%).

Step 3

Prepared using the procedure describe for Example 34, step 4 from 5-bromo-2-(isopropylthio)thiazole and 8-o-tolylimidazo[1,2-a]pyridin-6-ylboronic acid. LCMS (Conditions C): Tr 2.96 min.; (M+H)+: 366.3.

Example 191

2-(Ethoxy)-5-(8-o-tolylimidazo[1,2-a]pyridin-6-yl)thiazole

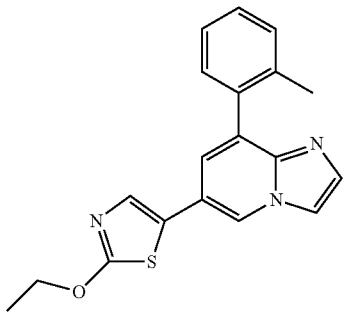 [SMILES: CCOc1ncc(-c2cc(-c3ccccc3C)c3nccn3c2)s1]

Step 1. 5-Bromo-2-ethoxythiazole

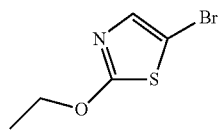

To a solution of 2-isopropoxythiazole (300 mg, 2.32 mmol) in DMF (2 mL) was added N-bromosuccinimide (620 mg, 3.48 mmol). The mixture was stirred at room temperature for 3 hours then subjected to flash column chromatography using 10% ethyl acetate/hexane to give a colorless oil (440 mg, 91% yield). LCMS (Conditions C): Tr 3.27 min.; (M+H): 207.88 (20%), 209.88 (20%), 179.87 (100%), 181.87 (100%).

Step 2

Example 190 was prepared using the procedure describe for Example 34, step 4 from 5-bromo-2-(isopropyloxy)thiazole and 8-o-tolylimidazo[1,2-a]pyridin-6-ylboronic acid. LCMS (Conditions C): Tr 2.63 min.; (M+H)+: 336.31

Example 192

Scheme 1, 2 or 3 above is used to prepare triazolopyridine compounds similar to the imidazopyridine compounds of Examples 32-39, 41, 45, 47-67, 70-92, 94-98, 101-110, 112-146, 149-153, 156-159, 161-170, 176-186 and 189-191 except that the imidazo ring in the examples is a triazolo ring.

Example 193

Scheme 1, 2 or 3 above is used to prepare triazolopyridine compounds similar to the imidazopyrazine compounds of Examples 171-175 except that the imidazo ring in the examples is a triazolo ring and the pyrazine ring in the examples is a pyridine ring.

Test Data

The data in Table 8, below, describes the activity of selected examples. The data was obtained using the assays described above.

Preferred triazolopyridine compounds of the invention have a p38 inhibition activity ($IC_{50}$) of less than about 0.1 µM, preferably less than about 0.05 µM, more preferably less than about 0.02 µM and most preferably less than about 0.01 µM. Preferred suitable ranges for p38 inhibition activity ($IC_{50}$) include about 0.01 µM to about 0.1 µM, preferably about 0.01 µM to about 0.02 µM.

Preferred imidazopyridine compounds of the invention have a p38 inhibition activity ($IC_{50}$) of less than about 0.04 µM, preferably less than about 0.03 µM, more preferably less than about 0.006 µM and most preferably less than about 0.003 µM. The $IC_{50}$ may be as low as 0.001 µM. Preferred suitable ranges for p38 inhibition activity ($IC_{50}$) include about 0.003 µM to about 0.04 µM, preferably about 0.003 µM to about 0.006 µM.

Preferred imidazopyrazine compounds of the invention have a p38 inhibition activity ($IC_{50}$) of less than about 0.1 µM, preferably less than about 0.06 µM, more preferably less than about 0.04 µM and most preferably less than about 0.02 µM. Preferred suitable ranges for p38 inhibition activity ($IC_{50}$) include about 0.02 µM to about 0.1 µM, preferably about 0.02 µM to about 0.04 µM.

TABLE 8

| Example No. | p38 IC50 (uM) |
|---|---|
| 6 | 0.013 |
| 10 | 0.015 |
| 12 | 0.581 |
| 15 | 0.091 |
| 26 | 0.604 |
| 37 | 0.037 |
| 48 | 0.040 |
| 56 | 0.006 |
| 72 | 0.0059 |
| 73 | 0.0034 |
| 74 | 0.0057 |
| 83 | 0.0390 |
| 86 | 0.0416 |
| 104 | 0.0358 |
| 117 | 0.807 |
| 128 | 0.926 |
| 129 | 0.669 |
| 131 | 1.543 |
| 132 | 0.005 |
| 140 | 1.780 |
| 151 | 0.0052 |
| 156 | 0.003 |
| 157 | 0.795 |
| 163 | 0.038 |
| 168 | 0.033 |
| 171 | 0.060 |
| 172 | 0.023 |
| 173 | 0.040 |
| 174 | 0.109 |
| 175 | 0.809 |
| 180 | 0.630 |
| 181 | 0.924 |

What is claimed is:

1. A compound of Formula I:

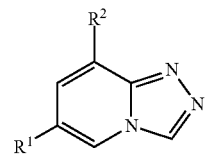

and enantiomers, diastereomers and pharmaceutically-acceptable salts thereof, wherein:
$R^1$ is thiazol-5-yl substituted at the 2 position with lower alkyl amino; and
$R^2$ is phenyl or phenyl substituted with one or more substituents selected from the group consisting of halo, cyano, $C_1$-$C_4$ alkyl and hydroxy.

2. The compound according to claim 1, wherein the $R^1$ is thiazol-5-yl substituted at the 2 position with $C_1$ to $C_6$ alkyl amino.

3. The compound according to claim 1, wherein $R^1$ is thiazol-5-yl is substituted at the 2 position with $C_1$ to $C_4$ alkyl amino.

4. The compound according to claim 1, wherein $R^1$ is selected from the group consisting of:

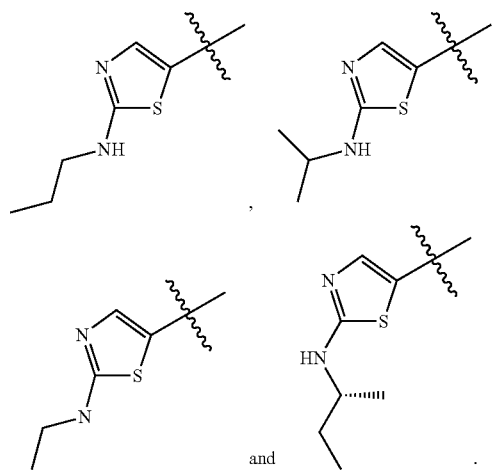

5. The compound according to claim 1, wherein $R^2$ is phenyl or phenyl substituted with one to two substituents selected from the group consisting of halo, cyano, $C_1$-$C_4$ alkyl and hydroxy.

6. The compound according to claim 1, wherein $R^2$ is phenyl or phenyl substituted with one or more substituents selected from the group consisting of halo, cyano, methyl and hydroxy.

7. The compound according to claim 1, wherein $R^2$ is phenyl.

8. The pharmaceutical composition comprising at least one compound according to claim 1 and a pharmaceutically-acceptable carrier or diluent.

9. A pharmaceutical composition according to claim 8, wherein said composition is a solid dosage form.

10. The compound according to claim 1 wherein said compound is selected from:

123
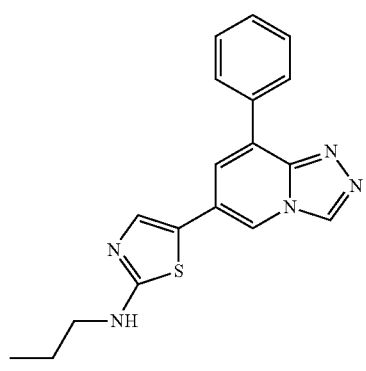
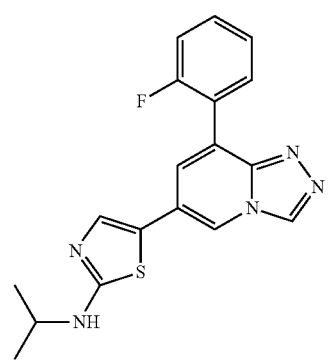
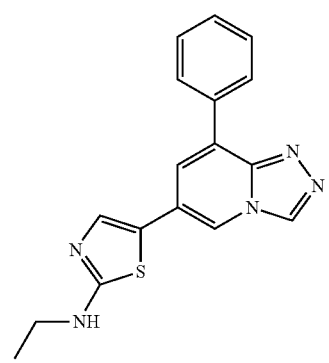
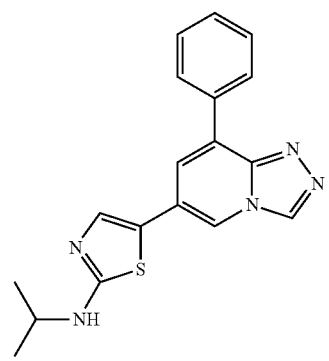
124
-continued
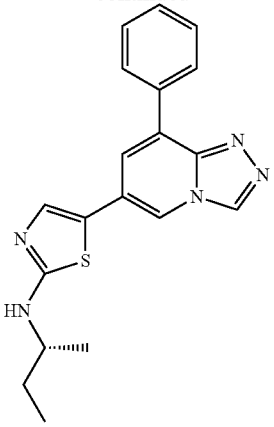
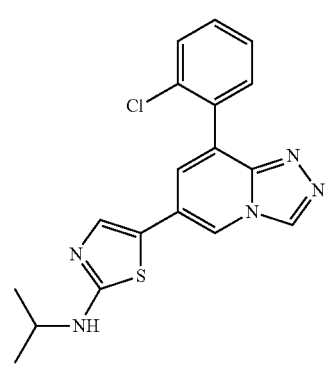
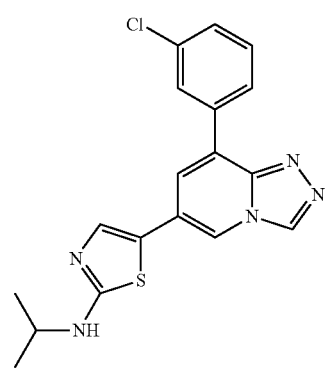
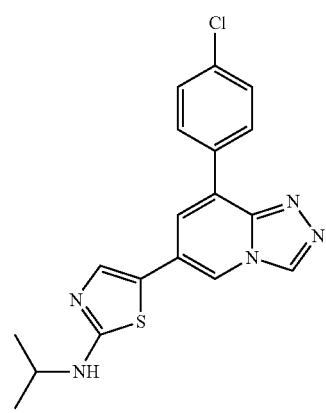

125
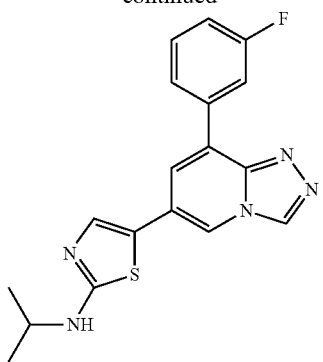
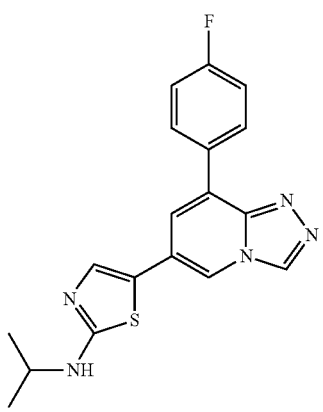
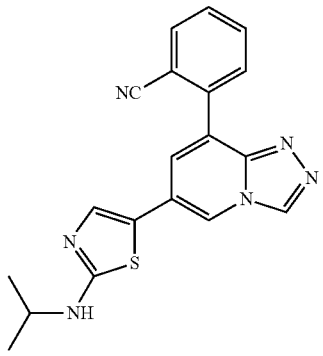
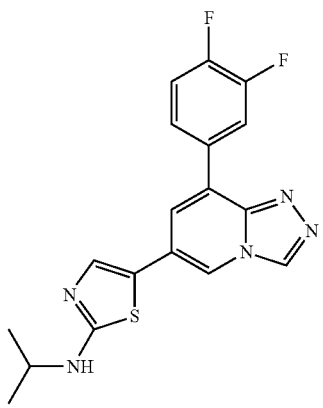
126
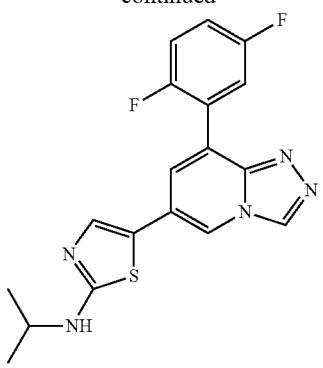
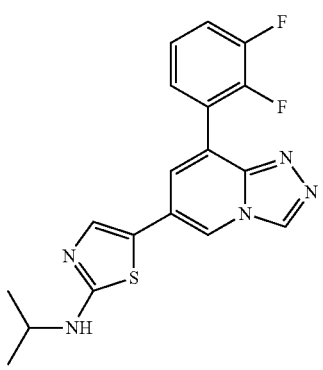
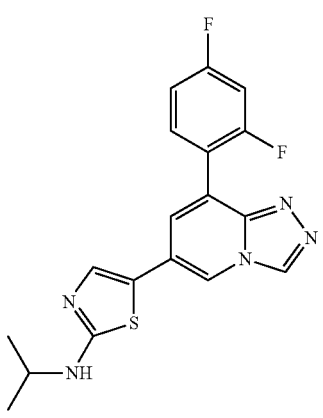

-continued
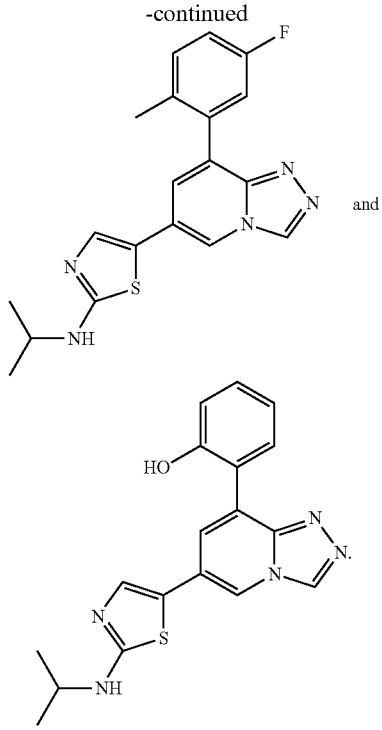
and
11. The compound according to claim 6, wherein $R^1$ is selected from the group consisting of:
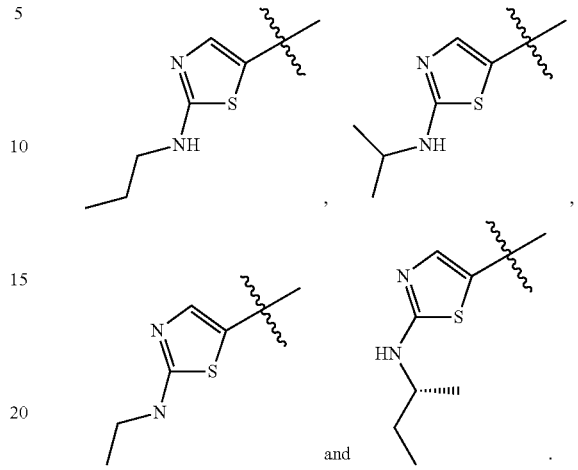
and
12. The compound according to claim 11, wherein $R^2$ is phenyl or phenyl substituted with one to two substituents selected from F, Cl, cyano, methyl, and hydroxy.
* * * * *

UNITED STATES PATENT AND TRADEMARK OFFICE
CERTIFICATE OF CORRECTION

PATENT NO. : 8,410,128 B2
APPLICATION NO. : 12/738860
DATED : April 2, 2013
INVENTOR(S) : John Hynes et al.

Page 1 of 1

It is certified that error appears in the above-identified patent and that said Letters Patent is hereby corrected as shown below:

In the Claims:

In Claim 1, col. 122, line 15, delete "$R^1$ is" and insert -- $R^1$ is --, therefor.

In Claim 1, col. 122, line 20, delete "$C_1$-$C_4$" and insert -- $C_1$-$C_4$ --, therefor.

In Claim 2, col. 122, line 21, delete "$R^1$ is" and insert -- $R^1$ is --, therefor.

In Claim 3, col. 122, line 24, delete "$R^1$ is" and insert -- $R^1$ is --, therefor.

In Claim 4, col. 122, line 27, delete "$R^1$ is" and insert -- $R^1$ is --, therefor.

In Claim 6, col. 122, line 56, delete "methyl and" and insert -- methyl, and --, therefor.

In Claim 11, col. 128, line 1, delete "$R^1$ is" and insert -- $R^1$ is --, therefor.

Signed and Sealed this
Twenty-ninth Day of October, 2013

Teresa Stanek Rea
*Deputy Director of the United States Patent and Trademark Office*